(12) United States Patent
Moss, Jr.

(10) Patent No.: US 11,684,341 B1
(45) Date of Patent: Jun. 27, 2023

(54) POINT-OF-CARE GUIDANCE SYSTEM FOR DIAGNOSTIC AND THERAPEUTIC MEDICAL PROCEDURES

(71) Applicant: V.E.I.N., LLC, Wartrace, TN (US)

(72) Inventor: Max L. Moss, Jr., Murfreesboro, TN (US)

( * ) Notice: Subject to any disclaimer, the term of this patent is extended or adjusted under 35 U.S.C. 154(b) by 0 days.

(21) Appl. No.: 17/581,034

(22) Filed: Jan. 21, 2022

Related U.S. Application Data

(63) Continuation-in-part of application No. 17/391,251, filed on Aug. 2, 2021, which is a continuation-in-part of application No. PCT/US2020/016427, filed on Feb. 3, 2020.

(60) Provisional application No. 62/799,777, filed on Feb. 1, 2019.

(51) Int. Cl.
*A61B 8/00* (2006.01)
*G06V 40/16* (2022.01)

(52) U.S. Cl.
CPC .......... *A61B 8/4427* (2013.01); *A61B 8/4254* (2013.01); *A61B 8/462* (2013.01); *A61B 8/56* (2013.01); *G06V 40/171* (2022.01)

(58) Field of Classification Search
CPC ..... A61B 8/4427; A61B 8/4254; A61B 8/462; A61B 8/56; G06V 40/171
See application file for complete search history.

(56) References Cited

U.S. PATENT DOCUMENTS

| | | | | |
|---|---|---|---|---|
| 3,893,449 | A * | 7/1975 | Lee | A61B 8/4427 600/459 |
| 6,122,538 | A * | 9/2000 | Sliwa, Jr. | A61B 8/483 600/407 |
| 2010/0317990 | A1* | 12/2010 | Leimbach | A61B 90/17 600/562 |
| 2016/0007956 | A1* | 1/2016 | Mauldin, Jr. | A61B 8/0841 600/443 |
| 2016/0213350 | A1* | 7/2016 | Lee | A61B 8/4444 |
| 2017/0238901 | A1* | 8/2017 | Henderson | A61B 6/4405 |
| 2017/0286754 | A1* | 10/2017 | Eder | H04N 5/33 |
| 2018/0042581 | A1* | 2/2018 | Sonnenschein | A61B 8/4494 |
| 2020/0229798 | A1* | 7/2020 | Leyvi | G16H 40/63 |
| 2020/0337544 | A1* | 10/2020 | Goldfarb | A61B 1/0669 |
| 2021/0192528 | A1* | 6/2021 | Zhao | G06Q 20/326 |

* cited by examiner

*Primary Examiner* — Yi-Shan Yang
*Assistant Examiner* — Alexei Bykhovski
(74) *Attorney, Agent, or Firm* — Michael D. Lazzara; Leech Tishman Fuscaldo and Lampl

(57) ABSTRACT

A guidance apparatus is provided for use with a portable imaging apparatus and an image display. The guidance apparatus comprises a coupling mechanism which may include a slip ring portion structured for receiving the imaging apparatus therein. The coupling mechanism can be structured for: facilitating orienting the image display device to provide a direct line of sight of an area imaged by the imaging apparatus; adjusting to facilitate rotation of the image display device in at least one 360-degree plane of rotation about a longitudinal axis extending through the imaging apparatus; allowing selection of an image display device position associated with a viewing angle of the image display device; and allowing the coupling mechanism, the image display device, and the imaging apparatus, in combination, to be held in a single hand of a user during performance of an imaging procedure.

18 Claims, 53 Drawing Sheets

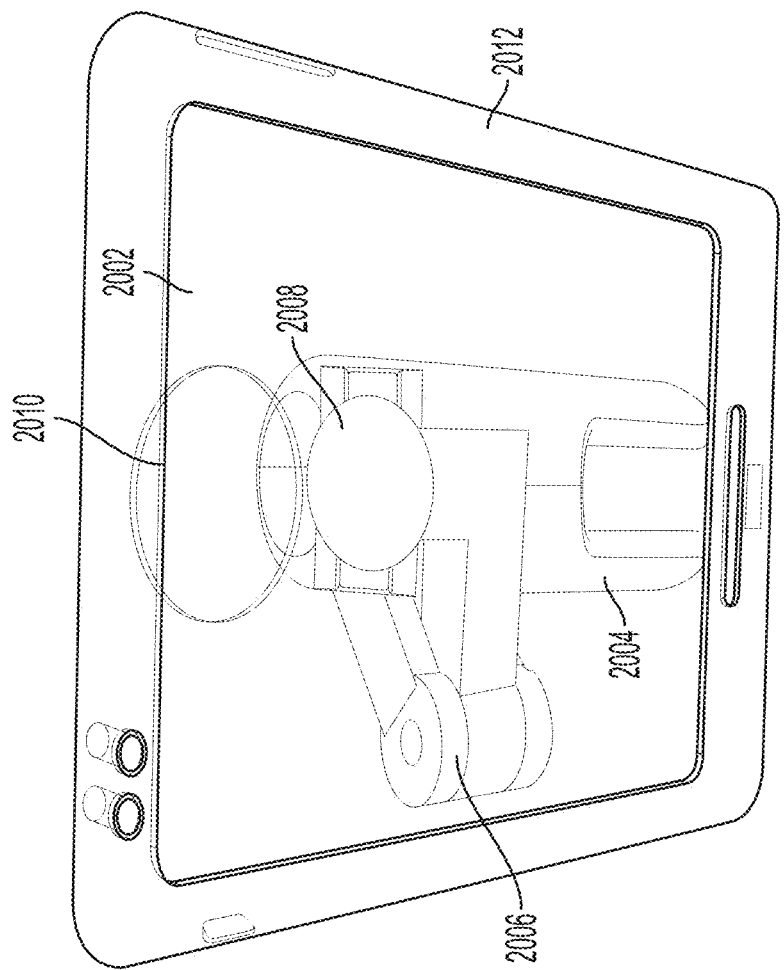

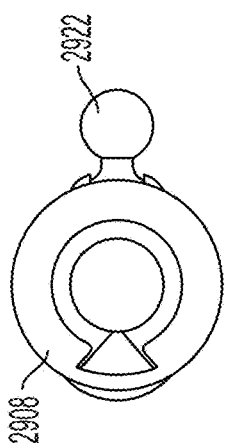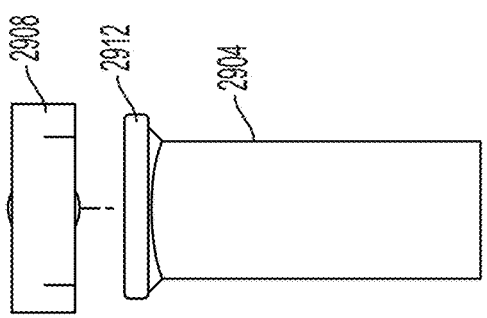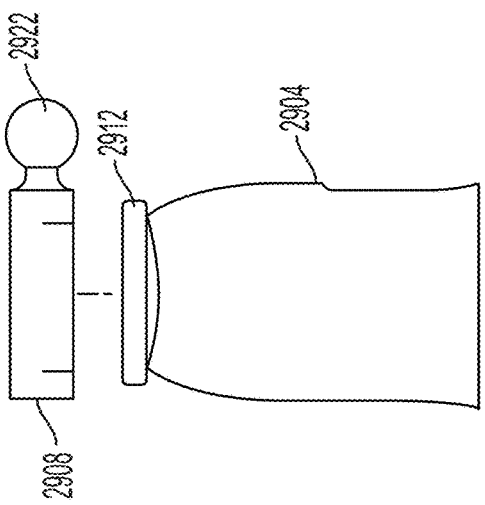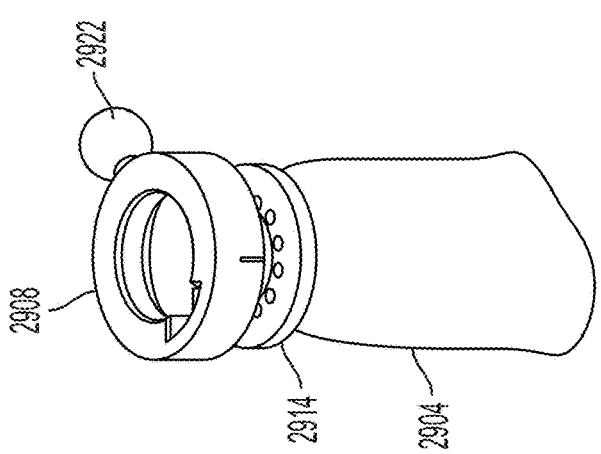

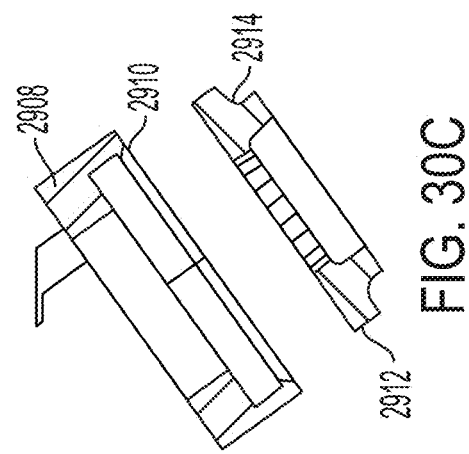
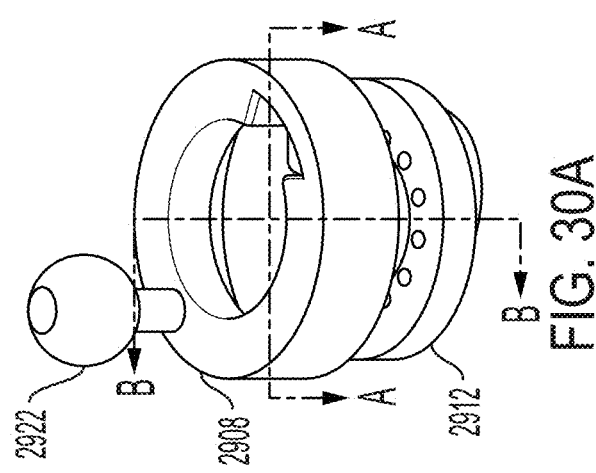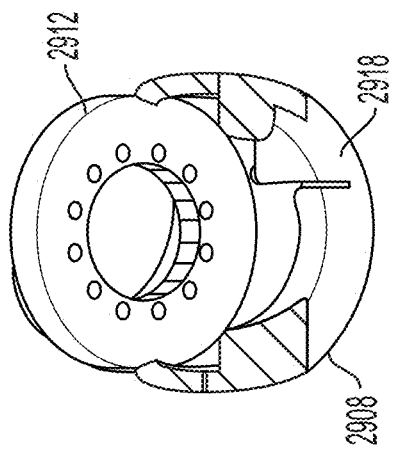

POINT-OF-CARE GUIDANCE SYSTEM FOR DIAGNOSTIC AND THERAPEUTIC MEDICAL PROCEDURES

CROSS-REFERENCE TO RELATED APPLICATIONS

The present application is a continuation-in-part application which claims priority to U.S. patent application Ser. No. 17/391,251, filed on Aug. 2, 2021, which is a continuation-in-part application that claims priority to Patent Cooperation Treaty Patent Application PCT/US2020/016427, filed on Feb. 3, 2020, which in turn claims the priority benefit of U.S. Provisional Patent Application Ser. No. 62/799,777, filed on Feb. 1, 2019, and the entirety of all of the aforementioned priority applications are incorporated herein by reference.

FIELD OF THE INVENTION

Various embodiments of devices, tools, techniques, and computer-based technology are provided to assist with medical and veterinarian diagnostic imaging and image guided procedure performance. In particular embodiments, point of care ultrasound (POCUS) techniques can be used for evaluating vascular conditions and characteristics, and for guiding and facilitating vascular access procedures performed during a medical procedure.

BACKGROUND

Vascular access as well as other medical treatments and procedures, such as procedures involving drainage, biopsies, perfusions, infusions, injections, nerve block injections, tubes for spine treatment, as well as others are important considerations for healthcare professionals. Whether these procedures are performed optimally can have a significant impact on effective patient treatment. For example, identifying an appropriate blood vessel in the arm of a patient, as well as the vessel's suitability for an injection procedure, are essential elements of effectively administering medicine to the patient. Such medical procedures need to be performed in ways that reduce or eliminate opportunities for human error whenever possible.

In view of these issues, improved tools and techniques are needed which can facilitate vascular access and other procedures needed for both routine and emergency medical treatments and diagnoses, guide the medical professional's decision-making process for the appropriate procedure, and train medical professionals in how to effectively and efficiently perform procedures.

BRIEF DESCRIPTION OF THE FIGURES

Various embodiments of the present invention are described with reference to the following figures, wherein like reference numerals refer to like parts throughout the various views:

FIGS. 20A through 20D illustrate different views of another example of a cradle which can be used in accordance with certain embodiments of a vascular guidance system structured in accordance with various embodiments of the invention.

FIG. 29A is a partially exploded three-dimensional view illustrating one example of a coupling mechanism structured in accordance with certain embodiments of the invention.

FIG. 29B is a side view of the coupling mechanism of FIG. 29A.

FIG. 29C is a back view of the coupling mechanism of FIG. 29A.

FIG. 29D is a top view of the coupling mechanism of FIG. 29A.

FIG. 30A is a partially exploded three-dimensional view illustrating one example of certain aspects of a coupling mechanism structured in accordance with certain embodiments of the invention.

FIG. 30B is a sectional view taken along A-A of FIG. 30A.

FIG. 30C is sectional view taken along B-B of FIG. 30A.

DESCRIPTION

Figure 1:
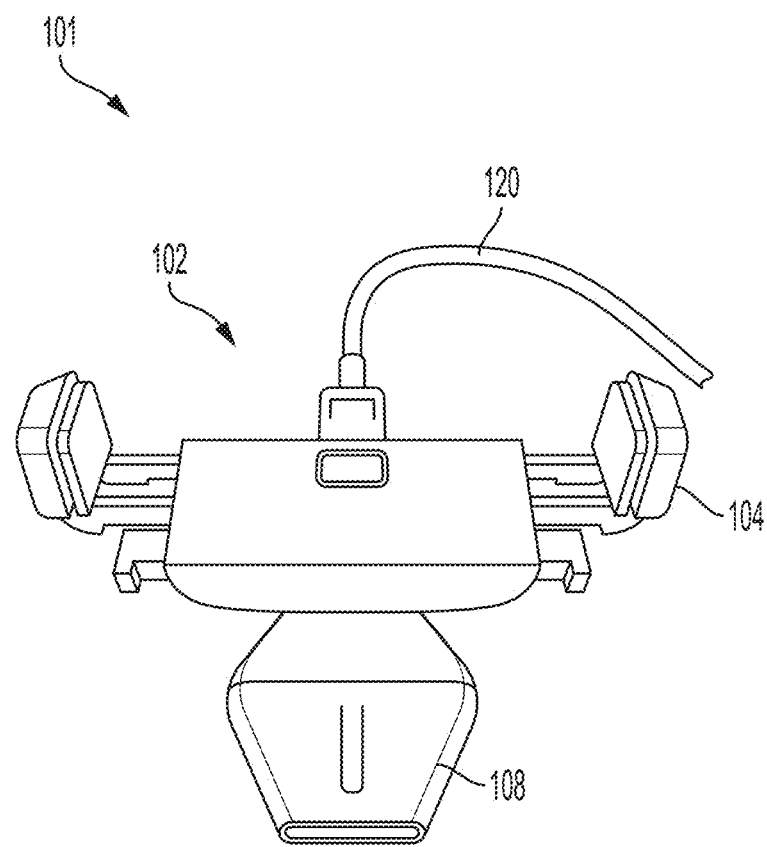
FIG. 1 schematically illustrates an example of a vascular guidance system structured in accordance with certain embodiments of the invention.

Many medical and veterinarian procedures and treatments are often aided by imaging apparatus and devices. Such procedures and treatments may include, for example and without limitation, biopsies, drainage of fluid collections from the body cavities or organs, perfusions, infusions, soft tissue injections, nerve block injections, placement of tubes or catheters within the organs, body cavities, or the vascular system, as well as diagnosing normal and pathologic conditions. The ability to use portable, real-time, single hand use, direct line of sight, 360-degree image acquisition and guidance can have a significant impact on a patient's treatment and well-being. Such procedures need to be performed in efficient ways that reduce or eliminate opportunities for human error whenever possible. For example, identifying an appropriate blood vessel that is suitable for a desired infusion or treatment and successfully accessing the selected vessel is often an essential element of a patient's treatment.

In various embodiments of the present invention, a point-of-care ultrasound (POCUS) guidance apparatus can be provided as a coupling device which provides single-hand use, direct line of sight imaging with 360° rotation of the display with respect to the ultrasound probe or other imaging apparatus. The display may also be positioned in either portrait or landscape configuration and the angle adjusted for optimal viewing during procedure performance. The guidance apparatus can be embodied as a device which is inclusive of, or provides a means of coupling, an imaging modality including but not limited to ultrasound, x-ray and ultraviolet light; and a display, as a single unit which provides real-time, portable, single hand use, direct line of sight, three hundred-and sixty degrees image acquisition for medical and veterinarian diagnostic and therapeutic procedures. For example, the device can facilitate the identification of an organ or selected tissue, its morphology and recognition of pathology. It can provide information regarding the depth of the organ or selected tissue, its pathologic condition, and also allow the user to evaluate the optimal angle of approach if an invasive procedure is performed. In addition, embodiments of the present invention can assist in the evaluation of adjacent or overlying structures that could lead to complications in the diagnosis and/or procedure performance. The device may be connected, wired or wirelessly, to a mobile device or other types of computing devices for the purposes of accessing display functions of the mobile device. Non-limiting examples of suitable mobile display devices include mobile phones, smart phones, tablets, graphic display enabled eyeglasses or goggles, wristband computing devices, or other devices which have a screen display capable of effective use with the imaging modality.

In certain embodiments, the guidance apparatus can be configured to work in conjunction with a computer-based software application programed to facilitate performance of diagnostic and intervention procedures. The software application may enhance image acquisition, organ identification, pathology recognition, appropriate treatment selection as well as facilitate the performance of invasive procedures including but not limited to those listed above. In addition, the guidance apparatus and/or the computer software application can be used in conjunction with multiple types of training simulation devices to facilitate the training of medical and veterinarian professionals in performing both diagnostic and interventional procedures (e.g., vascular access procedures).

In various embodiments, only a single hand of a user is required to perform diagnostic imaging with a direct line of sight display, which facilitates identification of organs or tissue of interest, adjacent structures and associated pathology, thus aiding the performance of diagnostic and therapeutic procedures. In one example, placement of a hypodermic needle into a selected vessel of arm of a patient can be aided by the guidance apparatus. The significant benefits of a single-hand, direct line of sight mechanism for performing diagnostic and therapeutic imaging, including but not limited to vascular access, will be readily apparent to those skilled in the art. In certain embodiments, the guidance apparatus may also be used to power ancillary functions such as central pressure and blood chemistry, among others. Also, sterile peel and stick membrane barriers may be employed with the apparatus for infection control during diagnostic and therapeutic procedures, for example.

In various embodiments, a software application may be used with the guidance apparatus which can facilitate organ or tissue evaluation, appropriate procedure selection and successful performance using feedback and scoring mechanisms. In the example of vascular access, using the apparatus in conjunction with an application may be used to perform one or more of the following tasks: appropriate vessel identification, assessment of the identified vessel's depth from the skin surface, or lumen diameter and wall morphology, among others. This information can inform the user regarding factors such as optimal needle gage, angle of approach, infusion rate, and appropriateness of the vessel for the intended therapy, among others. The software application may be used to analyze diagnostic and therapeutic procedures for appropriateness per accepted guidelines, for example, or to assist in the performance of a medical procedure and to document its successful completion.

In various aspects of the present invention, a guidance system is provided for guiding a practitioner in association with various types of medical procedures, including needle or probe insertion procedures involving different vessels or tissues of a human or animal patient, for example. The guidance system may comprise a guidance device including a clamping mechanism portion and an imaging apparatus, among other elements. The clamping mechanism can be structured to secure one or more kinds of hand-held mobile devices, which provide a screen display for displaying images during performance of the medical procedure using the guidance system. Accordingly, the guidance system can be designed for manual manipulation in a single hand of a user, freeing the other hand of the user to perform an injection procedure into a vessel or body tissue, for example. In certain embodiments, a computer-based or software-based vascular assessment tool can be provided which may be downloaded or installed for use on the mobile device. The vascular assessment tool can leverage a scoring system to determine how and under what optimum circumstances a medical procedure involving injecting a needle or probe, for example, should be performed for a patient. In other aspects, the vascular access guidance system and/or the vascular assessment tool may be applied in the context of certain training devices and educational tools described herein.

In certain embodiments, the apparatus is configured to incorporate an imaging modality, such as an ultrasound imaging probe, and a display into a single integrated unit which facilitates single hand use, direct line of sight guidance for vascular access and other procedures, providing depth of target and optimal angles of approach for vascular access, for example. The guidance device may be structured to be hand-held and effectively manipulated by a single hand of a user, such as a physician, nurse, or other medical professional. The guidance device may be programmed for use with ultrasound, ultraviolet, X-ray, and other types of imaging technologies. The guidance device may be attached or connected to a mobile device or other types of computing devices for purposes of accessing display functions of the mobile device. Examples of suitable mobile devices may include mobile phones, smartphones, tablets, graphic display enabled eyeglasses, wrist-band computing devices, or other devices which have a screen display capable of effective use with the guidance device.

In certain embodiments, the guidance device can be configured to work in conjunction with a computer-based software application which is programmed to facilitate detailed patient evaluation for vascular access or other diagnostic or therapeutic procedures. The software application may implement an enhanced assessment process and real-time feedback regarding vessel appropriateness to evaluate the desired access, procedure, or other use. The direct line of sight guidance provided by the application can be used for many different types of procedures, including drainage, biopsies, perfusions, infusions, injections, nerve block injections, tubes for spine treatment, and other medical procedures and treatments. In addition, certain embodiments of the device and/or the software application can be used in conjunction with different kinds of training simulators or training devices to facilitate training for medical professionals, for example, who need to perform vascular access procedures on patients.

FIGS. 1 through 4 illustrate an example of a vascular access guidance system 101 structured in accordance with various embodiments of the invention. In this example, a guidance device 102 includes a clamping mechanism 104 structured to expand or retract as appropriate to receive and secure a mobile device 106 therein having a display screen 106A. It can be appreciated that the adjustability of the clamping mechanism 104 allows the guidance device 102 to accommodate a variety of different shapes and sizes of mobile devices 106. The guidance device 102 can function as an imaging apparatus by virtue of an imaging head 108 which employs ultrasound technology (or another suitable imaging technology) and which can be applied to the skin surface of a patient (e.g., arm, leg, back, or other body part of the patient). The imaging head 108 may incorporate one or more transducers to perform the functions of an imaging apparatus.

In certain embodiments, the imaging head 108 may be operatively associated with a swivel mounting 110 configured for permitting rotatable movement of the imaging head 108 with respect to the display component, and thereby allowing documentation of needle tip position within a vessel or other body part of a patient, for example. The swivel mounting 110 may include an adjustable rotating ball, mechanical gear, ball-and-socket arrangement, or other swivel mechanism to facilitate turning and then holding the imaging head 108 in place during a medical procedure. In certain embodiments, the swivel mounting 110 may be configured to permit the imaging head 108 to be articulated in a range of motion of 0 to 360 degrees, for example, around the swivel mounting 110. The swivel mounting 110 also facilitates enhanced storage and portability capability for the guidance device 102. In certain embodiments, the swivel mounting 110 may operate as a quick connect/disconnect means for replacement of the imaging head 108, for example, and the transducer components contained therein.

Figure 2:
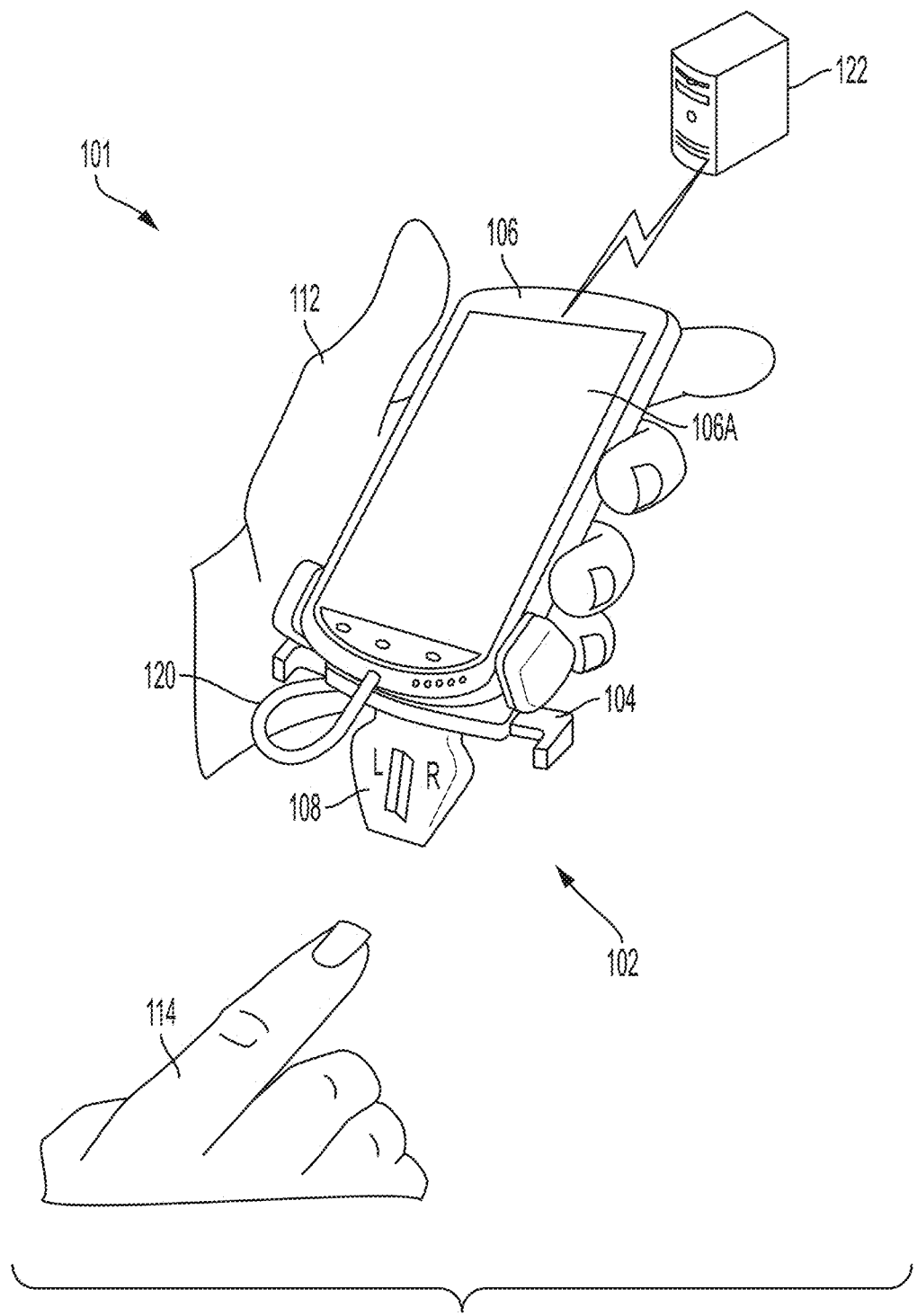
FIG. 2 shows the vascular guidance system of FIG. 1 held in the hand of a user.
Figure 3:
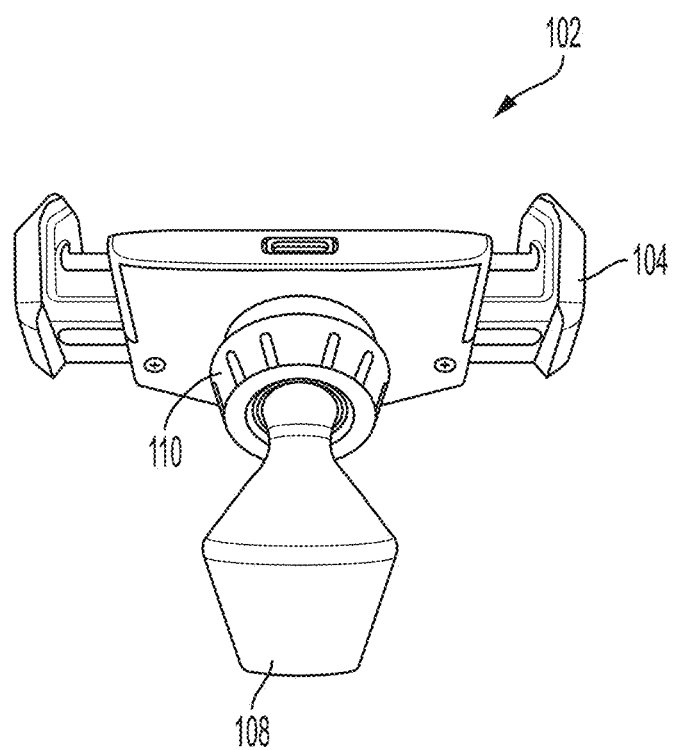
FIG. 3 displays another view of the vascular guidance system of FIG. 1.
Figure 4:
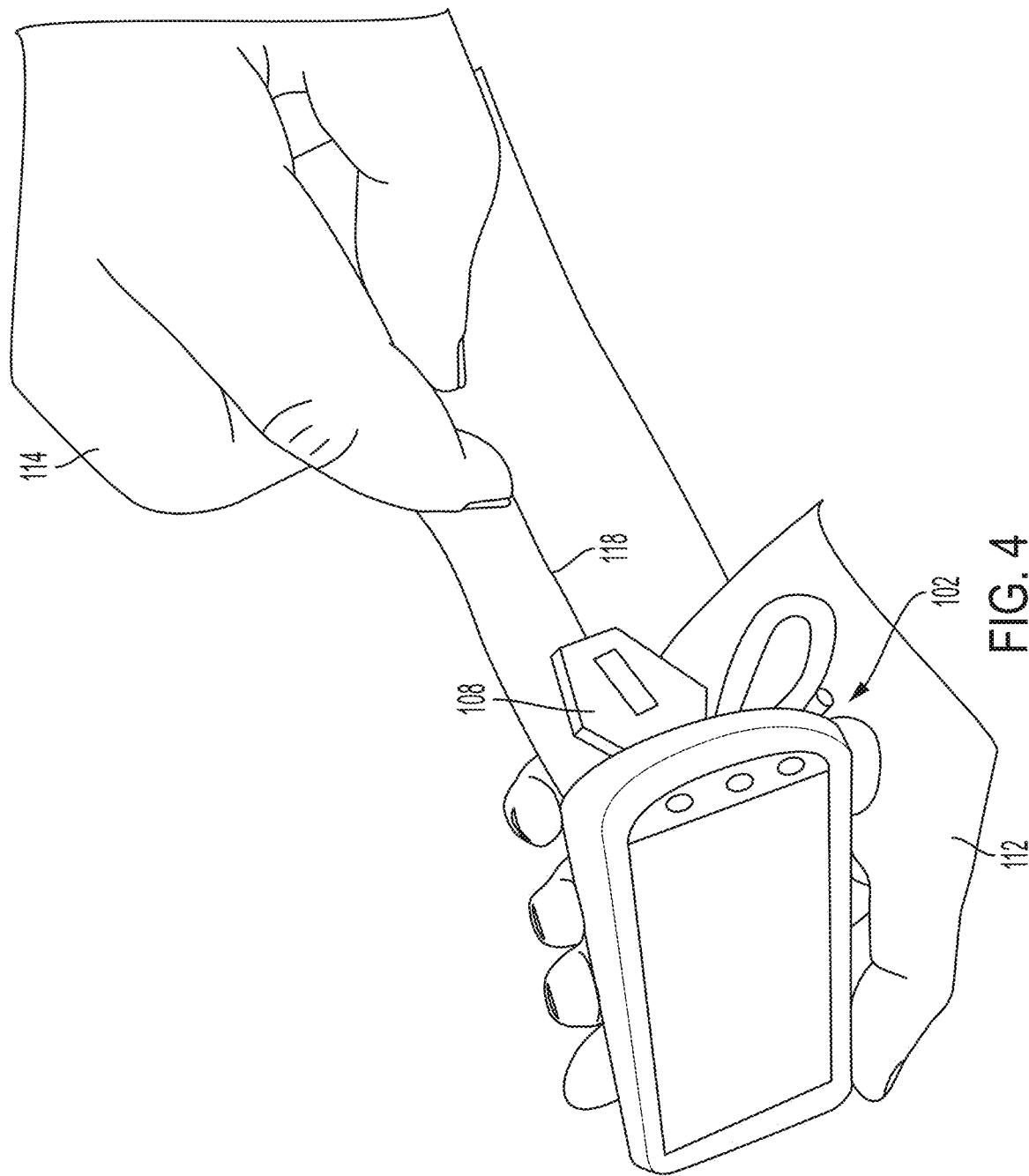
FIG. 4 schematically illustrates an example of a vascular guidance system structured in accordance with certain embodiments of the invention in use during a needle insertion medical procedure.

With particular reference to FIG. 2, the guidance device 102 is ergonomically designed for effective and convenient single left-hand 112 (as shown in this example) or single right-hand 114 use. FIG. 4 illustrates an example of the guidance device 102 employed in the left hand 112 of a user in association with applying the imaging head 108 to the surface of a patient arm 116. In this manner, only a single hand 112 of the user is required to locate and identify potential blood vessels for insertion of a hypodermic needle 118 by the right hand 114 of the user, for example. The important benefits of this single hand, direct line of sight approach for performing multiple vascular and blood testing functions will be readily apparent to those skilled in the art.

In certain embodiments, a communication cable 120 serves to enable data communications, power transmission, and other electrical functions between the imaging head 108 and the mobile device 106 and its screen display 106A. The imaging head 108 and its associated transducer components may be powered by the mobile device 106. In other embodiments, an accessory battery may be provided as a power supply to charge an internal battery of the device 106 which may also be used to power ancillary functions such as Central Venous Pressure and "iStat" blood chemistry functions, among others.

Figure 5:
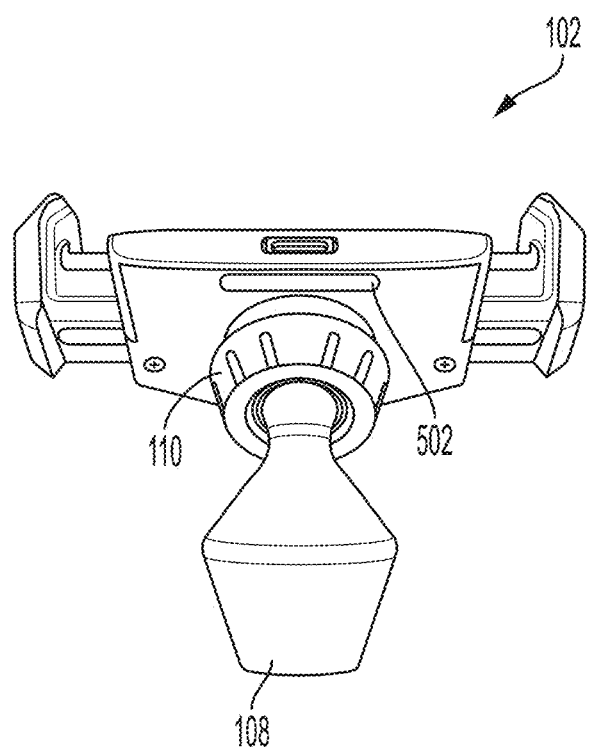
FIG. 5 schematically illustrates another example of a vascular guidance system structured in accordance with certain embodiments of the invention.

FIG. 5 illustrates another embodiment of the guidance device 102 in which a dial 502 can be rotated by the hand of a user to manipulate the position of the imaging head 108 within the swivel mounting 110. In certain embodiments, peel-and-stick membranes can be employed in connection with the guidance device 102 for single-use necessities (e.g., for infections like C-diff, etc.)

In various embodiments, a software application can be provided as a scoring and feedback tool for assessment and evaluation of vascular access and to suggest appropriate medical treatment. The application may be used to perform one or more of the following tasks: identify the vessel for venous access; measure the identified vessel's diameter; recommend needle gauge for the identified vessel; recommend maximum infusion rate for the identified vessel; advise on compatibility of the intended infusion medium with the selected vessel; determine the distance, penetration angle, and depth for needle placement. An example of the process flow of the software application illustrating various information collection, analysis, and other tasks performed by the application is included in Exhibit A (see below).

In various embodiments, the software application may be used or reside on any computing device, including mobile devices 106. The software application may be programmed for connectivity to an ultrasound apparatus, other imaging devices, computer systems 122, or other computing devices using Bluetooth, WiFi, NFC, or others, for reporting purposes, statistical analyses, training reviews, medical records audits, etc. (application output and results may be scored, aggregated, statistically analyzed, used for training purposes, etc.) The application may include education, training and reference materials for professional use and advancement, including certifications. The application may be linked to one or more computer processing devices through wireless or wired means, and/or to cloud computing architecture for directing medical procedures, for performing data storage and retrieval, and/or for other purposes.

The software application may be programmed to analyze vascular access and facilitate patient treatment through veins and/or arteries as well as organs, bones, soft tissue (e.g., cartilage) among other portions of an animal or human body. The application can be embodied as a decision tool, multi-variable interactive, and possessing adaptive learning capabilities. Also, the application is a multipurpose, real-time, biometric tool that facilitates data collection and analysis for diagnostic labs (chemistries), blood gasses, core and other temperatures, and blood sugar values including but not limited to A1C. The software application can be used to calculate the size of a vessel and used to minimize occlusion risks to the vessel.

Figure 6:
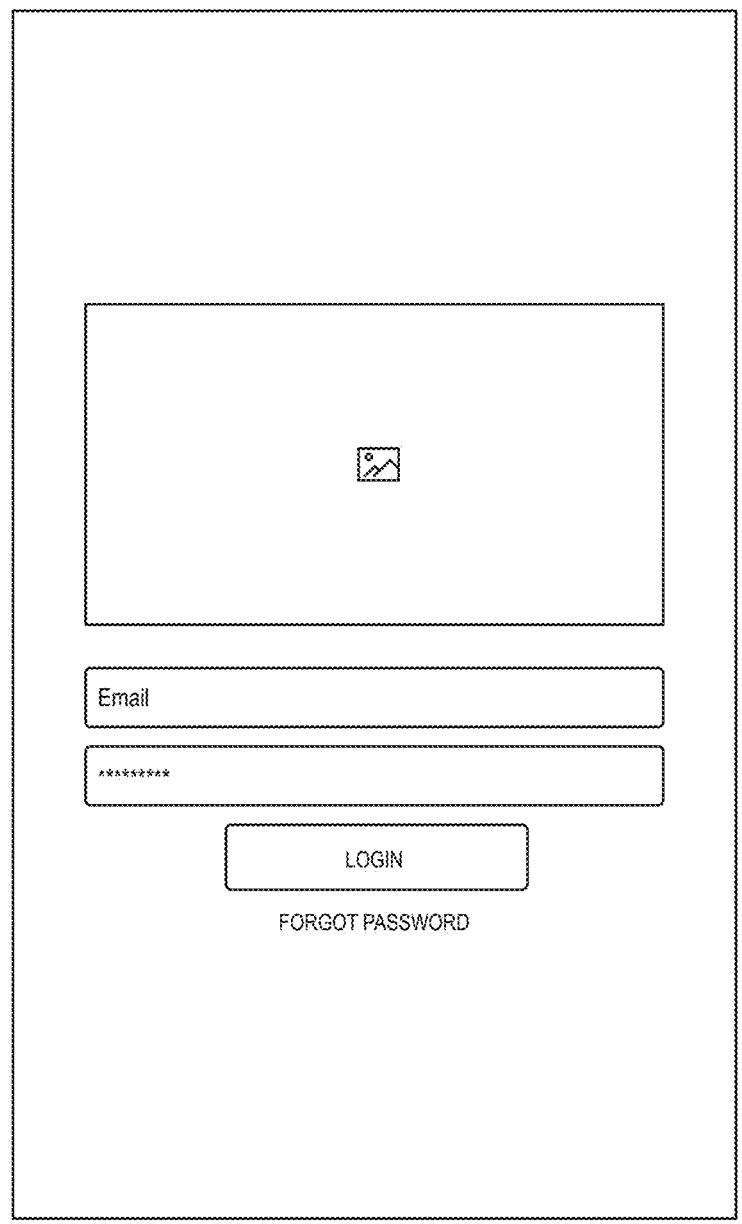
FIG. 6 displays an example of a graphical user interface accessible through a vascular assessment tool configured in accordance with certain embodiments of the invention.
Figure 7:
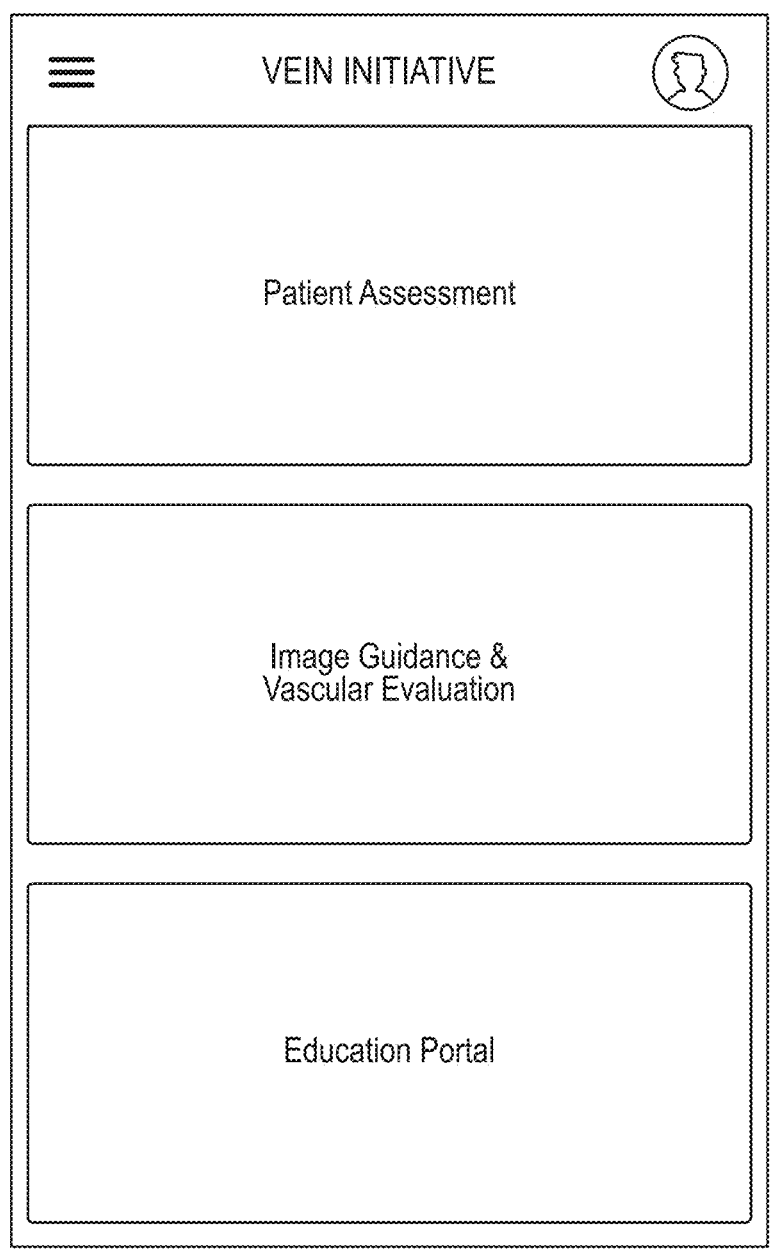
FIG. 7 displays an example of a graphical user interface accessible through a vascular assessment tool configured in accordance with certain embodiments of the invention.
Figure 8:
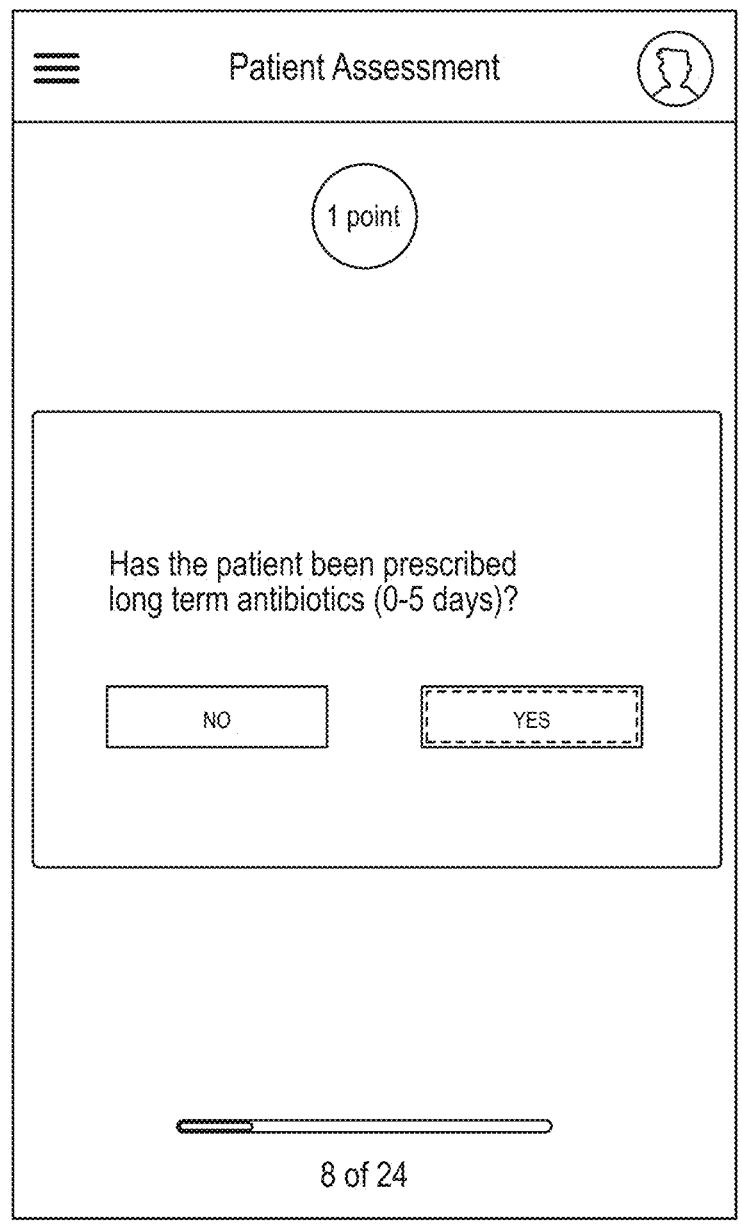
FIG. 8 displays an example of a graphical user interface accessible through a vascular assessment tool configured in accordance with certain embodiments of the invention.

FIGS. 6 through 9 include examples of user interface screens that may be presented to user on the mobile device 106, for example. FIG. 6 includes an example of a login screen for accessing the application. FIG. 7 includes an example of a portal screen programmed to provide access to a user to various portions of the application (e.g., patient assessment, image guidance and vascular evaluation, and an education portal). FIG. 8 displays an example of a screen display presented to the user upon accessing the patient assessment portion of the application.

Figure 9:
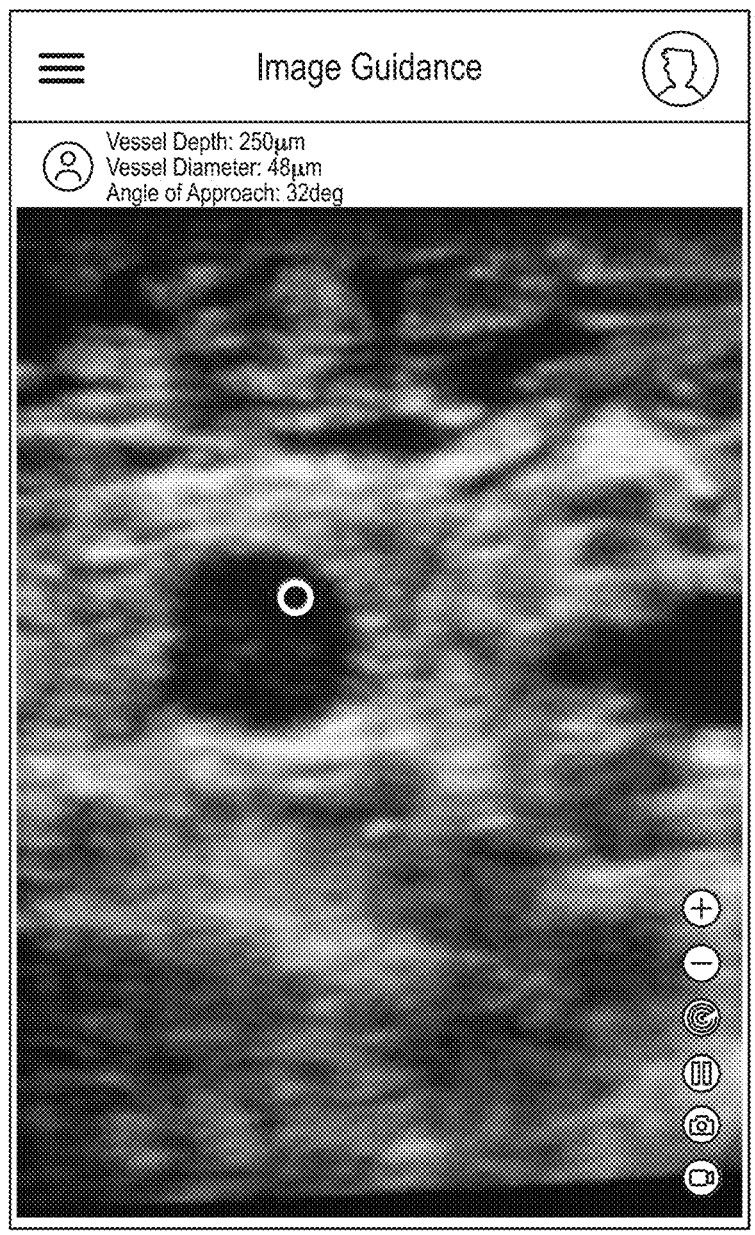
FIG. 9 includes an example of an image shown on the screen display of a mobile device employed in operative association with a vascular guidance system structured in accordance with certain embodiments of the invention.

FIG. 9 depicts an example of a screen display showing a vein ultrasound scan with medical descriptions included. It can be seen that after the image has been transferred to the application, with dimensions listed at the top of the screen display, a potential vascular insertion point (red circle can be superimposed on the display for guidance. It can be appreciated that the vascular insertion point may be part of a larger vessel or channel (e.g., blood vessel) in which the insertion point is displayed. Accordingly, the vascular insertion point may identify an ideal or target location for injection of a needle, for example, or it may be employed just as a reference point identifying the larger vessel or channel. In certain embodiments, the red circle may be instead displayed as a rectangle, triangle, hexagon, or another geometric shape.

Figure 10:
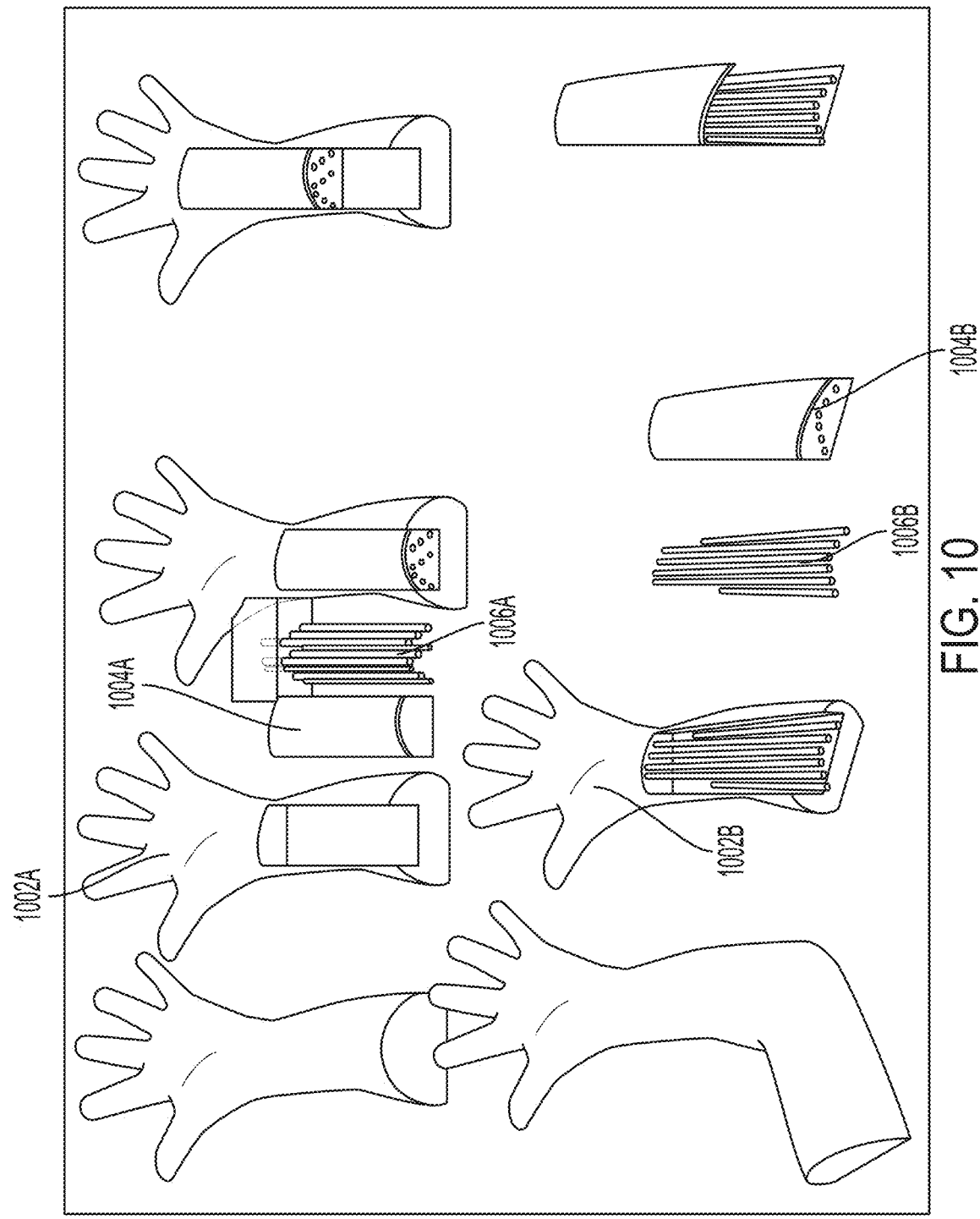
FIG. 10 schematically illustrates examples of various medical procedure training devices which can be used in connection with certain vascular guidance systems described herein.

With reference to FIG. 10, examples of training devices or training simulators 1002A, 1002B can be provided to enable users to practice using needle insertion into plastic sleeves or inserts 1004A, 1004B (in the shape of an arm) with synthetic disposable veins 1006A, 1006B of varying sizes contained therein. The simulators 1002 may be comprised of a rigid shell with replaceable training inserts 1006, which can be made of material that simulates the mechanical and ultrasound properties of animal tissue, for example. The simulators 1002 can be used to train medical and veterinarian professionals in locating, accessing, and safely inserting lines and other devices and/or solutions into the vascular system. They can be used for training for performing other diagnostic and therapeutic procedures including but not limited to biopsies and percutaneous drainage procedures. The simulators 1002 may also assist in training for selecting appropriately sized needles, catheters, vascular lines, as well other devices and/or solutions for therapeutic and diagnostic procedures.

The objective of the training simulator 1002 is to simulate the process of locating, accessing, and inserting needles, catheters, devices and/or solutions into the vascular system and performance other diagnostic and therapeutic procedures including but not limited to biopsies and percutaneous drainage procedures such that medical and veterinarian professionals are prepared to perform these tasks safely and efficiently in the appropriate clinical setting.

The rigid shell can be modeled from data obtained from a CT or MRI scan of human or animal anatomy in a way that simulates a desired anatomic location, organ, or organ system. The training insert 1004 can be designed to simulate the mechanical and ultrasound properties of the desired organic tissue and may contain objects or channels of varying sizes, shapes and depths which may be filled with fluid to assist in training medical and veterinarian professionals in locating, accessing, and inserting vascular lines and other devices and solutions into the vascular system or body part. The simulators 1002 may also contain other materials or targets to assist in training medical and veterinarian professionals with other diagnostic and therapeutic procedures including, but not limited to, biopsies and percutaneous drainage procedures.

With respect to the example of a human forearm simulator 1002 shown in FIG. 10, the rigid shell may be provided with a length of about 44 cm, and a width from about 12 cm to 19 cm. Each training insert 1004 may be structured with a length of about 24 cm, and a width in the range of about 6.5 cm to 9 cm. Each of the vascular channels 1006 may be structured with a diameter in the range of about 2.5 mm to 6 mm and positioned at a depth below the outer surface of the simulator 1002 in the range of about 5 mm to 25 mm.

It is expected that once a medical or veterinarian professional has proven technical proficiency using the described simulators 1002, the professional will significantly improve safe, successful performance of these skills in the appropriate clinical settings. In various embodiments, the simulators 1002 may be used independently of or in combination with different embodiments of the guidance device 102 described herein, as well as various embodiments of the software application described herein.

The training devices and simulators described herein can enable users to practice needle insertions into material (which may replicate human or other animal anatomies) which contains vascular channels of one or more sizes or other anatomic or non-atomic structures. The simulators may be composed of a rigid shell with replaceable training inserts comprised of material that simulate the mechanical and ultrasound and other imaging properties of animal tissue. Materials may be composed of material that will not significantly dehydrate over time and which have controllable hardness, echo, and elastographic properties. Such materials may be one or more types of materials created by Lazarus 3D Inc. (Houston, Tex.) which are desired to replicate different kinds of biological tissue and pathology (vascular wall, subcutaneous, etc.).

In various embodiments, medical and veterinarian professionals may be trained in locating, accessing and safely inserting lines or other devices and/or solutions into the vascular, nervous or other systems. They can be used to train users for performing other diagnostic and therapeutic procedures, including but not limited to identifying pathologic conditions, biopsies and percutaneous drainage procedures. Simulators may also assist in training for appropriately sized needles, catheters, vascular lines and other devices and/or solutions for therapeutic and diagnostic procedures. Simulators may also be used for training of diagnostic imaging skills. Medical and veterinarian professionals are thereby prepared to perform these tasks safely and efficiently in appropriate clinical settings.

In various embodiments, the training devices may comprise a shell surrounding an arm, block, or mass modeled from data obtained from a CT, MRI or other multi-planar scan of human or animal anatomy in a manner that simulates a desired anatomic location, organ, or organ system. The training insert may be designed to simulate the mechanical, ultrasound or other imaging properties of the desired organic tissue and may contain channels, nodules or anatomy replicas of varying sizes and depths which may be filled with fluid or other substances to assist in training medical and veterinary professions in locating, accessing and inserting vascular lines and other devices and solutions into the vascular or other organ system. The simulators may also contain other materials or targets to assist in training medical and veterinary professions with other diagnostic and therapeutic procedures. Such procedures may include, for example and without limitation, identifying pathologic conditions and performing biopsies and percutaneous drainage procedures. The training device may also be 3D-printed to mimic the anatomy of a specific patient for practice treatment, surgery, or other organ or systemic purposes. Heat may be applied to renew device materials after use. In certain embodiments, the training device may employ needle detection technology or virtual reality schemes to proctor skill levels and skill testing through connection to a computing device.

Figure 11:
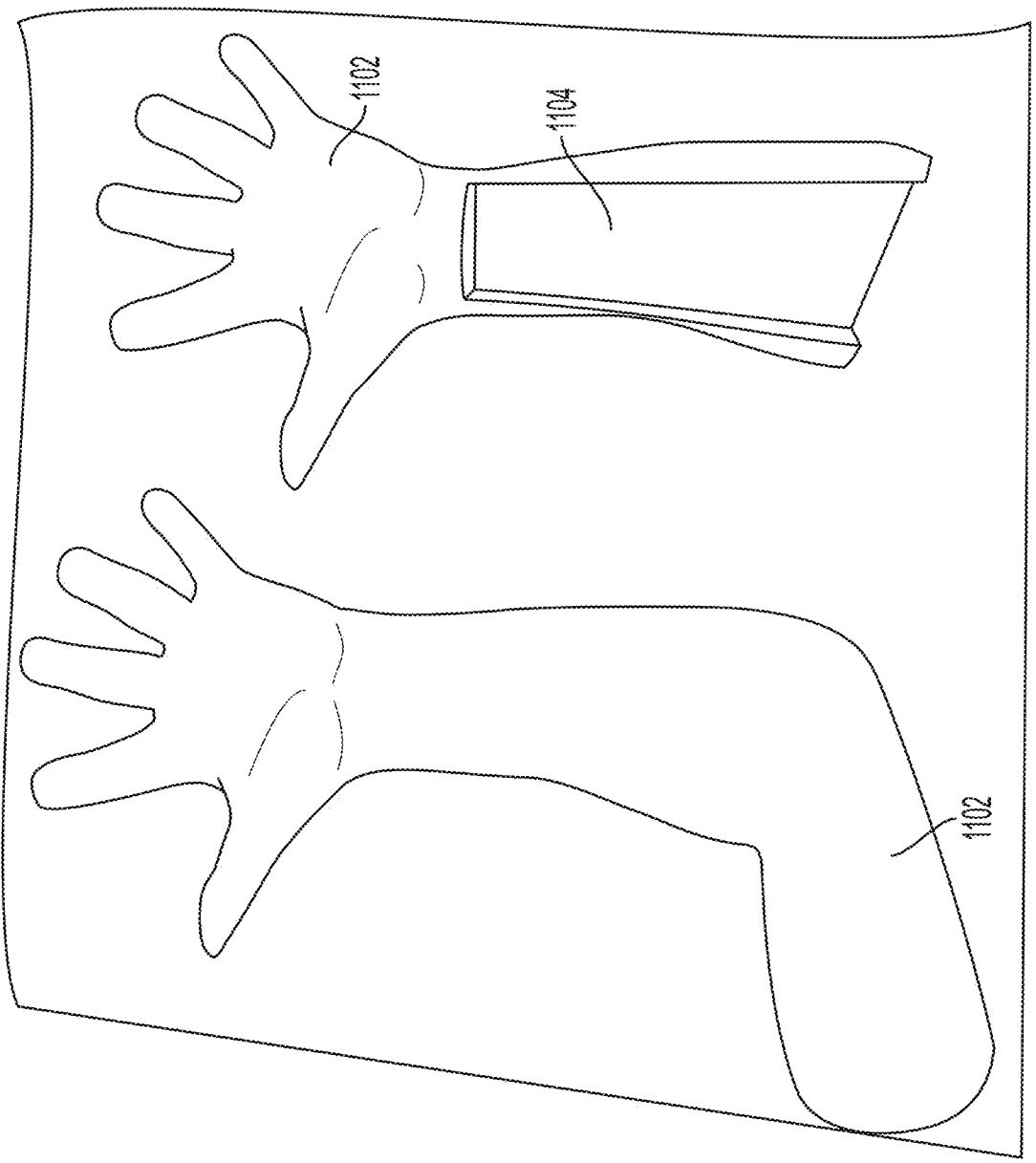
FIG. 11 schematically illustrates an example of a medical procedure training device which can be used in connection with certain vascular guidance systems described herein.
Figure 12:
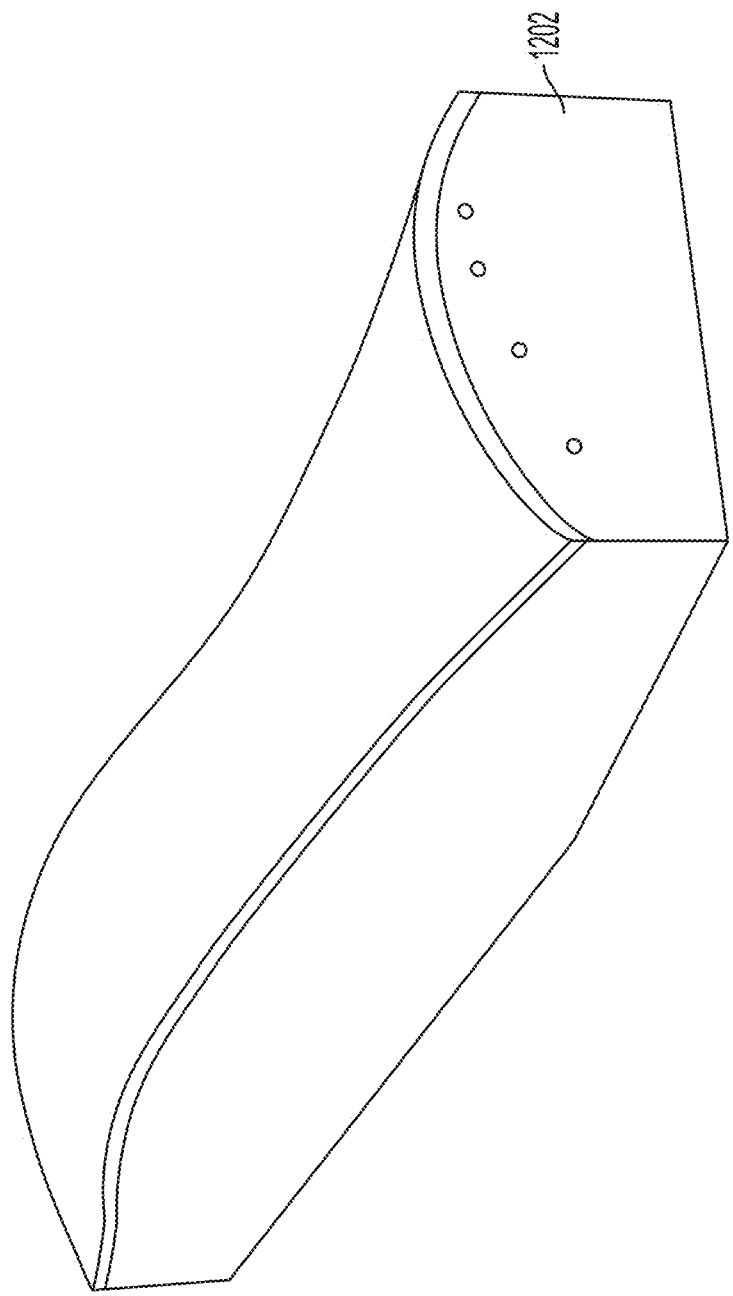
FIG. 12 schematically illustrates an example of an insert for a medical procedure training device used in connection with certain vascular guidance systems described herein.
Figure 13A:
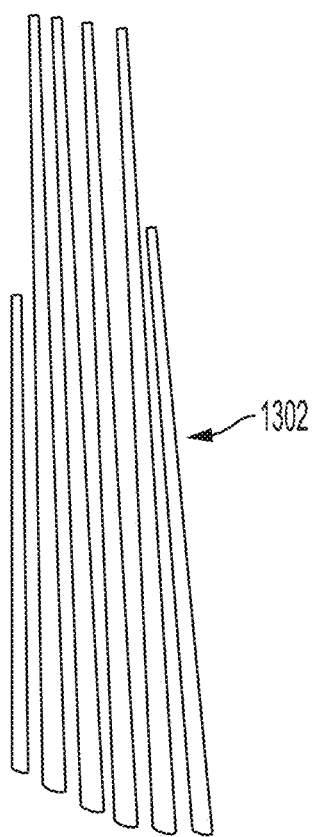
FIG. 13A schematically shows examples of different vessel structures which can be used in a medical procedure training device.
Figure 13B:
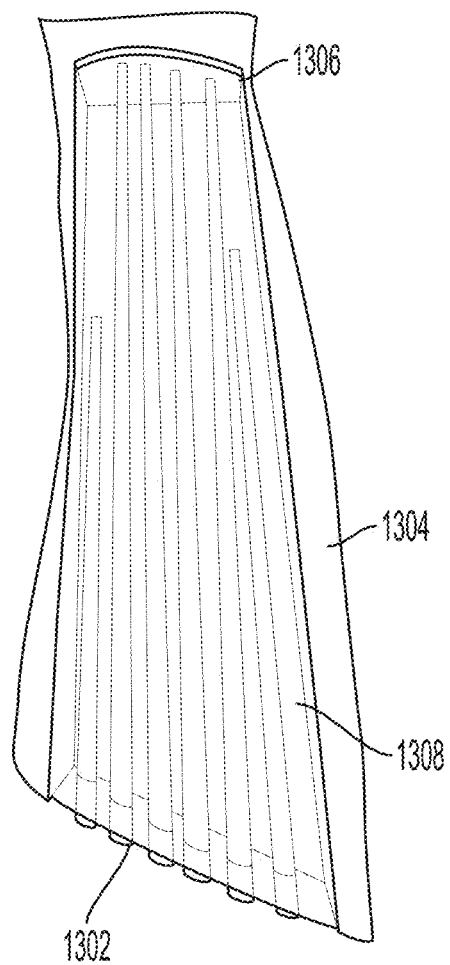
FIG. 13B depicts the vessel structures of FIG. 13A installed in a training device.

FIG. 11 schematically illustrates an example of a medical procedure training device 1102 which can be used in connection with certain vascular guidance systems described herein. The training device 1102 includes an insert 1104 suitable to receive simulated organic material therein. FIG. 12 schematically illustrates an example of an insert 1202 suitable for use in a training device used in connection with certain vascular guidance systems described herein. FIG. 13A schematically shows examples of different simulated vessel structures 1302 which can be used in a medical procedure training device 1304. FIG. 13B depicts the simulated vessel structures 1302 of FIG. 13A installed in an insert 1306 of the training device 1304. As shown, the simulated vessel structures 1302 may be embedded in a volume of simulated organic material 1308 residing within the insert 1306.

Figure 14A:
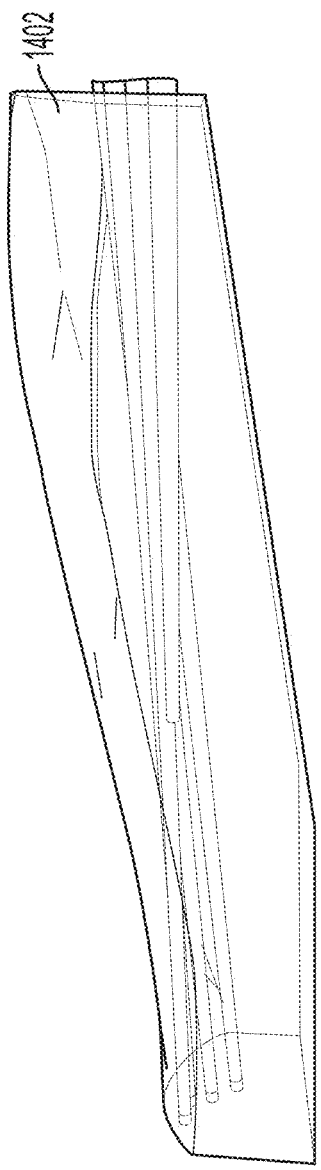
FIGS. 14A, 14B, and 15 show different views of an example of a medical procedure training device including vessel structures installed therein.
Figure 14B:
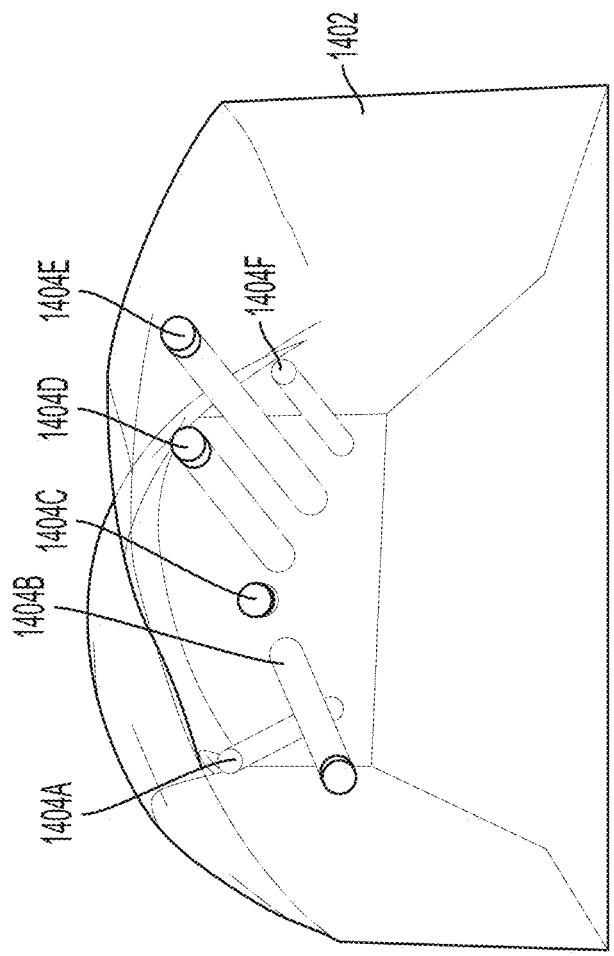
Figure 15:
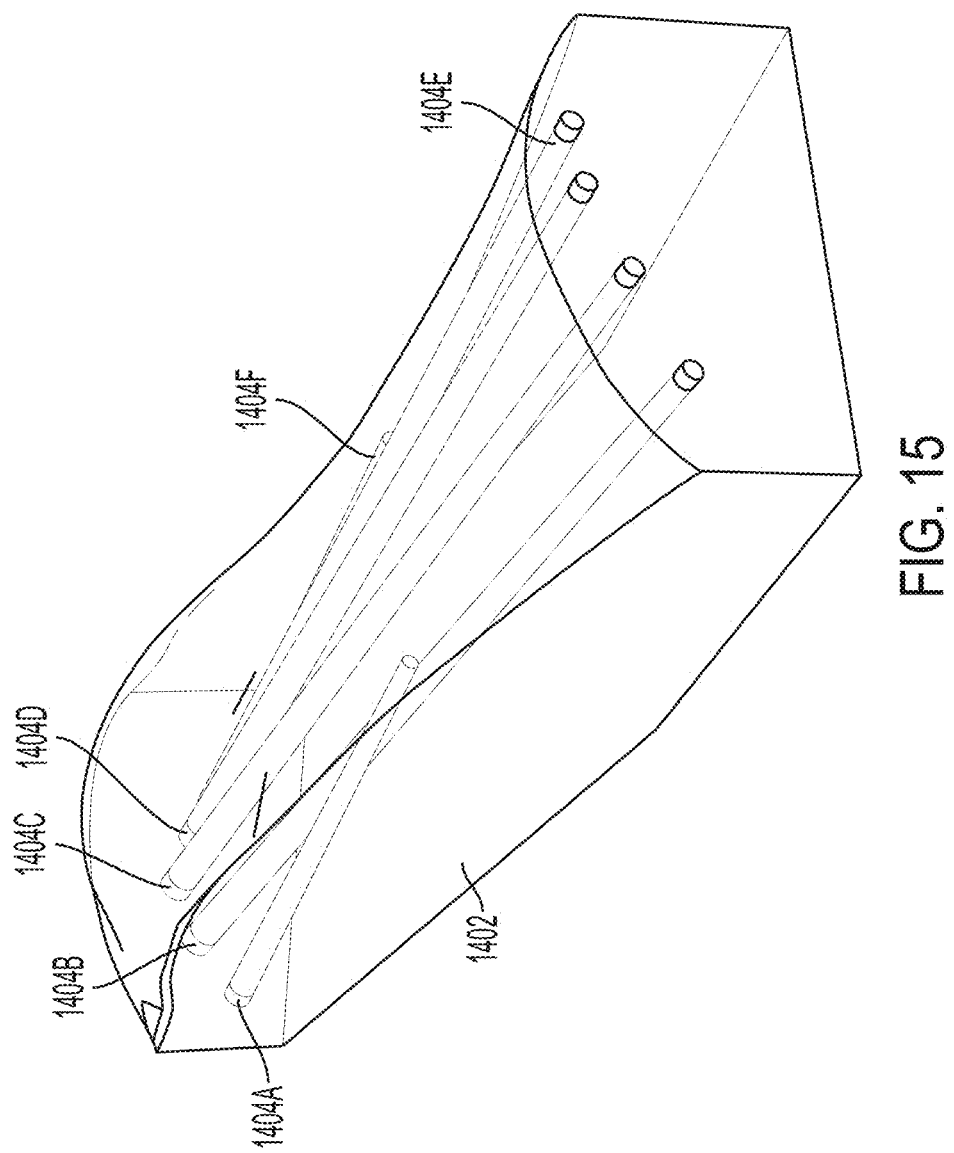

FIGS. 14A, 14B and 15 show different views of an example of an insert 1402 structured for use in a medical procedure training device. The insert 1402 may be composed of various kinds of simulated organic material (as described herein). In this example, various simulated vessel structures 1404A-1404F are shown extending through the insert 1402. In certain embodiments, the insert 1402 may comprise comparatively tougher skin on its top portion or outer surface and comparatively softer material below the comparatively tougher outer skin. The simulated vessels (e.g., veins) may taper from a comparatively smaller diameter (e.g., 2 mm) and enlarge as they extend medially through the insert 1402, reaching a maximum diameter of 6 mm. As shown, four vessels 1404B, 1404C, 1404D, 1404E are longer than two of the other vessels 1404A, 1404F which are positioned with a starting point midway through the insert 1402. Also, the vessels may take different paths through the insert 1402, perhaps starting at a depth of about 5 mm and ending at a depth of about 25 mm, in one example configuration.

Figure 15A:
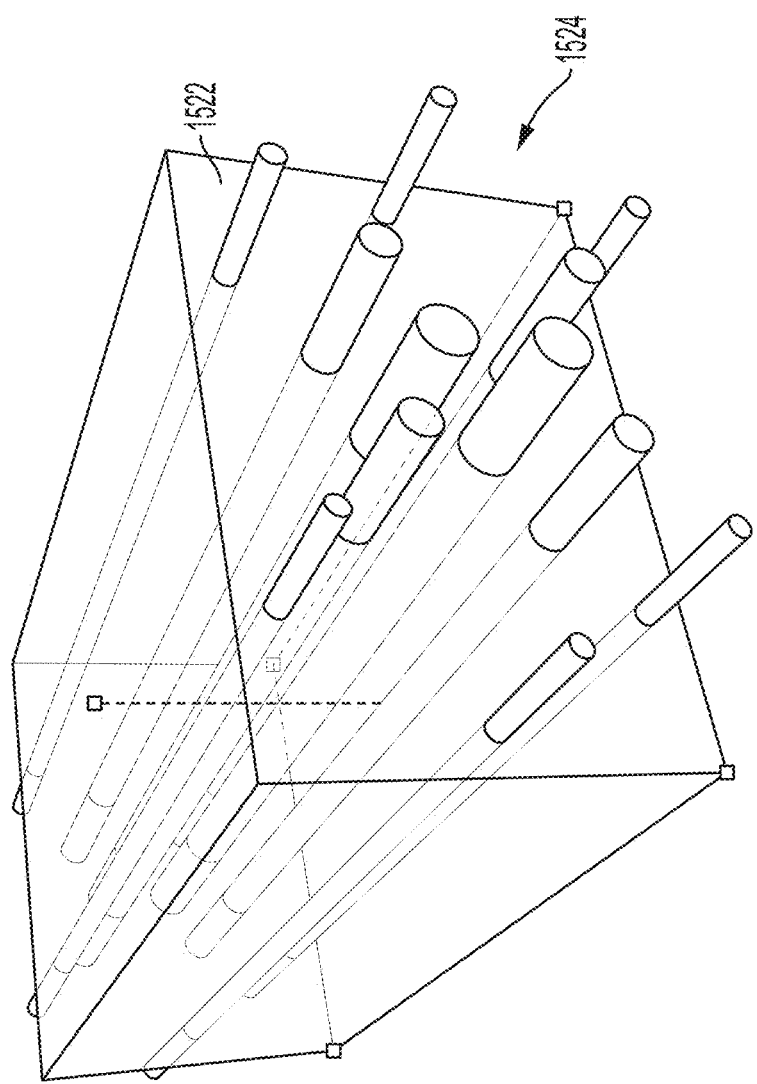
FIG. 15A shows another example of a medical procedure training device including vessel structures installed therein.
Figure 16:
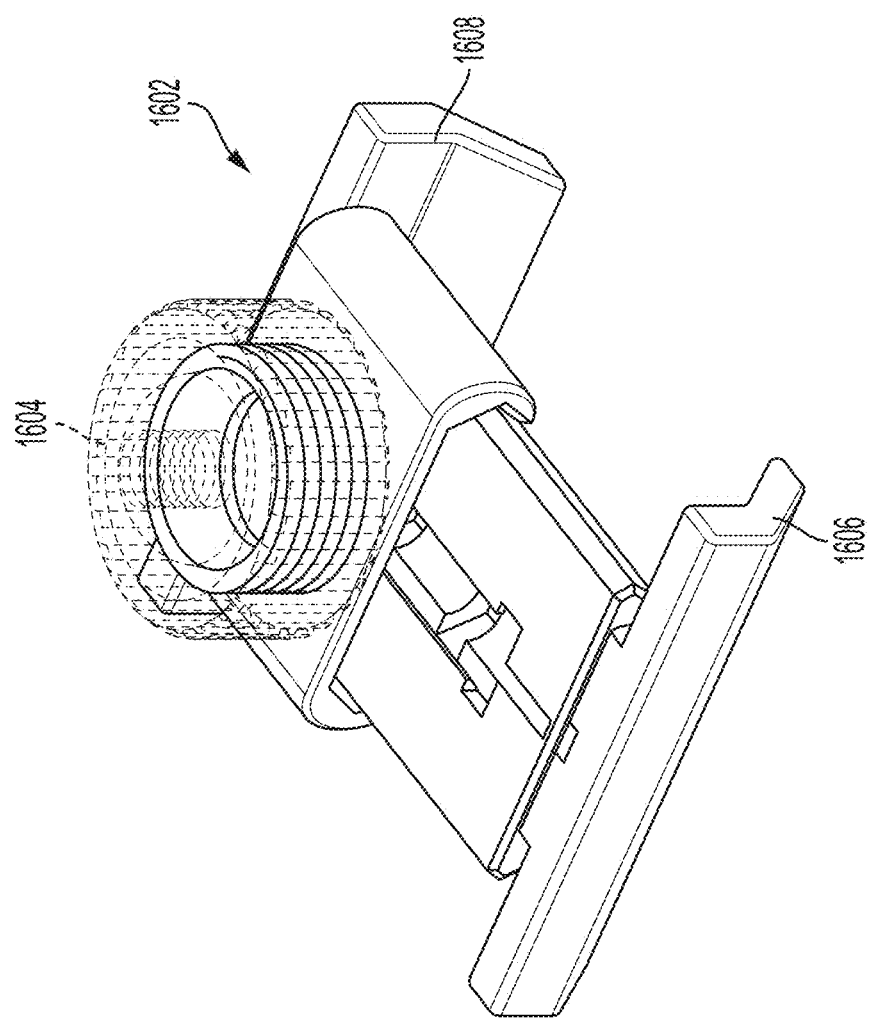
FIGS. 16 and 17 illustrate different views of an example of a clamping mechanism which can be used in accordance with certain embodiments of a vascular guidance system structured in accordance with various embodiments of the invention.
Figure 17:
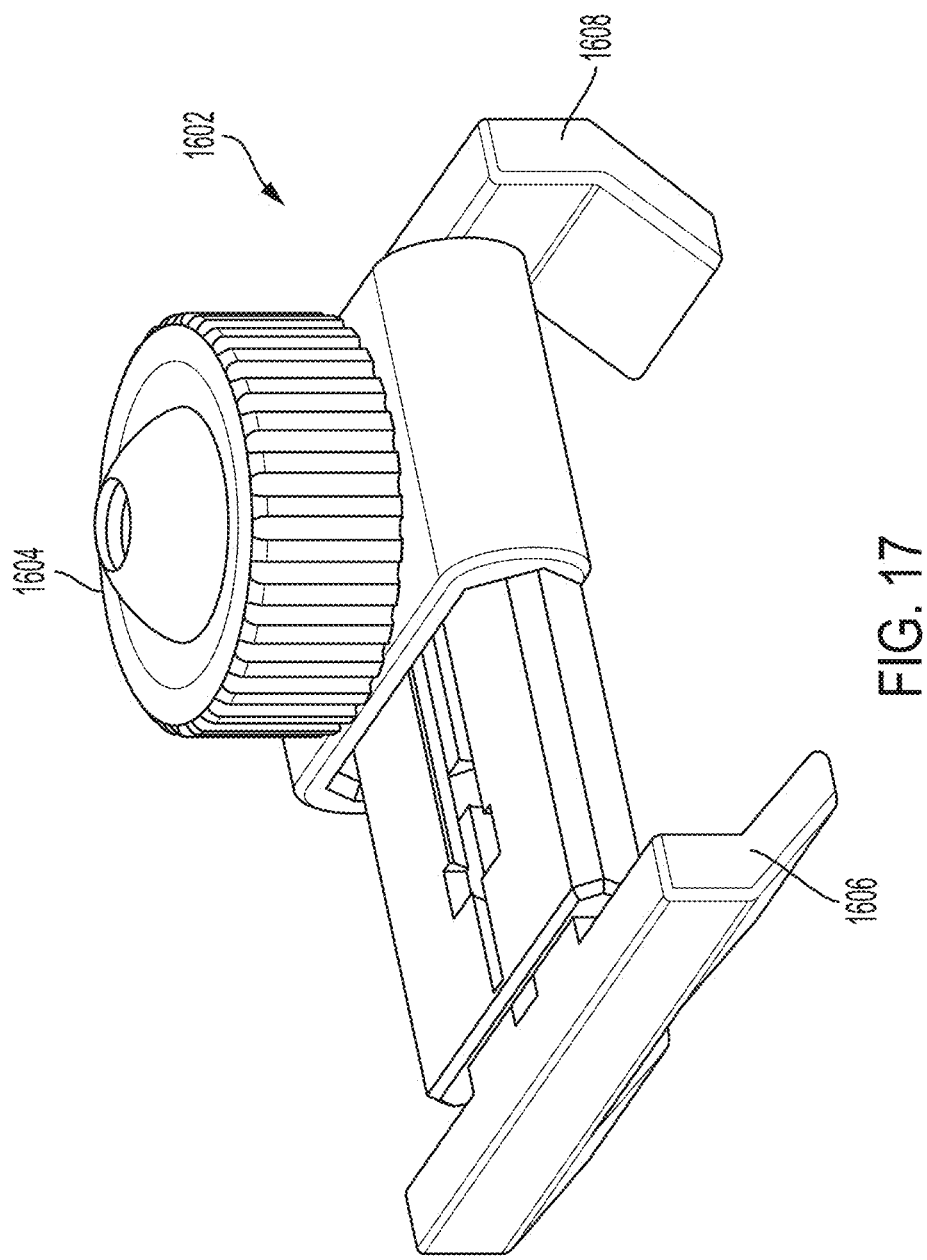

FIG. 15A shows another example of a medical procedure training device comprising a block-shaped insert 1522 including various vessel structures 1524 embedded therein. It can be appreciated that this example demonstrates that the training device need not be formed into any particular shape or form, such as in the shape of a body part, for example. A block of material can be sufficient FIGS. 16 and 17 illustrate different views of an example of a clamping mechanism 1602 which can be used in accordance with certain embodiments of a vascular guidance system structured in accordance with various embodiments of the invention. In this example, a dial 1604 communicatively coupled through a central axis of the mechanism 1602 can be alternately turned clockwise to cause legs 1606, 1608 to move closer toward each other, or counter-clockwise to cause legs 1606, 1608 to move farther apart from each other. In this manner, a mobile device (not shown) can be appropriately secured by or released from the mechanism 1602 by action of rotating the dial 1604 as appropriate.

Figure 18:
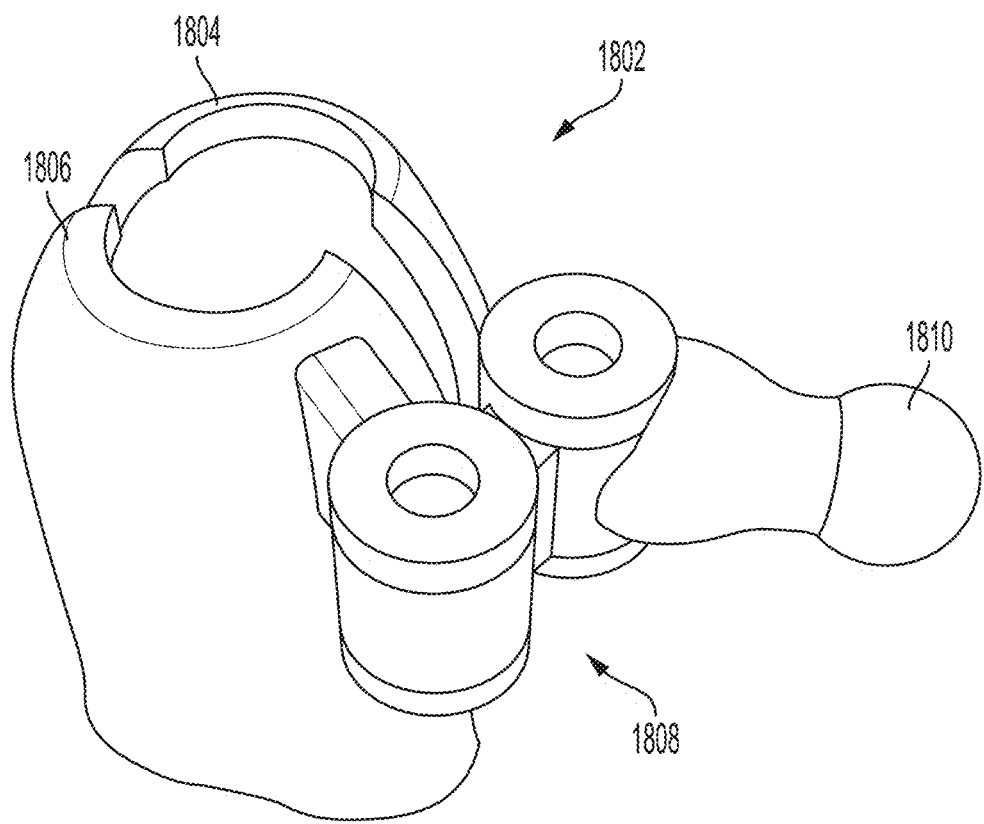
FIGS. 18 through 20 illustrate different views of an example of a cradle which can be used in accordance with certain embodiments of a vascular guidance system structured in accordance with various embodiments of the invention.
Figure 19:
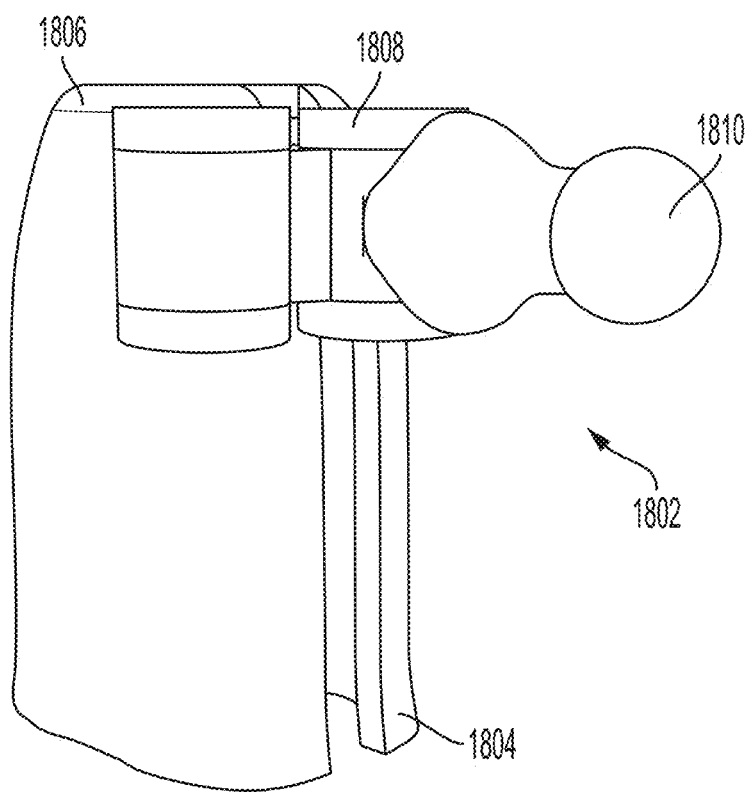
Figure 20:
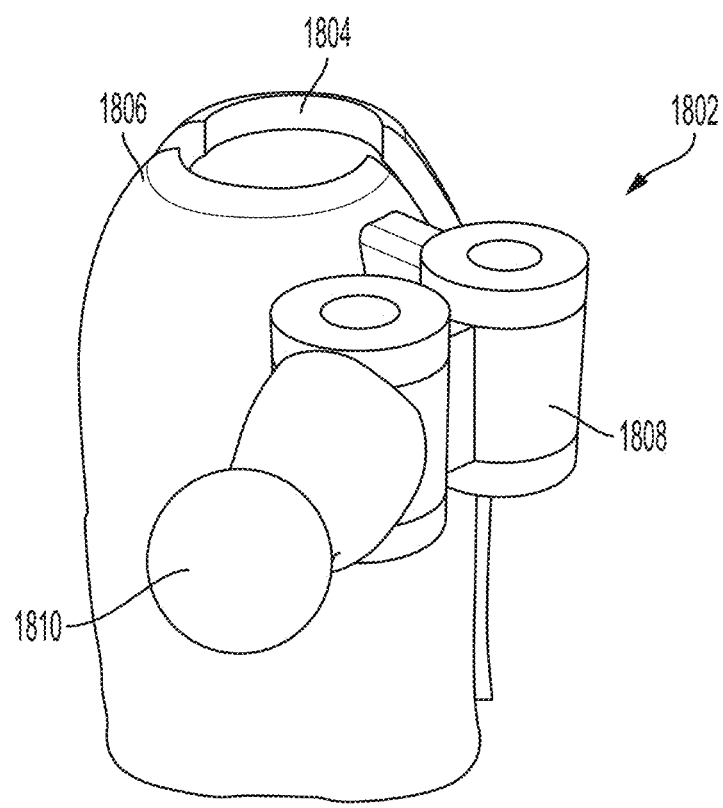
Figure 20A:
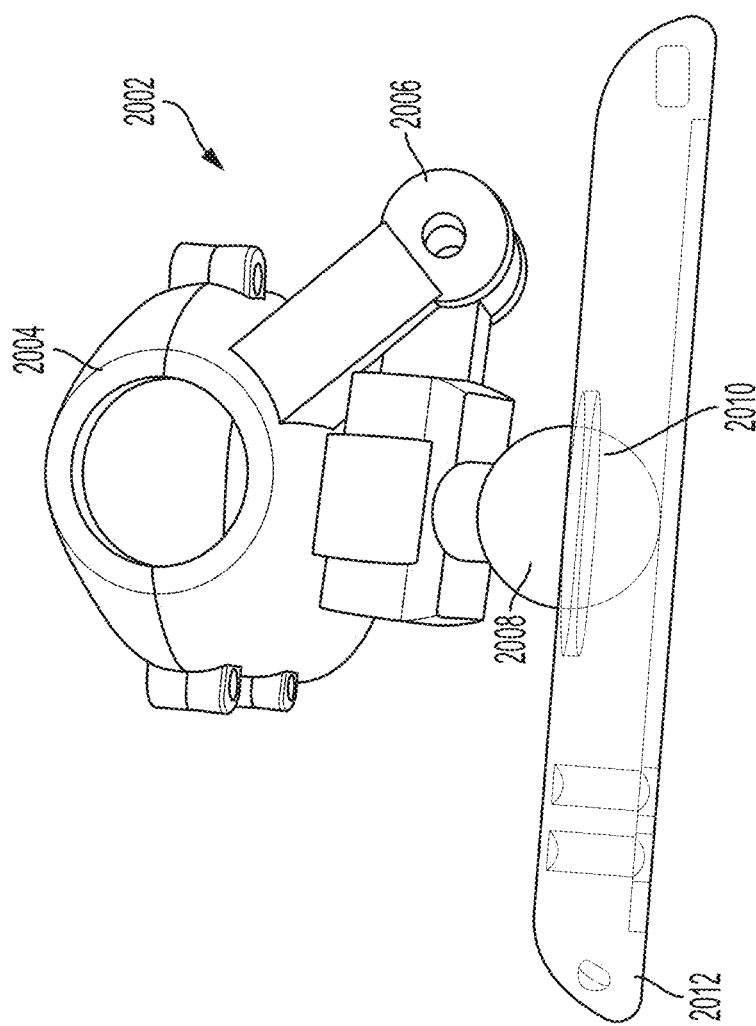
Figure 20C:
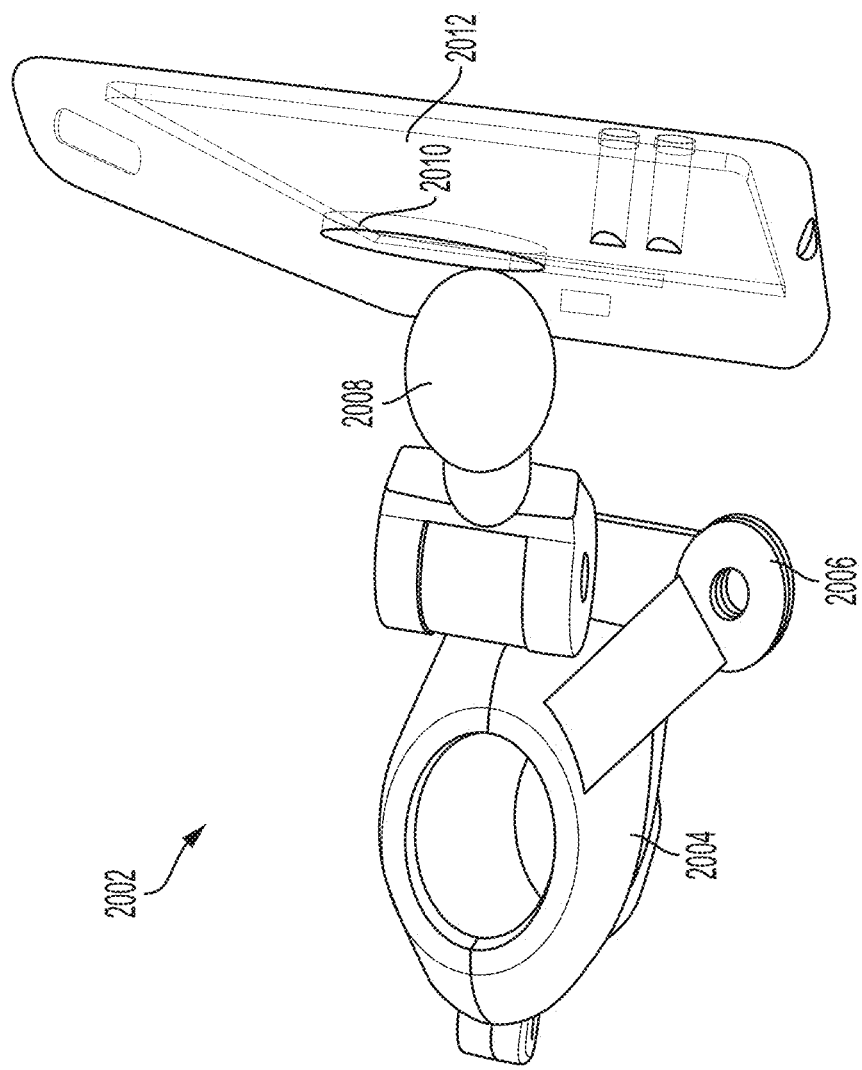
Figure 20D:
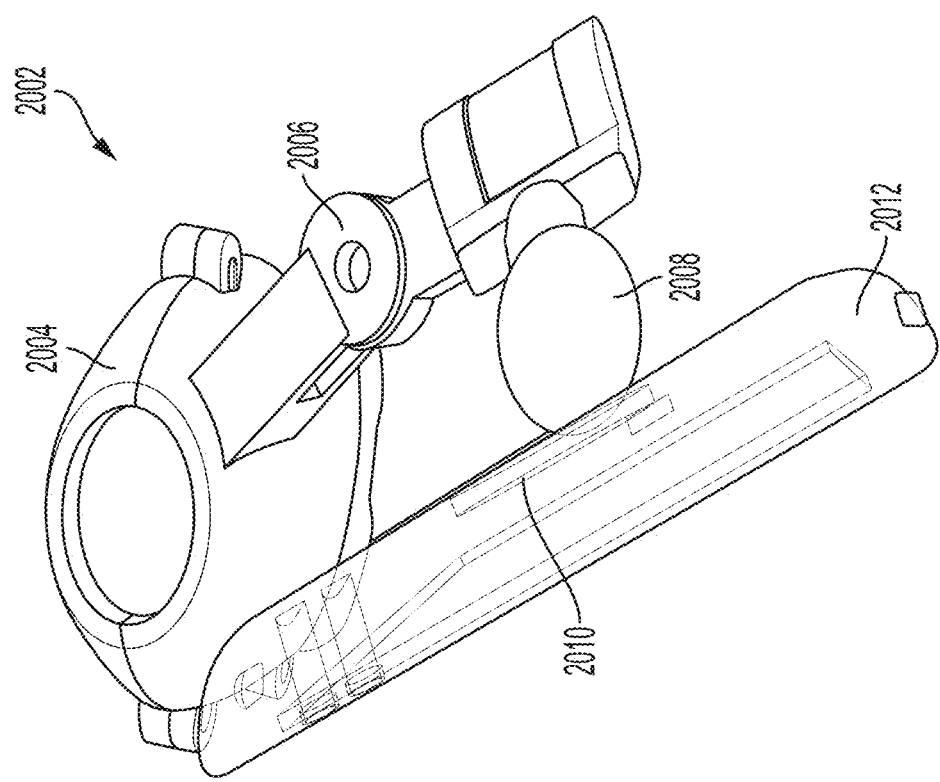

FIGS. 18 through 20 illustrate different views of another example of an imaging apparatus cradle 1802 (partially disassembled) which can be used in accordance with certain embodiments of a vascular guidance system structured in accordance with various embodiments of the invention. Two parts 1804, 1806 intended to form a cradle or enclosure can adhere in any suitable way, including via elastic, screws, latches, or a single piece via a snap fit, for example. The compound joint 1808 allows the imaging apparatus when positioned in the cradle (not shown) to be positioned so that the imaging apparatus can face either the broad or narrow side of the probe of an imaging apparatus, for example. A ball 1810 may be inserted securely but rotatably via friction into a suitable ball mount (not shown) which allows positioning of the imaging apparatus in various horizontal or vertical directions or other orientations. This adjustable cradle 1802 also permits up to 360 degrees rotation as well as display position and viewing angle adjustment of the imaging apparatus for direct line of sight visualization of a vascular access site, target organ, or imaging field of view. Interchangeable ultrasound or other visualization devices can be introduced into the adjustable (and perhaps pliable) cradle for use with vascular, small parts, obstetrical, orthopedic, dermatology and body/organ imaging components both in emergency and non-emergency settings.

FIGS. 20A through 20D illustrate different views of another example of an imaging apparatus cradle 2002 which can be used in accordance with certain embodiments of a guidance system structured in accordance with various embodiments of the invention. In this example, an enclosure 2004 of the cradle 2002 is comprised of two parts joined together at various locations by fasteners (e.g., screws). An articulable, jointed arm 2006 extends from the enclosure 2004, terminating at one end in a ball 2008. As shown, the ball 2008 is structured to be received into and secured within a socket 2010 of a mounting board 2012.

Figure 21:
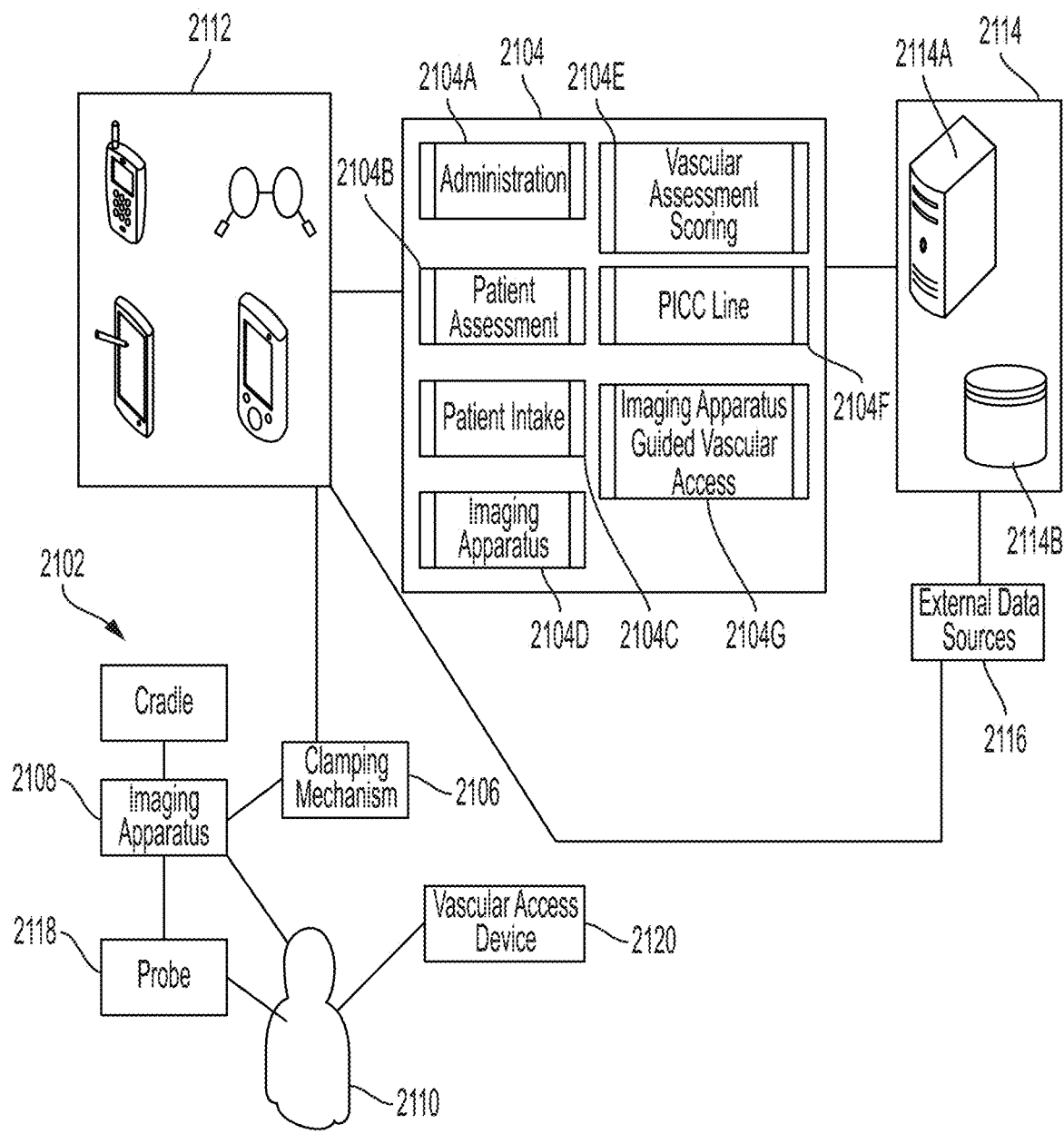
FIG. 21 schematically illustrates an example of a computer architecture and a process for use and operation of vascular guidance systems and vascular assessment tools structured in accordance with certain embodiments of the invention.
Figure 22:
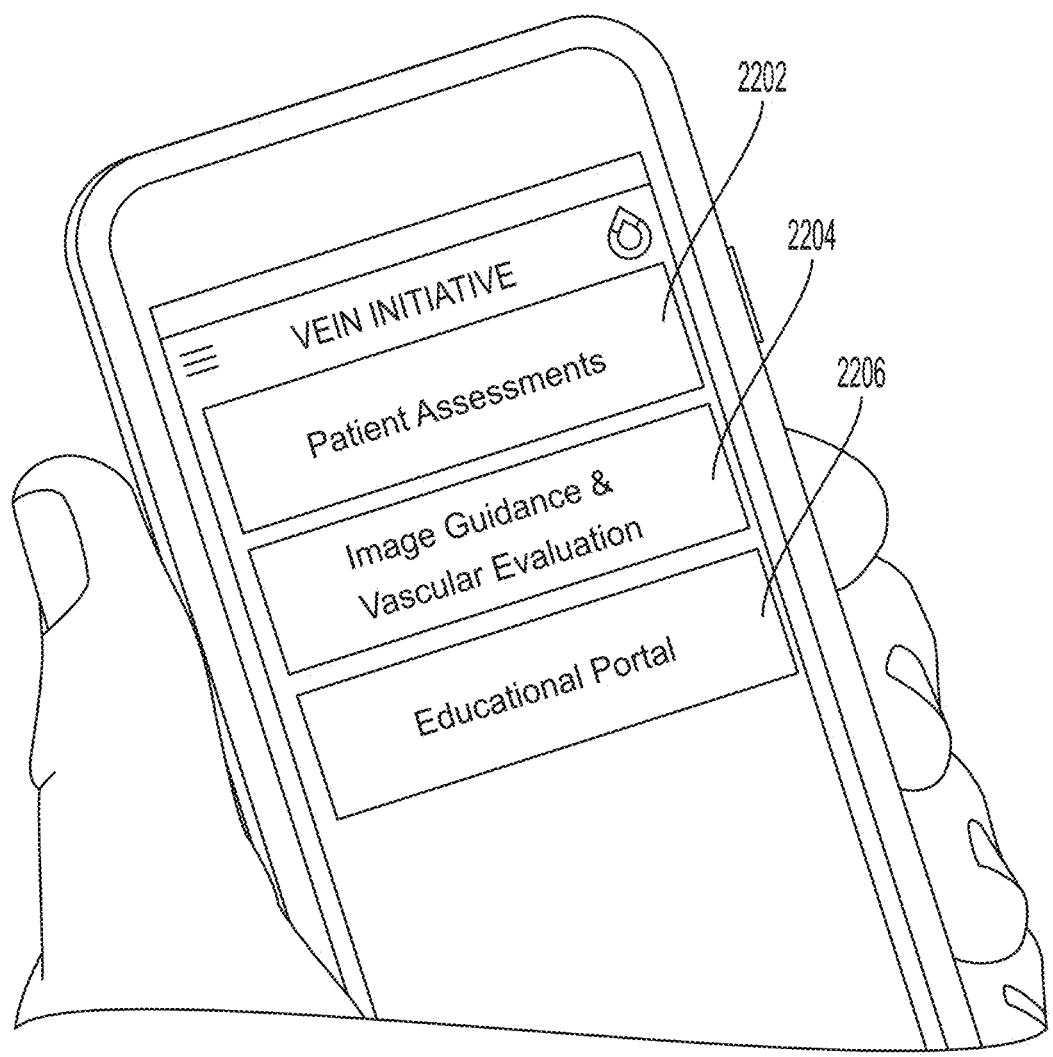
FIG. 22 shows an example of a graphical user interface accessible through a vascular assessment tool configured in accordance with certain embodiments of the invention.
Figure 23:
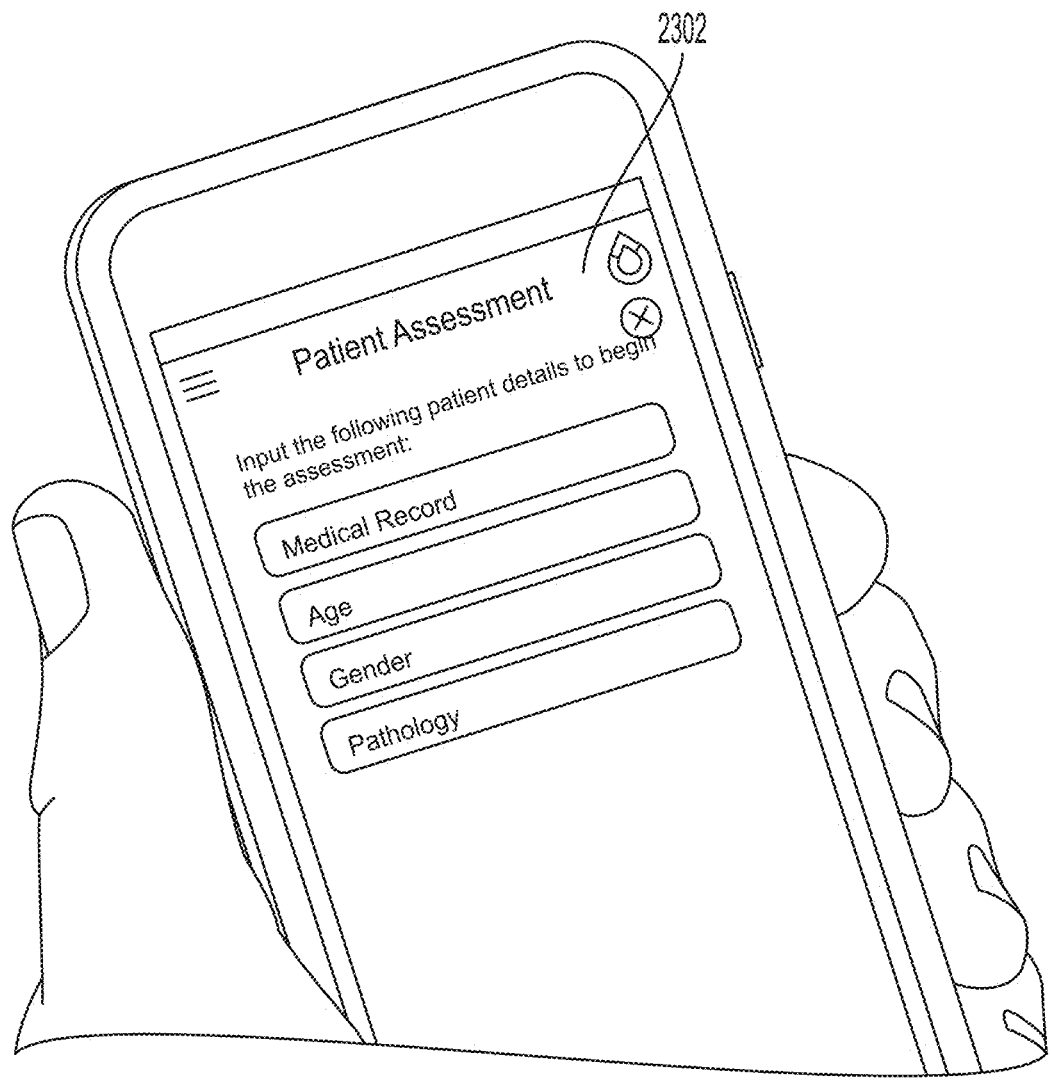
FIG. 23 shows an example of a graphical user interface accessible through a vascular assessment tool configured in accordance with certain embodiments of the invention.
Figure 24:
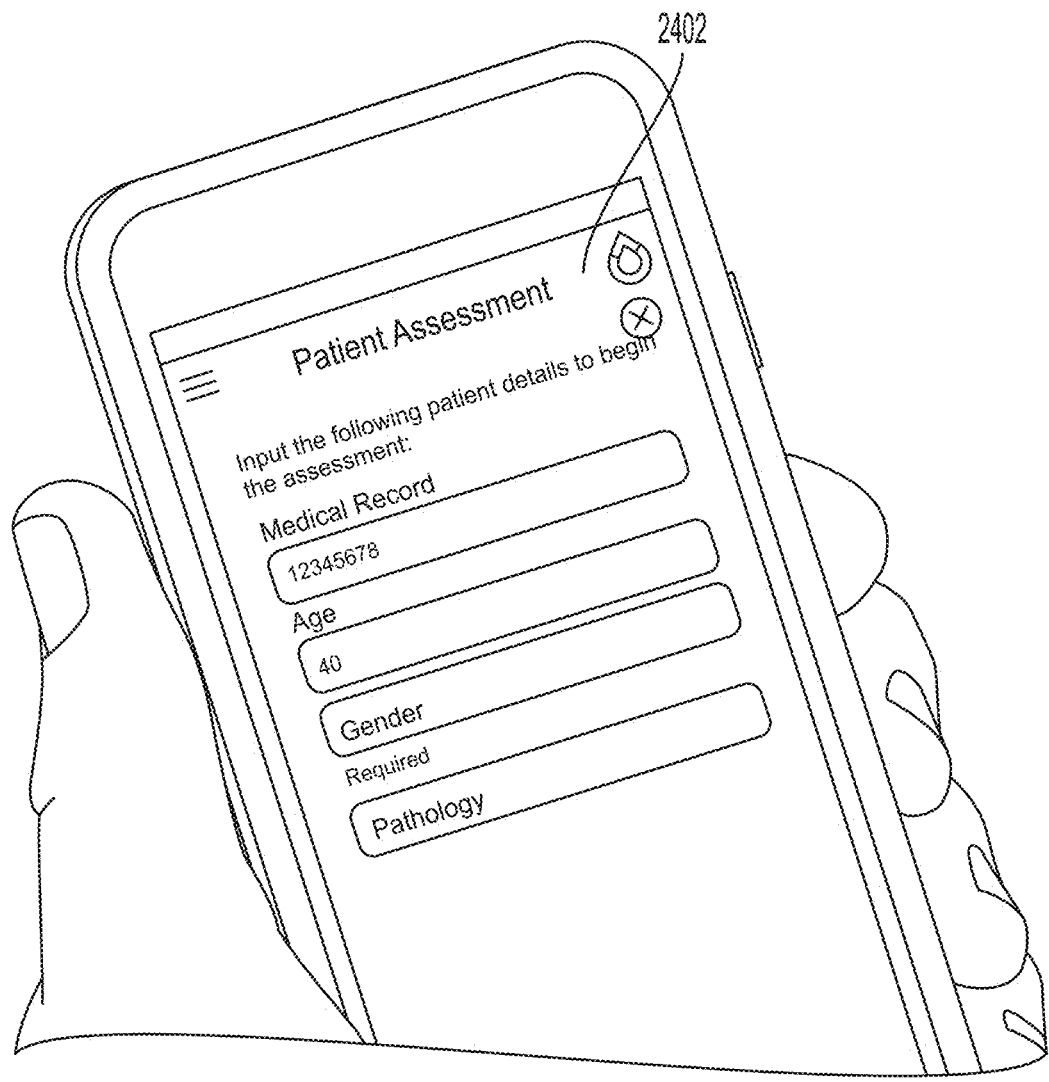
FIG. 24 shows an example of a graphical user interface accessible through a vascular assessment tool configured in accordance with certain embodiments of the invention.
Figure 25:
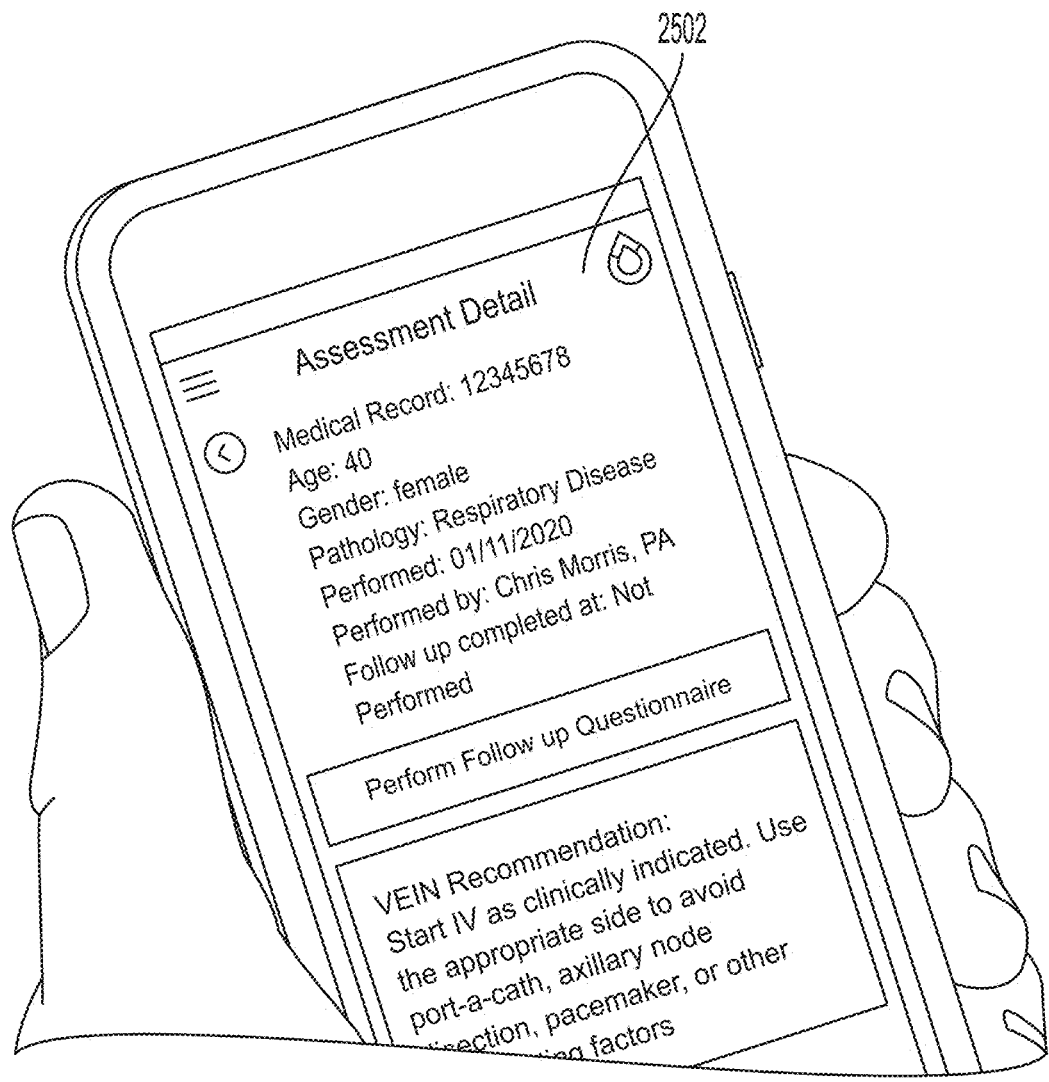
FIG. 25 shows an example of a graphical user interface accessible through a vascular assessment tool configured in accordance with certain embodiments of the invention.
Figure 26:
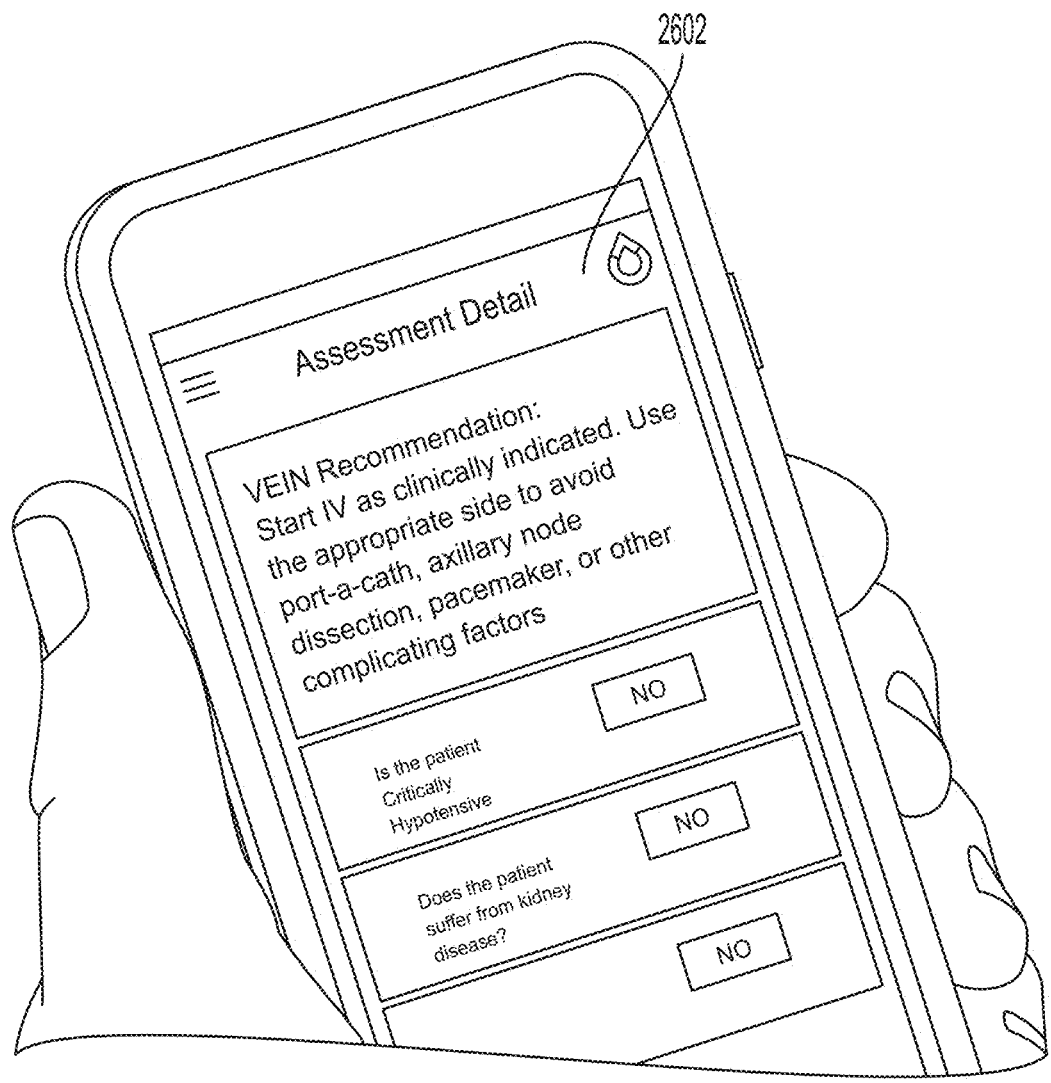
FIG. 26 shows an example of a graphical user interface accessible through a vascular assessment tool configured in accordance with certain embodiments of the invention.

FIG. 21 schematically illustrates an example of a computer architecture and associated processes structured for facilitating operation of vascular guidance systems 2102 and computer-based vascular assessment tools 2104 structured in accordance with certain embodiments of the invention. In this example, a vascular assessment tool 2104 (sometimes referred to herein as a "Vascular Early Intervention Needs" or "VEIN") process or tool) can be embodied as a computer-implemented or software-based evaluation tool useful in connection with a patient body. The tool 2104 can be programmed to provide for evaluation of pathology, comorbidities, and expected treatment modalities can be presented along with specific binary algorithm calculations, for example, to direct or rule out device use and needle placement for best results during a medical procedure. In developing the invention, the inventors have recognized that the vascular guidance system 2102 and the tool 2104 work together to implement the philosophy of "One Stick with One Device" as a new standard of vascular treatment. This standard involves using both objective and subjective data to assess treatment successes and failures, thereby creating objective, trackable, and reportable data for analysis of medical procedures. The tool 2104 can be considered a vascular device and decision tool designed to transform subjective decisions about vascular or other device placement into an objective and often standardized decision. The tool 2104 may employ one or more binary decision-making algorithms (e.g., comprising "yes" or "no" responses), for example, for analyzing pathology, patient history characteristics, existing comorbidities, and expected treatment modalities. The tool 2104 can assist practitioners with locating the best vascular or other placement devices and to track user successes and failures for learning purposes.

With reference again to FIG. 21, the vascular guidance system 2102 may comprise a clamping mechanism 2106 (embodiments of which have been described herein) coupled to an imaging apparatus 2108 (embodiments of which have been described herein), and configured for performing a medical procedure on a patient body 2110 (e.g., human tissue, animal tissue, or training device material). The medical procedure may be a vascular procedure, an injection procedure, or any other medical procedure which can be performed on tissue, vessels, or other parts of the patient body 2110. The clamping mechanism 2106 may be structured to receive and support one or more kinds of mobile devices 2112 having at least one screen display appropriately configured for receiving and displaying image data retrieved by the imaging apparatus 2108 from the patient body 2110. Examples of suitable mobile devices 2112 may include, without limitation, mobile phones, smartphones, tablets, graphic display enabled eyeglasses, wrist-band computing devices, or other devices which have a screen display capable of effective use with the guidance system 2102.

In certain embodiments, the tool 2104 may be in communication with a medical procedure system 2114, which may comprise a computer server 2114A operatively coupled to one or more data storage media 2114B. The system 2114 may be configured to provide data or computer-based instructions for downloading, installing, or implementing different modules 2104A-2104G of the tool 2104, for example. Calculations for patient treatments based on current and historical conditions may be performed internally by the system 2114 or by connectivity to one or more types of external data sources 2116. Remote sources of image data or other data may include past medical records, imaging done at another site for the subject under care, or other patient or medical procedure related information.

In certain embodiments, the vascular assessment tool 2104 may access the various modules 2104A-2104G to perform various functions and tasks when downloaded or installed for use on the mobile device. Such modules may be used to determine how the practitioner should apply a probe 2118 of the imaging apparats 2108, for example, or a vascular access device 2120 (e.g., a needle) to the patient body 2110.

An administration module 2104A may be configured to help a user or practitioner set up an account for use with the guidance system 2102. The user may be prompted to enter information such as name, license number (e.g., M.D., R.N. etc.), license expiration date (if any), address, phone number, and e-mail address. Billing information may also be entered such as billing name, business name, contact name, billing address, billing customer number (e.g., user may enter a preassigned VEIN customer number or the tool 2104 may automatically assign one based on network communications with the system 2114 or through another VEIN communication), phone number, and e-mail address. In other aspects, the administration module 2104A can be programmed for choosing payment options (e.g., ACH, credit card, debit card, or other), and for setting up screen timeout choices (e.g., screen lock at 10 minutes, 15 minutes, 30 minutes, etc.).

A patient assessment module 2104B can be programmed with one or more decision-making algorithms which can assess, provide guidance, and facilitate decisions for the appropriate vascular medical procedure to be performed. Decision algorithms can be designed to assist and recommend various line placements based on pathology, as well as expected standard treatment modalities, such as standards which adhere to INS standards and National Nephrology Foundation recommendations. These algorithms can be used throughout the healthcare continuum to try to avoid the unacceptable practice of multiple IV sticks, for example, to achieve vascular access. In entering data into the tool 2104, the user has an option to choose how data are entered, including by manual entry or bar code scan entry, for example.

A patient intake module 2104C can be programmed to assist with the process of entering demographic data, statistical data, and limited personal information related to the patient receiving the procedure. Such data may include the patient's name, date of birth, medical record number, room number, gender identification, the patient's current diagnosis for treatment reference, and indication (i.e., reason for the procedure, e.g., chemotherapy, dehydration, etc.). The intake module 2104C may determine whether a physician order is involved in the procedure, and therefore the decision-making algorithm aspects of the tool 2104 might be bypassed. In this event, the user may be routed directly to the imaging apparatus (e.g., ultrasound) module 2104D of the application.

Alternatively, the patient assessment module 2104B can be accessed to begin the VEIN decision-making process to determine the correct vascular access device (VAD) 2120 that matches the treatment modality. This decision-making algorithm may consider elements like pathology, comorbidities and BMI index, among many other factors (including factors described herein).

In one example of operation of the patient assessment module 2104B and the decision-making algorithm, Glomerular Filtration Rate (GFR) can be calculated based on lab work that is used as an indicator value as to the health and current function of the kidney. For example, a GFR less than 30 is a standard number recommend by the National Nephrology Foundation to contact the Nephrologist for their recommendation for vascular access. A GFR less than 30 may be deemed to fall outside the guidance of the tool 2104. If such a condition exists, the user may be directed by the tool 2104 to contact nephrology and end the assessment, so that nephrology can make the determination as to the health of the kidney, i.e., acute versus chronic kidney condition. The decision-making algorithms of the tool 2104 may be configured such that nephrology must advise the vascular proceduralist as to any future anticipated plan for arteriovenous shunt or graft, for example. In another decision point, if the patient has CKD Diagnosis Stage III or greater, this diagnosis indicates a progression of kidney disease/failure that can be an indication as to the need for dialysis. This determinant value alerts the practitioner to consider placing a vascular access device 2120 to protect and not stick the dominant limb.

In another example of the patient assessment module 2104B and the decision-making algorithm, a body mass index (BMI) can be a determinant value chosen due to changes in body habitus that often will not allow for the placement of an intravenous (IV) needle, for example. In the larger population, IV infiltrations are often more severe due to undetectable early signs that vesicant IV medications maybe leaking into the interstitial space. When an antibiotic has been ordered with extravasation properties, a midline should be chosen due to the potential for injury. If the answer to this assessment is affirmative, then a predetermined number of points (e.g., three points) may be added to a vascular assessment score which can be calculated and maintained by a vascular assessment scoring module 2104E, for example.

If it is determined at any time during the processing of the decision-making algorithm that the vascular assessment score meets or exceeds a predetermined threshold (e.g., five points), then the tool 2104 may route the user to a peripherally inserted central catheter (PICC) line module 2104F to guide the practitioner with applying a PICC line to the patient body 2110.

In another example of the patient assessment module 2104B and the decision-making algorithm, if the patient has had a previous stroke with limb weakness, the weakened limb should be avoided when choosing the vascular access device 2120. Muscle contraction promotes blood flow and prevents a deep vein thrombosis (DVT). A flaccid limb will experience venous stasis and this will promote thrombus formation when a vascular access device is introduced in that limb. If the answer to this assessment is affirmative, then a predetermined number of points (e.g., three points) may be added to a vascular assessment score which can be calculated and maintained by a vascular assessment scoring module 2104E, for example.

In another example of the patient assessment module 2104B and the decision-making algorithm, if it is determined that a pacemaker is present, then a PICC line cannot be placed on the same side as a pacemaker without cardiological approval due to the risk of dislodgement. If the answer to this assessment is affirmative, then a predetermined number of points (e.g., one point) may be added to a vascular assessment score which can be calculated and maintained by a vascular assessment scoring module 2104E, for example. In certain cases, the proceduralist cannot obtain the usual cavoatrial position from the left due to there being no pathway. If the patient has a right-sided pacemaker, the practitioner may place a right-sided midline; however, a PICC line cannot be placed without cardiological approval. A physician may need to be contacted due to the possibility that the individual has a double superior vena cava.

In other examples of processing by the patient assessment module 2104B, the vascular assessment score can be adjusted on the basis of affirmative answers as follows (with appropriate points applied): patient has been prescribed and will receive antibiotics for up to five days intravenously (one point); patient will be given antibiotics for a period of more than five days (two points); prescribed long-term antibiotics for discharge from the hospital (a PICC line is the accepted safest means of receiving long term antibiotic treatments outside the hospital among healthcare professionals—due to care and maintenance challenges and the risk for infection, a single lumen PICC is used—two points); antibiotics 12/24 hours—practitioner decides if the patient will receive antibiotics at home intravenously (one point); antibiotics every eight hours—user decides if the patient will receive antibiotics every eight hours (two points) electrolyte replacement protocol—user decides if the patient has an electrolyte replacement plan (one point); respiratory issues—user decides if the patient has any noted respiratory problems (one point); patient has left or right-side port—user decides if the patient has a port on the left or right side (one point)—designates vascular access to be done on the opposing side; post chemotherapy (one point); restriction of movement on left or right side (one point)—designates using the opposing side for vascular access; mastectomy on right or left side—user decides if the patient has a history of a right or left breast removal (one point)—designates using the opposing side for vascular access; readmitted within 30 days—user decides if the patient has been admitted previously within 30 days (one point); user decides if the patient has a history of peripheral vascular disease (one point); past PIV infiltrations—user determines if the patient has a history of past peripheral intravenous line infiltrations (one point); multiple PIV attempts—user decides if the patient has a history of multiple peripheral intravenous line attempts (one point); right access exclusion—user determines if the patient has exclusions to using the right side for vascular access (one point)—user is directed to use the left side for access; left access exclusion—user determines if the patient has any left side exclusion for vascular access (one point)—designates using the opposing side for vascular access.

Once all desired or required portions of the VEIN assessment are completed, the vascular assessment scoring module 2104E can calculate a total vascular assessment score. If the total score is in the range of zero to two points, for example, then the practitioner can be guided to an image apparatus guided vascular access module 2104G and directed to use standard image apparatus guided intravenous procedures, such as ultrasound guided intravenous (USGIV) procedures, for example. If the total score is in the range of three to four points, for example, then the practitioner can be guided to the image apparatus guided vascular access module 2104G and directed to use midline procedures.

In connection with using the imaging apparatus module 2104D, the user may be asked to select the type of connection used for a transducer for an ultrasound, for example, or another type of imaging device or technology. The transducer connection to the mobile device 2112 may be directly connected or connected by any type of wire suitable to communicate the signal. The transducer may be connected via WiFi, Bluetooth, or some other type of wireless connection. In another aspect, the user may be presented with frequency options. These choices may be related to ultrasound but other imaging technologies or devices are within the scope of the invention. The frequency selected for an ultrasound transducer may be 10 MHz, for example. Also, the user may choose whether or not to use Doppler, including color Doppler or duplex Doppler, for example.

The imaging apparatus module 2104D may offer choices of vascular access devices 2120 such as needles of different sizes, depending on a particular application or medical procedure. Examples of needle sizes include, without limitation, 24-gauge, 22-gauge, 20-gauge, or 18-gauge, among others. The module 2104D may also facilitate use of midline procedures on the patient. Different PICC line options may be presented to the practitioner, such as 6 French sufficient for a triple lumen PICC, a 5 French sufficient for a double or triple lumen PICC, or a 4 French sufficient for a single lumen PICC.

After preparing the patient body 2110 for the procedure, the practitioner initiates the imaging process and selects a desired vascular structure desired. The tool 2104 can be programmed to identify vessel structure walls, measure its dimensions, and display the vessel structure on the screen display. The tool 2104 may be configured to measure the black space around the user's vessel structure selection to accept this as the user's targeted area and display relevant measurements. The tool 2104 may be further programmed to confirm appropriate dimensions or characteristics of the vessel structure in response to the size and type of vascular access device 2120 which has been selected (e.g., gauge of needle). For example, the tool 2104 may consider the size or gauge of line entering the vein and the diameter of the vein to ensure minimal risk of occluding the vein. The tool 2104 may further calculate the depth of vessel and display a suggested optimal angle to enhance the success of obtaining access with most accuracy. The practitioner then performs the desired procedure to obtain vascular access.

In various embodiments, the tool 2104 may store or communicate data associated with the performed procedure to a designated location, such as to the system 2114, for example. Data may be communicated in a chosen format subject to relevant data communication protocols for transmitting and receiving devices and systems. The user has an option to send procedural information to the facility's designated location via a user pre-selected method. Electronic data can be encrypted prior to communication.

In other aspects of the tool 2104, an education portal can allow the user to choose to access VEIN educational content. The user may have an option to select a section of the application for emergency purposes, such as a choice of which type of activity to select for emergency services. The techniques described herein may be employed in trauma settings using focused assessment with sonography in trauma (FAST) exam criteria, for example, perhaps using a probe at a comparatively lower frequency for immediate diagnosis of subject conditions. In other embodiments, the user may be allowed to order laboratory testing for the patient (e.g., blood chemistries and other related labs). The user can be permitted to obtain various venous testing (e.g., blood gases and other related venous testing), blood sugar testing (e.g., A1C), and other tests. It can be appreciated that the tool 2104 may be used separate from the guidance system 2102 and may incorporate remote imaging for one or more dimensions with records, vitals, and image data transferred to the display screen for viewing by the user.

The produced images and other clinical data which may come from local or remote sources may also be delivered to users through a portable handheld or wearable device. Connectivity may be provided to medical databases or electronic medical records (EMRs) to enhance the situational awareness and visualization of critical anatomic structures. Projection to visual display devices may include using headsets, goggles, glasses and other hands-free assisting mechanisms.

FIGS. 22 through 26 show examples of graphical user interfaces accessible through a vascular assessment tool configured in accordance with certain embodiments of the invention. The screen display of FIG. 22 includes a "Patent Assessments" link, which may provide access to the functions of the patient assessment module 2104B, for example. An "Image Guidance and Vascular Evaluation" link may provide access to one or more of the imaging apparatus module 2104B, the PICC line module 2104F, and/or the image apparatus guided vascular access module 2104G, for example. An "Educational Portal" link may provide access to educational content associated with training practitioner in how to use a vascular guidance system or otherwise to perform a vascular access medical procedure on patient. FIGS. 23-26 include various screens 2302, 2402, 2502, 2602 displaying content viewable through access to the patent assessment module 2104B, for example.

Figure 27:
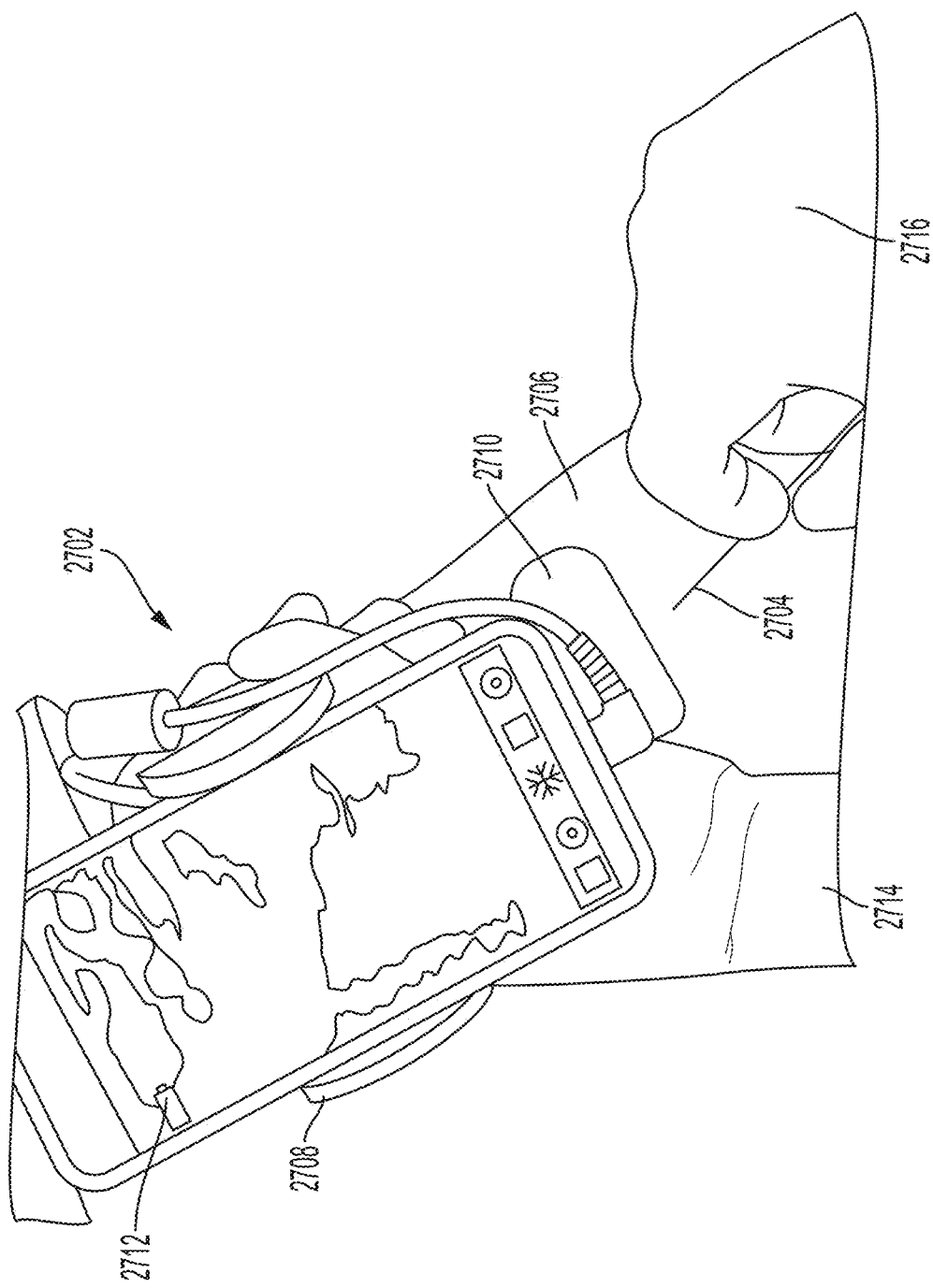
FIGS. 27 and 28 depict different views of an example of a vascular guidance system as employed by a practitioner during a medical procedure to inject a needle into the arm of a patient.
Figure 28:
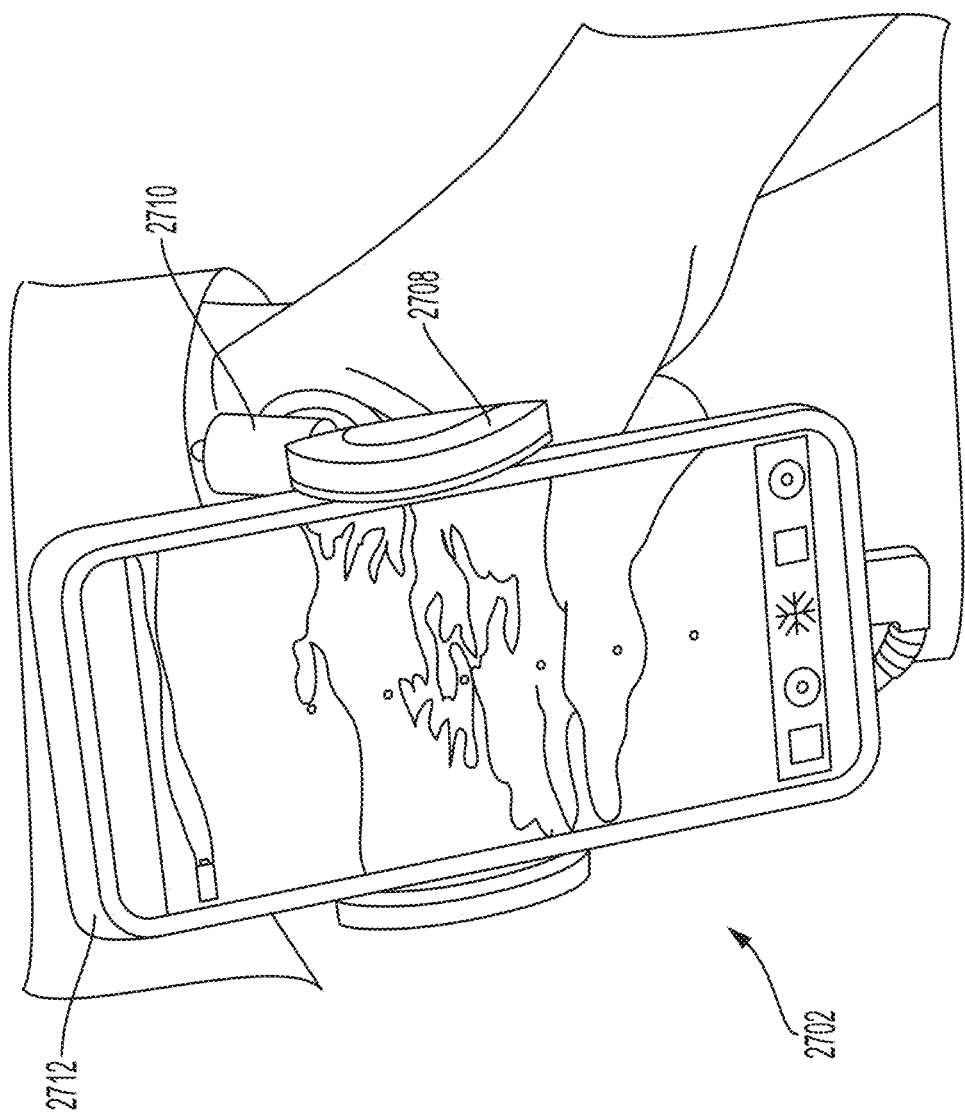
Figure 31D:
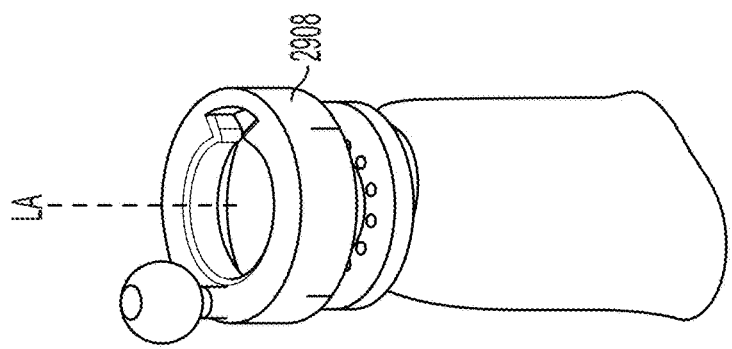
FIGS. 31A through 31D include various three-dimensional views depicting one example of a staged progression of the rotational movement and position changes associated with the rotating portion of a coupling mechanism.
Figure 31C:
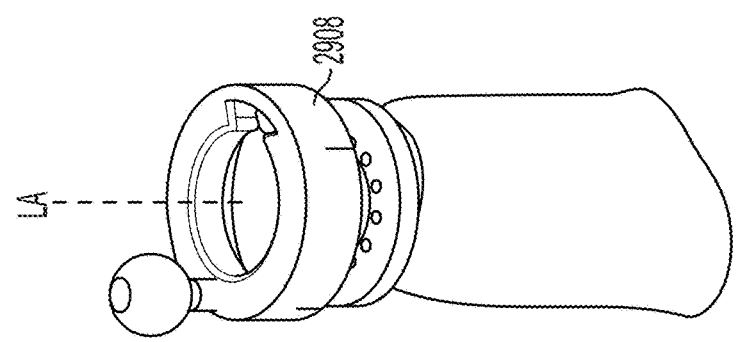
Figure 31B:
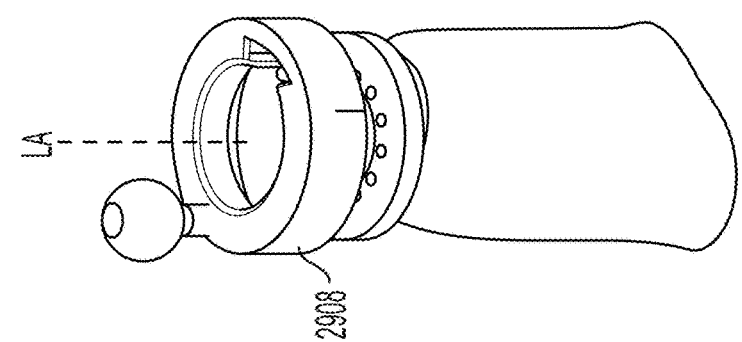
Figure 31A:
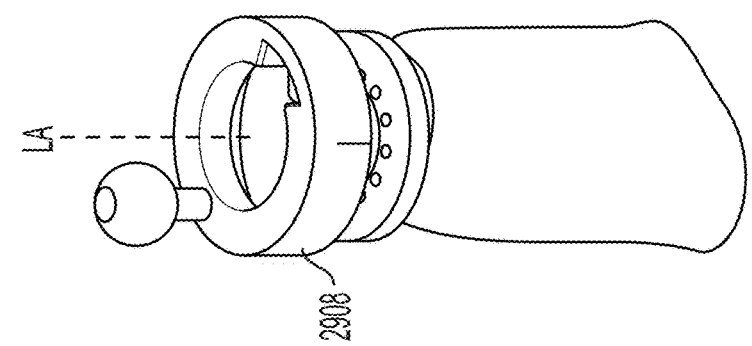
Figure 32:
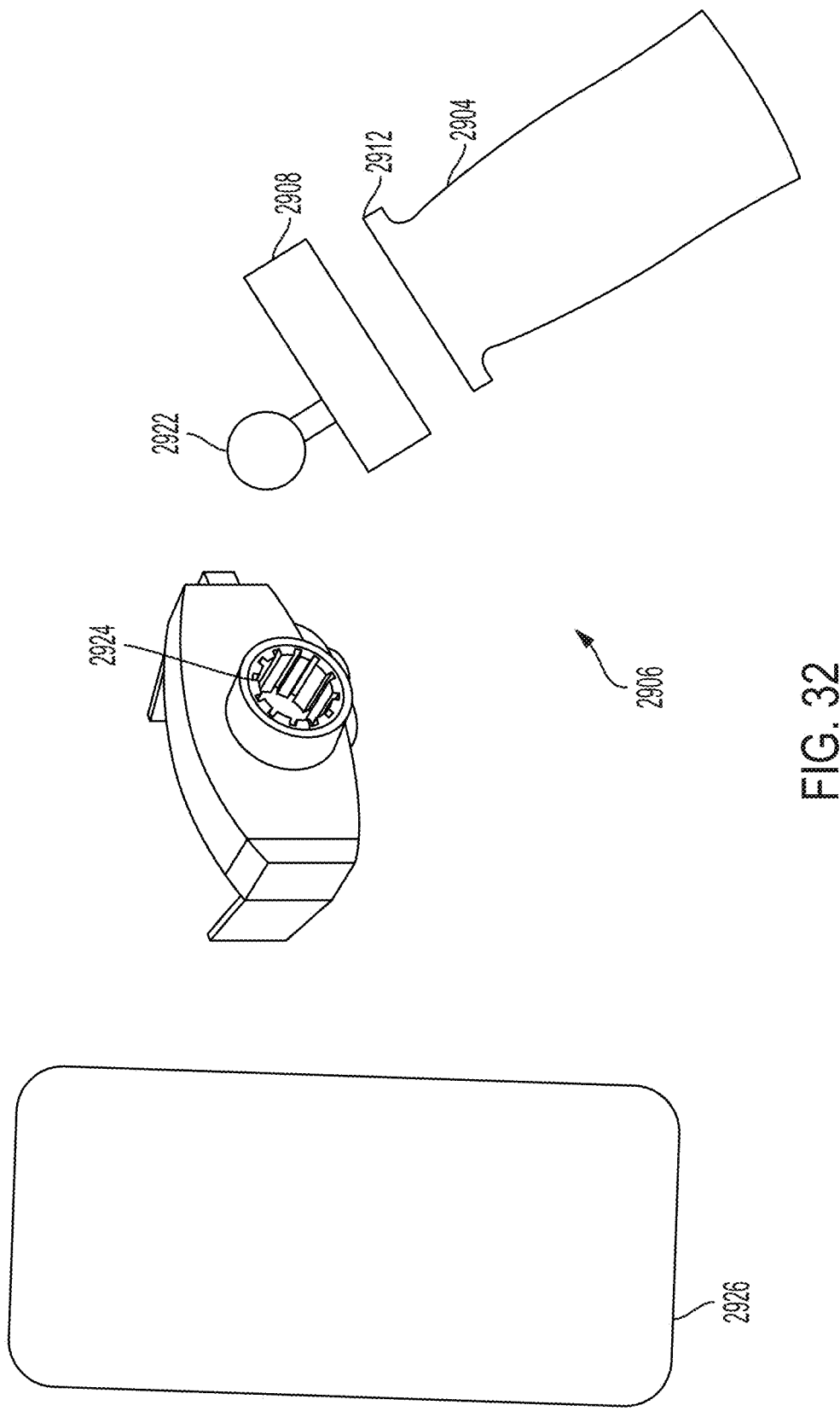
FIG. 32 includes a three-dimensional exploded and schematic view of a guidance apparatus and an image display device structured in accordance with embodiments of the invention.
Figure 34:
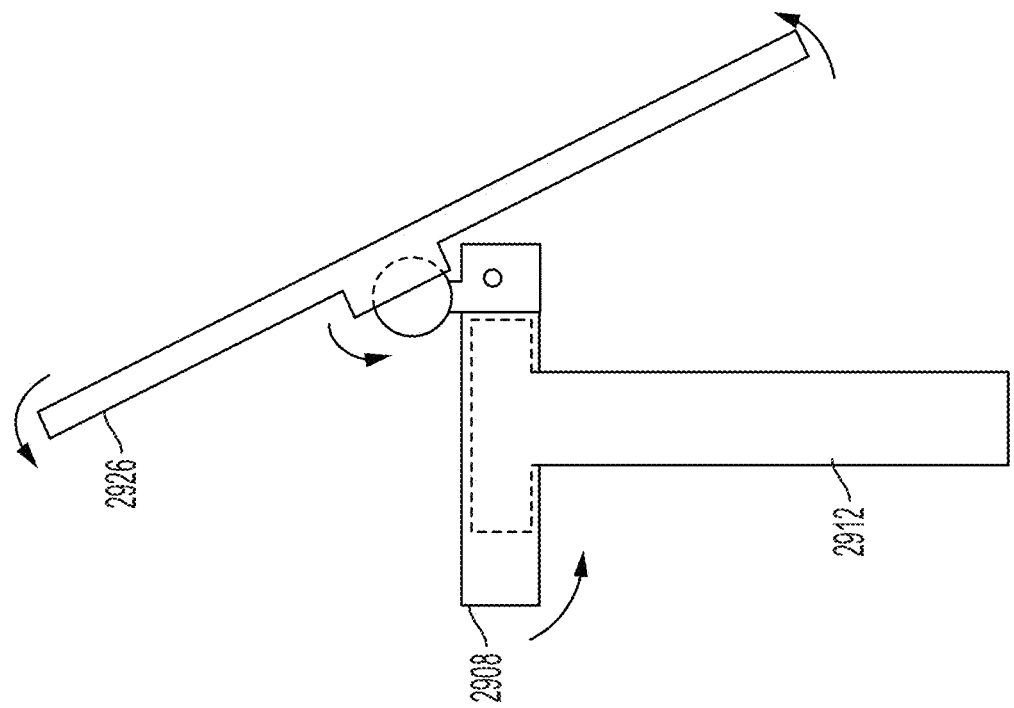
FIGS. 33 through 36 illustrate different views of how a guidance device structured in accordance with embodiments of the invention facilitates orienting an image display device relative to an imaging apparatus.
Figure 33:
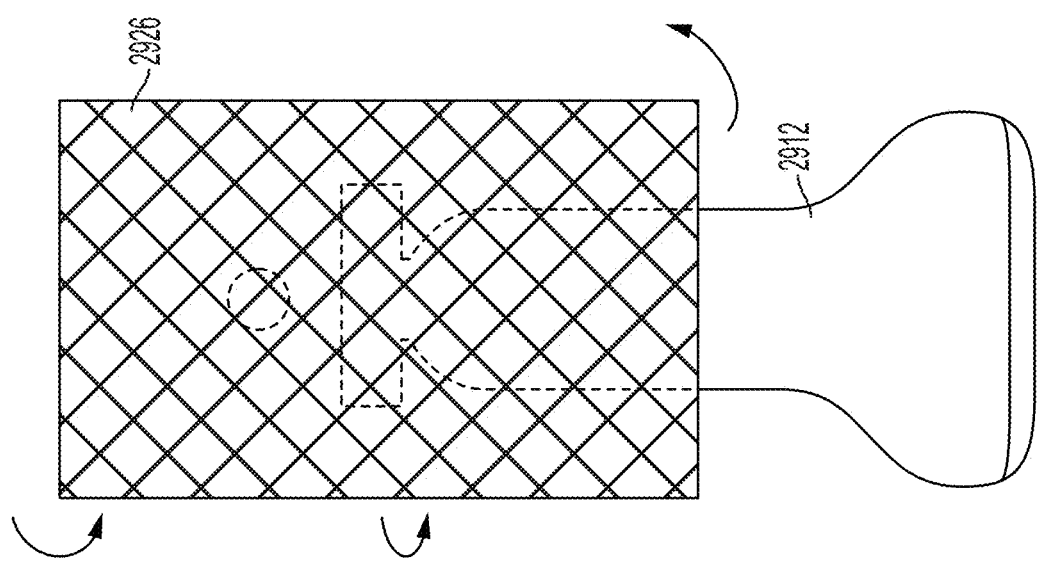
Figure 36:
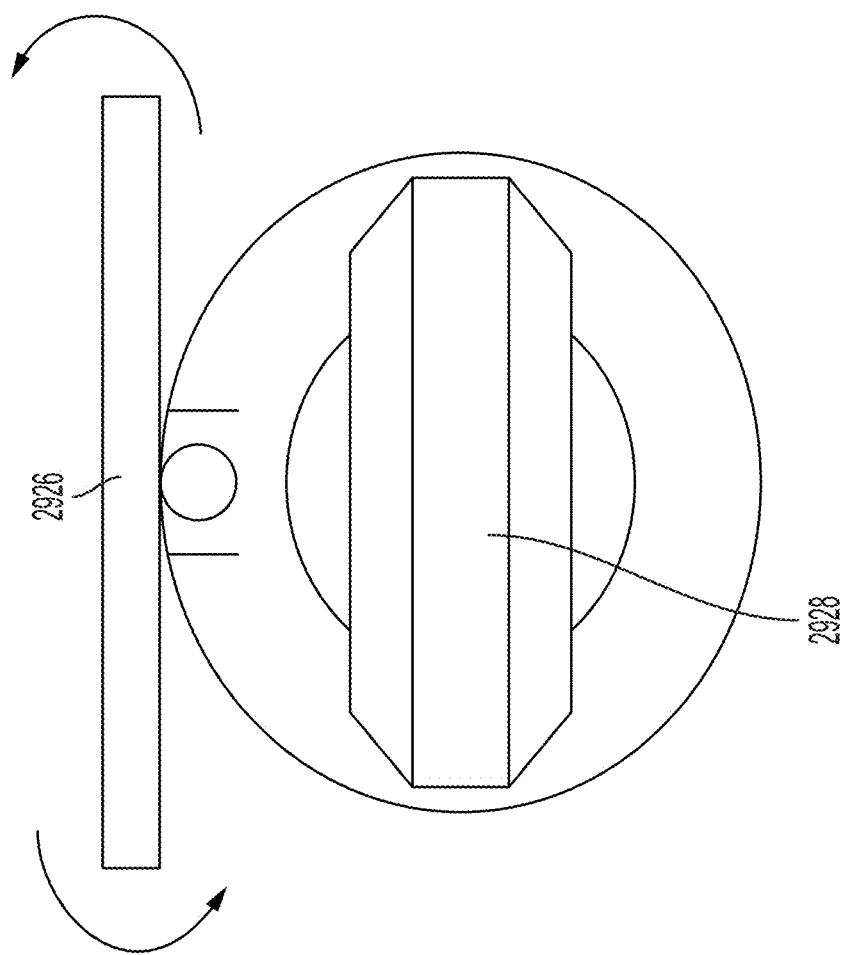
Figure 35:
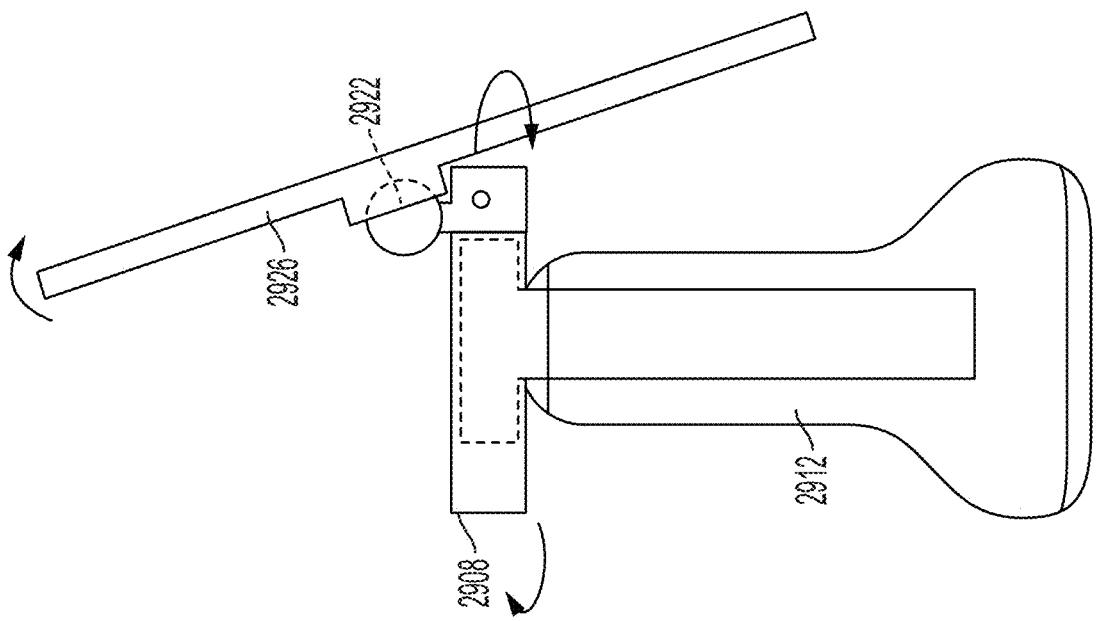

FIGS. 27 and 28 depict different views of an example of a vascular guidance system 2702 in use by a practitioner during a medical procedure to inject a vascular access device 2704 (e.g., a needle) into an arm 2706 of a patient. In the example shown, the guidance system 2702 comprises clamping mechanism 2708 in operative combination with imaging apparatus 2710. The clamping mechanism 2708 of the guidance system 2702 secures a mobile device 2712 therein. In this example, an ultrasound image derived from the function of the imaging apparatus 2710 is displayed on the screen display of the mobile device 2712. It can be appreciated that the image displayed on the mobile device 2712 screen display can assist the practitioner to properly place and insert the needle 2704 into the arm 2706 of the patient. In addition, it can be appreciated that the design of the guidance system 2702 facilitates use by a single hand 2714 of the practitioner, thereby freeing the other hand 2716 to employ the needle 2704 during the medical procedure.

FIGS. 29A through 29D, FIGS. 30A through 30C, FIG. 31, and FIG. 32, collectively illustrate an example of a guidance apparatus 2902 structured in accordance with various embodiments of the present invention. As described above, the guidance apparatus 2902 can be structured for use with a portable imaging apparatus (e.g., an ultrasound imaging apparatus) and an image display device (e.g., a mobile device with a screen display, or a dedicated, stand-alone screen display). In this example, the guidance apparatus 2902 includes a sleeve portion 2904 structured for receiving an imaging apparatus. The sleeve portion 2904 may be comprised of a flexible and/or plastic material which can suitably receive and substantially conform to a body shape of an imaging apparatus inserted and received into the sleeve 2904.

The guidance apparatus 2902 may further include a coupling mechanism 2906 which comprises a rotating portion 2908 rotationally engaged with the sleeve portion 2904. In the example shown, the rotating portion 2908 may be embodied as a clip ring having a lip 2910 formed circumferentially around an interior of the clip ring. The sleeve portion 2904 may further comprise a collar 2912 having a guide rail 2914 formed circumferentially around the exterior of the collar 2912. The guide rail 2914 can be structured for engaging with the rotating portion 2908 of the coupling mechanism 2906 via the lip 2910 of the collar 2912 to provide for rotatability of the rotating portion 2908 relative to a longitudinal axis LA extending though the sleeve portion 2904. The material comprising the collar 2912 and/or the rotating portion 2908 may be selected such that a friction fit can be readily achieved allowing for either readily engaging or disengaging the collar 2912 and the clip ring 2908.

In certain embodiments, the collar 2912 of the sleeve portion 2904 may further comprise a plurality of index recesses 2916 formed therein. Also, the rotating portion 2908 of the coupling mechanism 2906 may include a detent tab 2918 formed therein. The detent tab 2918 may further comprise a protrusion 2920 extending therefrom which is structured for being received into each of the index recesses 2916. In this manner, as the rotating portion 2908 is rotated, the protrusion 2920 can be alternately inserted into each of the plurality index recesses 2916 to provide a plurality of rotation positions of the clip ring 2908, for example. In this manner, the rotating portion 2908 can be secured in place on a temporary basis in multiple desired positions as the rotating portion 2908 is rotated around the longitudinal axis LA. FIGS. 31A through 31D illustrate an examiner of a staged progression of the rotational movement and position changes associated with the rotating portion 2908 of the coupling mechanism 2906

In certain embodiments, the coupling mechanism 2906 may further include a first connecting portion 2922 extending from the rotating portion 2908. Among other structures, the first connecting portion 2922 may be embodied as a ball, as shown in the example. Also, a second connecting portion 2924 may be provided which is structured for operative connection with the first connecting portion 2922 and structured to be engaged with at least portion of an image display device 2926, as shown. The second connecting portion 2924 may comprise a socket, for example, to form a ball-and-socket joint when the ball is inserted into the socket during use of the apparatus With reference to FIGS. 33 through 36, it can be appreciated that the coupling mechanism 2906 facilitates orienting the image display device 2926 relative to the imaging apparatus (which is inserted and received into the sleeve portion 2904) to provide a direct line of sight of an area imaged by an imaging apparatus 2928. The coupling mechanism 2906 can be adjustable for facilitating rotation of the image display device in at least one 360-degree plane of rotation about a longitudinal axis extending through the imaging apparatus. Also, the coupling mechanism 2906 can be structured to allow the coupling mechanism 2906, the image display device 2924, and the imaging apparatus 2928, in combination, to be held in a single hand of a user during performance of a medical procedure, for example. In other aspects, the second connecting portion 2924 can be structured for allowing the image display device 2926 to be oriented between forward and backward positions, for example. Alternatively, the second connecting portion 2924 may be structured for allowing the image display device 2926 to be oriented between portrait and landscape positions. In certain embodiments, the imaging apparatus 2928 when operatively installed is wirelessly communicatively coupled to the image display device 2926 to enable displaying image data received from the imaging apparatus 2928 on a screen display, for example, of the image display device 2926.

Figure 37A:
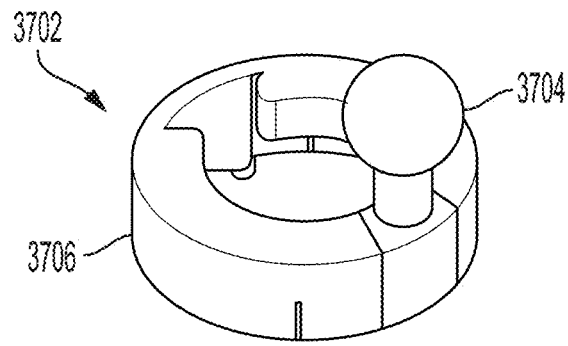
FIGS. 37A through 37C depict different three-dimensional views of different positions of a first connecting portion relative a rotating portion in accordance with certain embodiments of the invention.
Figure 37B:
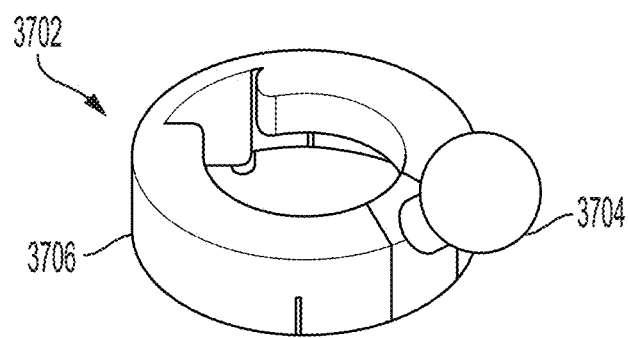
Figure 37C:
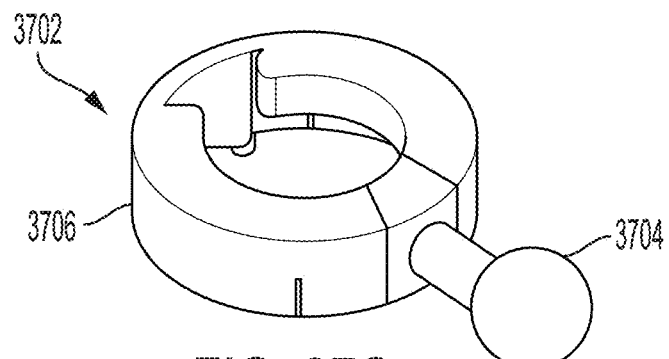
Figure 38A:
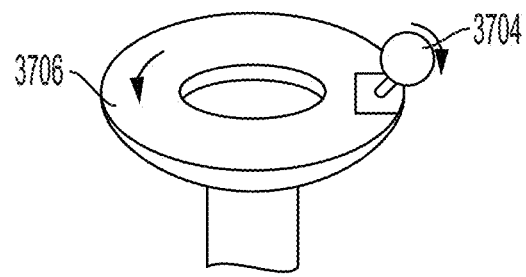
FIGS. 38A through 38D depict different three-dimensional views of different positions of a first connecting portion relative to a rotating portion structured in accordance with certain embodiments of the invention.
Figure 38B:
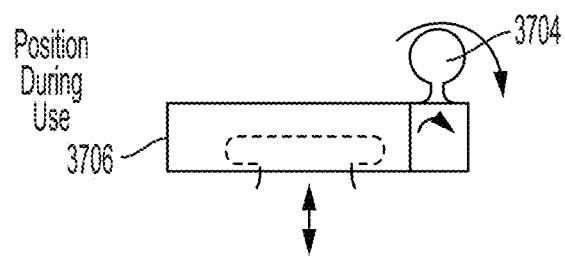
Figure 38C:
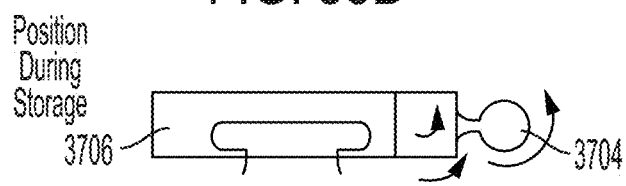
Figure 38D:
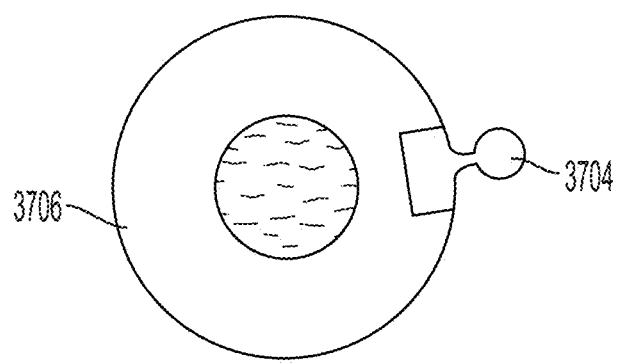
Figure 39:
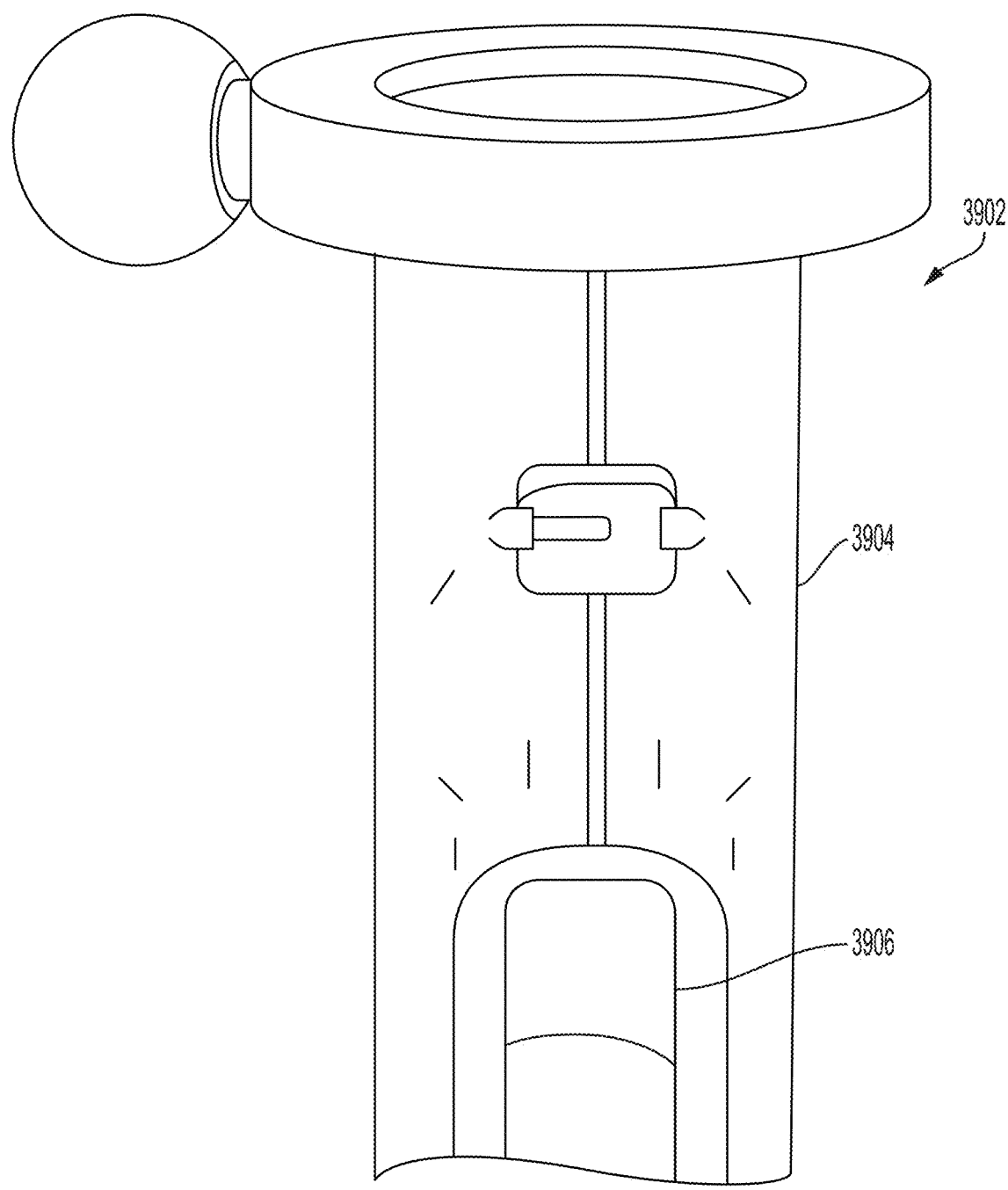
FIG. 39 illustrates a three-dimensional view of an alternative embodiment of a sleeve portion having an interface cutout formed therein.

With reference to FIGS. 37A through 37C, as well as FIGS. 38A through 38D, in certain embodiments a first connecting portion 3704 of a coupling mechanism 3702 can be structured to be independently movable with respect to its connection to the rotating portion 3706 of the coupling mechanism 3702. This feature allows multiple different positions and orientations of an image display device to be achieved relative to the coupling mechanism 3702. Such different positions of the first connecting portion 3704 can also facilitate storage of the apparatus or its components when not in use, for example. In another aspect, FIG. 39 illustrates an example of a guidance apparatus portion 3902 structured with a sleeve portion 3904 having an access cutout 3906 formed therein. The access cutout 3906 may be structured and formed in a location of the sleeve portion 3904 corresponding to a location of the operative controls (e.g., power on/off, focus, record on/off, etc.) of an imaging apparatus, for example, which has been inserted and received into the sleeve portion 3904.

Figure 40:
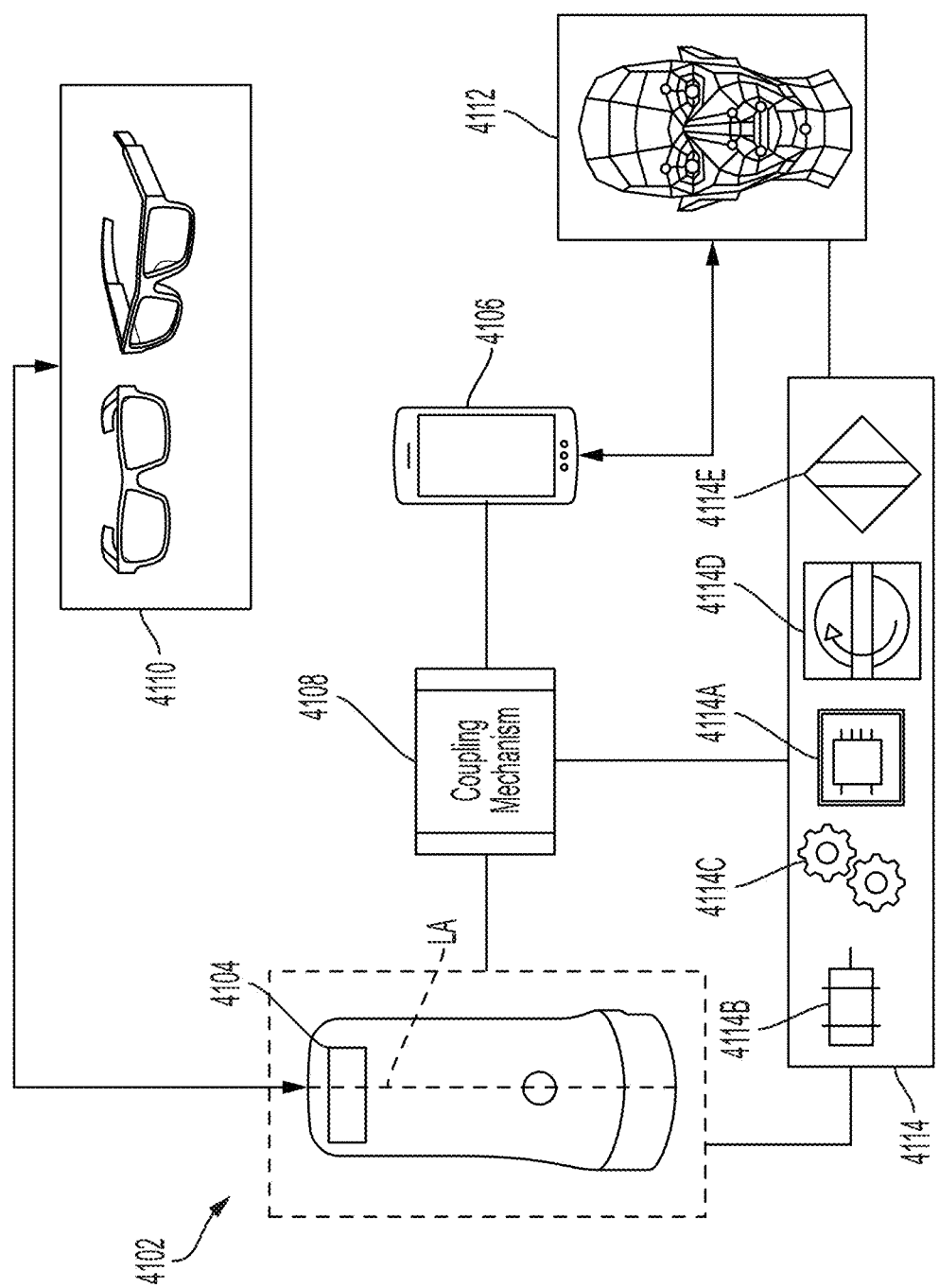
FIG. 40 schematically illustrates an overview of various embodiments of a guidance apparatus which can be structured in accordance with various embodiments of the present invention.

FIG. 40 schematically illustrates an overview of various embodiments of a guidance apparatus 4102 which can be structured in accordance with various embodiments of the present invention. As shown, the guidance apparatus 4102 can be structured for use, either attached to or an integral part of, a portable imaging apparatus 4104 (e.g., an ultrasound imaging apparatus) and an image display device 4106

(e.g., a mobile device with a screen display, or a dedicated, stand-alone screen display). In various embodiments, a coupling mechanism 4108 can provide a mechanical connection or coupling between the image display device 4106 and the guidance apparatus 4102. As described above, the coupling mechanism 4108 can be used to facilitate orienting the image display device 4106 relative to the imaging apparatus 4104 to provide a direct line of sight of an area imaged by the imaging apparatus 4104 (e.g., a location on a body of a medical procedure patient). Also, the coupling mechanism 4108 can be adjustable for facilitating rotation of the image display device 4106 in at least one 360-degree plane of rotation about a longitudinal axis LA extending through the imaging apparatus 4104. In certain aspects, the coupling mechanism 4108 can be structured to allow the coupling mechanism 4108, the image display device 4106, and the imaging apparatus 4104, in combination, to be held in a single hand of a user or practitioner during performance of an imaging procedure, for example.

In various embodiments, an imaging procedure may involve any suitable use to which the imaging apparatus 4104 may be applied for inspecting an area or area. For example, the imaging procedure may involve a variety of applications such as metallurgical assessment (e.g., examining cracks in physical structures), solid state physics, measurements, cameras, cleaning, navigation, sonar, or military applications, among many others.

In certain embodiments, use of software applications described here in connection with the guidance apparatus 4102 may include not only vascular procedures, but also any procedure which involves scanning, measurement, reporting, and/or diagnosing an object to which the guidance apparatus 4102 can be applied. For example, a suitable software application and an appropriately configured guidance apparatus 4102 can be used in combination for procedures involving diabetes, tumors, blood flows, vascular insertions, organ function, and neurological functions, among others.

In certain embodiments, the image display device 4106 may be operatively associated with one or more kinds of eyewear viewing devices 4110, such as smart glasses, smart goggles, or virtual reality viewing equipment, enabled for wireless communication. The eyewear viewing devices 4110 can include a screen display, electronic circuitry, and/or software configured for communicating directly with the imaging apparatus 4104, for example. In this manner, the view of a location or area as seen by the imaging apparatus 4104 can be conveyed to a user or practitioner using the eyewear device 4110. For example, this arrangement can provide direct line-of-sight viewing during an image guided procedure performed by a user wearing the eyewear device 4110.

In other embodiments, the image display device 4106 may be programmed to interact and communicate with various kinds of facial recognition algorithms 4112. For example, the image display device 4106 can access the recognition algorithm 4112 to determine the eye position or location data associated with the physical eyes of a user. This eye position or location data can be communicated to a controller 4114A of a drive mechanism 4114, which may include an operatively associated configuration of a motor 4114B (e.g., a servo motor) and mechanical gears 4114C. The drive mechanism 4114 may be operatively associated with one or both of the guidance apparatus 4102 and/or the coupling mechanism 4108 to enable movement of the components therein. Such component movement can result in changing the tilt, orientation, rotation degree, or other operative position of the guidance apparatus 4102 and/or the coupling mechanism 4108, such as to provide more effective direct line-of-sight viewing of an area or areas of interest for the practitioner using the imaging apparatus 4104.

In certain embodiments, a gyroscope 4114D may be embodied as a micro electro mechanical systems (MEMS) gyroscope within the drive mechanism 4114. The gyroscope 4114D may include circuitry and a sensor to detect and register changes in angular displacement or linear orientation for one or more components of the guidance apparatus 4102. In certain embodiments, an accelerometer 4114E may be provided with circuitry and a sensor that senses linear changes relative to the frame of reference of components of the apparatus 4102. Working in combination, the accelerometer 4114E and the gyroscope 4114D can sense the orientation of the component device and any accelerated movement. If there is displacement that indicates acceleration in a particular direction, with a vibrating motion caused by the gyroscope 4114D, an electrical current can be generated which signals further action to be taken by the guidance apparatus 4102 and/or other components or devices operatively associated with the guidance apparatus 4102.

Figure 41:
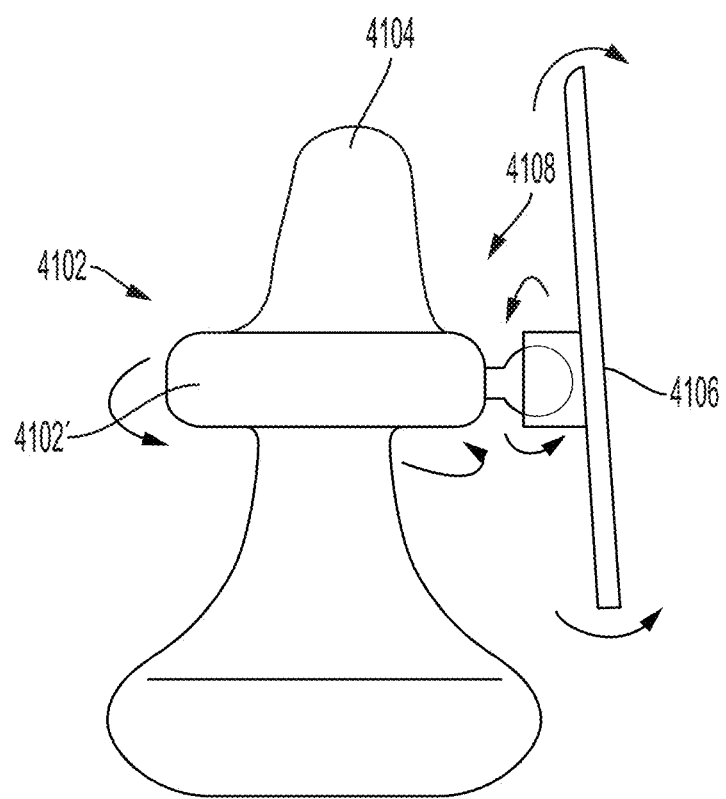
FIGS. 41 through 43 schematically depict different aspects of one example of a guidance apparatus with a coupling mechanism embodied as a slip ring portion.
Figure 42:
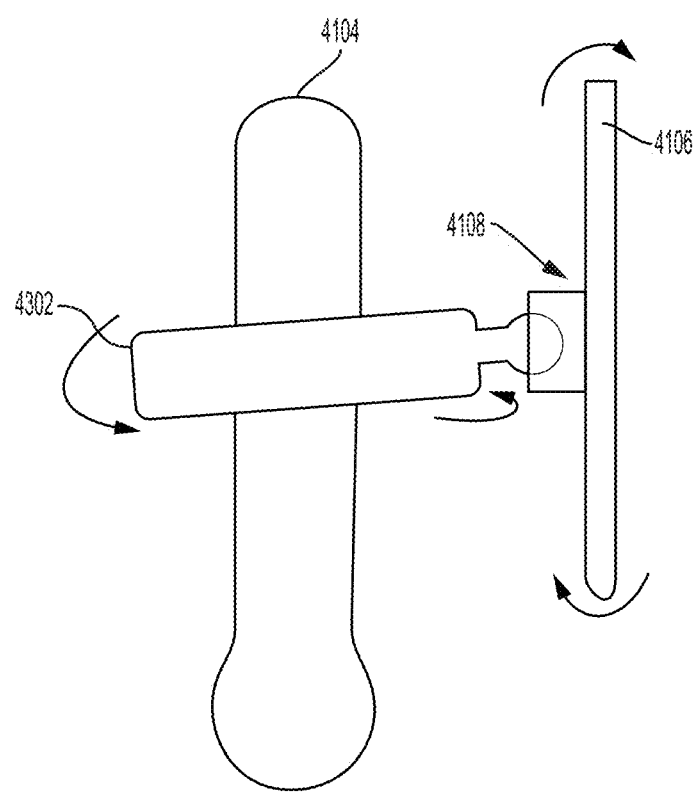
Figure 43:
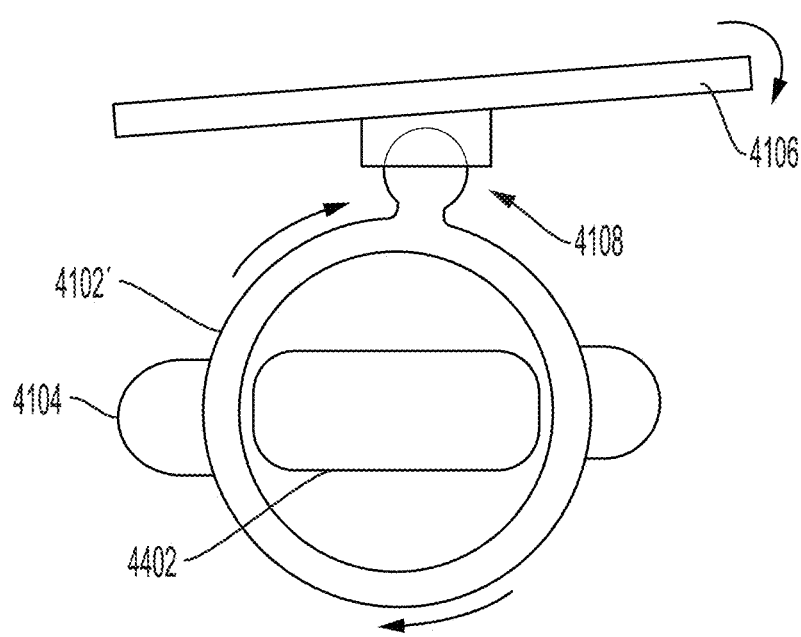
Figure 44:
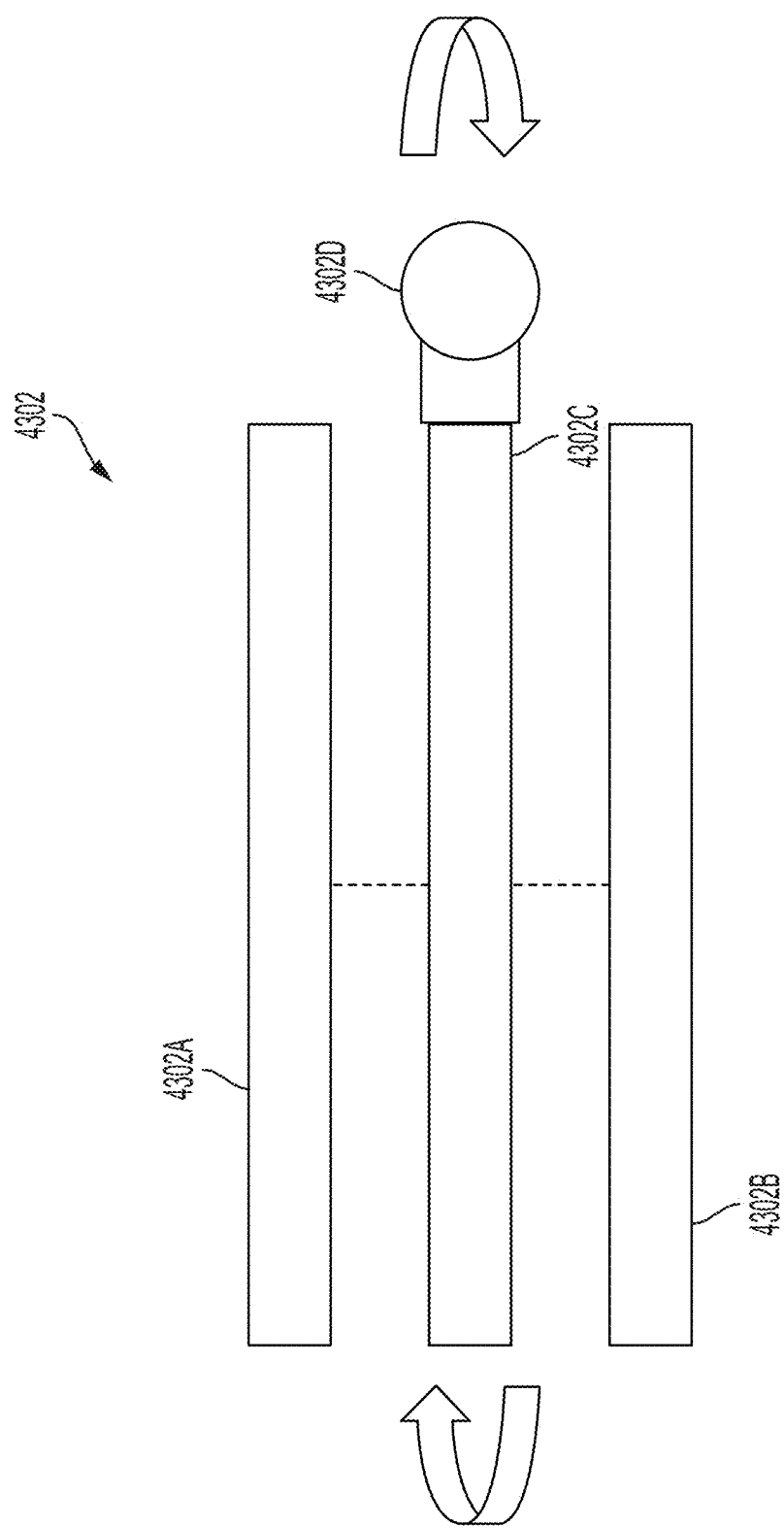
FIG. 44 illustrates an exploded view of one example of a slip ring portion.

With reference to the example of a guidance apparatus 4102 shown in FIGS. 41 through 43, in certain embodiments the coupling mechanism 4108 of the guidance apparatus 4102 can be embodied as a slip ring portion 4302 structured for receiving the imaging apparatus 4104 therein. The slip ring portion 4302 may further include a sleeve portion 4402 comprised of a flexible material which can allow passage of imaging apparatus 4104 therethrough, while substantially and sufficiently securely conforming to a body shape of the imaging apparatus 4104, when the apparatus 4104 is inserted and received into the sleeve portion 4402. FIG. 44 illustrates an exploded view of one example of a slip ring portion 4302 comprising top and bottom ring portions 4302A, 4302B securing and confining rotating component 4302C therein. In this example, a ball portion 4302D of the slip ring portion 4302 extends from the rotating component 4302C, such for interacting with a socket portion of the coupling mechanism 4108 as attached to the image display device 4106. In this manner, the ball-and-socket type of coupling mechanism 4108 arrangement can be rotated in a 360-degree plane around the longitudinal axis LA extending through the slip ring portion 4302. It can be seen that the image display device 4106 to which the ball-and-socket arrangement is coupled (e.g., as indicated by motion arrows in FIG. 44) likewise follows this rotational movement of the ball-and-socket connection to which the image display device 4106 is attached.

In various embodiments, the sleeve portion 4402 may be structured as a rigid plastic platform which provides a permanent or semi-permanent structure attached to the imaging apparatus 4104, for example, and which can be used as a mounting or attachment portion for the slip ring portion 4302. In one aspect, the imaging apparatus 4104 may be assembled with the sleeve portion 4402 pre-installed as an integral component of the imaging apparatus 4104. In certain alternative retrofit assembly embodiments of the invention, the sleeve portion 4402 may be removably connected to or detached from a pre-existing imaging apparatus 4104 in association with an imaging procedure, for example. It can be appreciated that factors such as the ability to clean, maintain, or sanitize different components of the guidance apparatus 4102 may determine which alternative structure would be best suited for a given application. For example, for medical applications where components need sufficient sanitization prior to and after use in connection with a medical procedure, a removable or detachable sleeve portion 4402 might be the optimum configuration.

As noted above, the drive mechanism 4114 may be employed in operative association with the guidance apparatus 4102 to facilitate rotation of the slip ring portion 4302 in different directions, and/or at different locations or positions, around the longitudinal axis LA of the imaging apparatus 4104. Also, an independent drive mechanism 4114 may be employed in operative association with the coupling mechanism 4108, such as to facilitate rotation of the ball-and-socket arrangement in different directions, and/or at different locations or positions, to accordingly modify the tilt or other orientation of the image display device 4106 (e.g., as represented by motion arrows included for the image display device 4106 in FIGS. 41 and 42). In this manner, the guidance apparatus 4102 can promote a more effective direct line-of-sight when using the imaging apparatus 4104 for during the performance of an imaging procedure, for example.

Figure 45B:
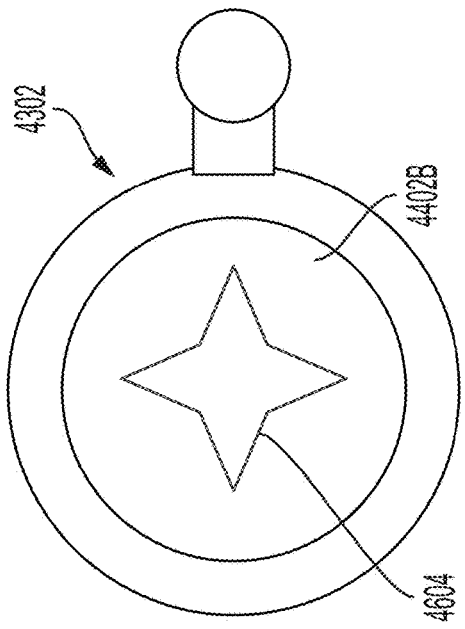
FIGS. 45A through 45D illustrate various examples of different embodiments of the structure and configuration of one example of a sleeve portion which can be structured in accordance with various embodiments of the present invention.
Figure 45D:
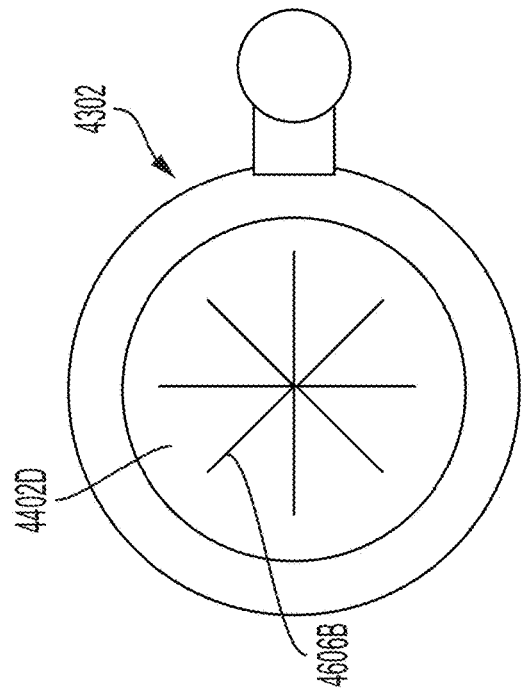
Figure 45A:
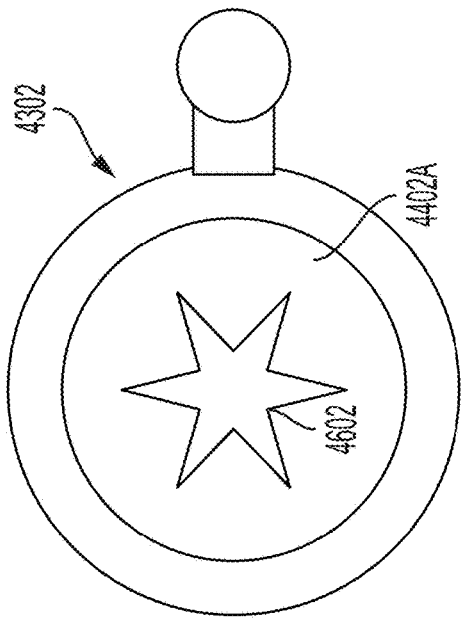
Figure 45C:
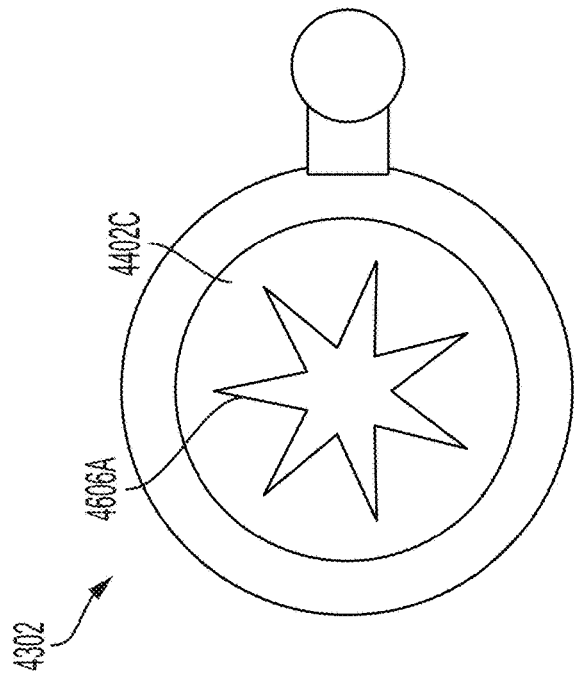

FIGS. 45A through 45D illustrate various examples of different embodiments of the structure and configuration of the sleeve portion 4402. As noted above, the sleeve portion 4402 may be comprised of a flexible material, such as an elastomeric or plastic material. The sleeve portion 4402 may be structured to facilitate passage of the main body portion of the imaging apparatus 4104 therethrough. The sleeve portion 4402 permits ready installation or removal of the imaging apparatus 4104, such as by manual insertion or removal of the imaging apparatus 4104 by a user, for example. In various embodiments, the sleeve portion 4402 may include one or more portions which resiliently biased for contact and securement of the imaging apparatus 4104 after its installation within the sleeve portion 4402. In one example, FIG. 45A illustrates a six-point star-shaped opening 4602 through which the imaging apparatus 4104 may be inserted and installed for operation within the slip ring portion 4302. In another example, FIG. 45B illustrates a four-point star-shaped opening 4604 through which the imaging apparatus 4104 may be inserted and installed for operation within the slip ring portion 4302. In another example, FIG. 45C illustrates an open state 4606A of a seven-point star-shaped opening 4606 through which the imaging apparatus 4104 may be inserted and installed for operation within the slip ring portion 4302. Similarly, FIG. 45D illustrates a closed state 4606B of the opening 4606, such as when the imaging apparatus 4104 has been removed from the sleeve portion 4402, for example.

Figure 46:
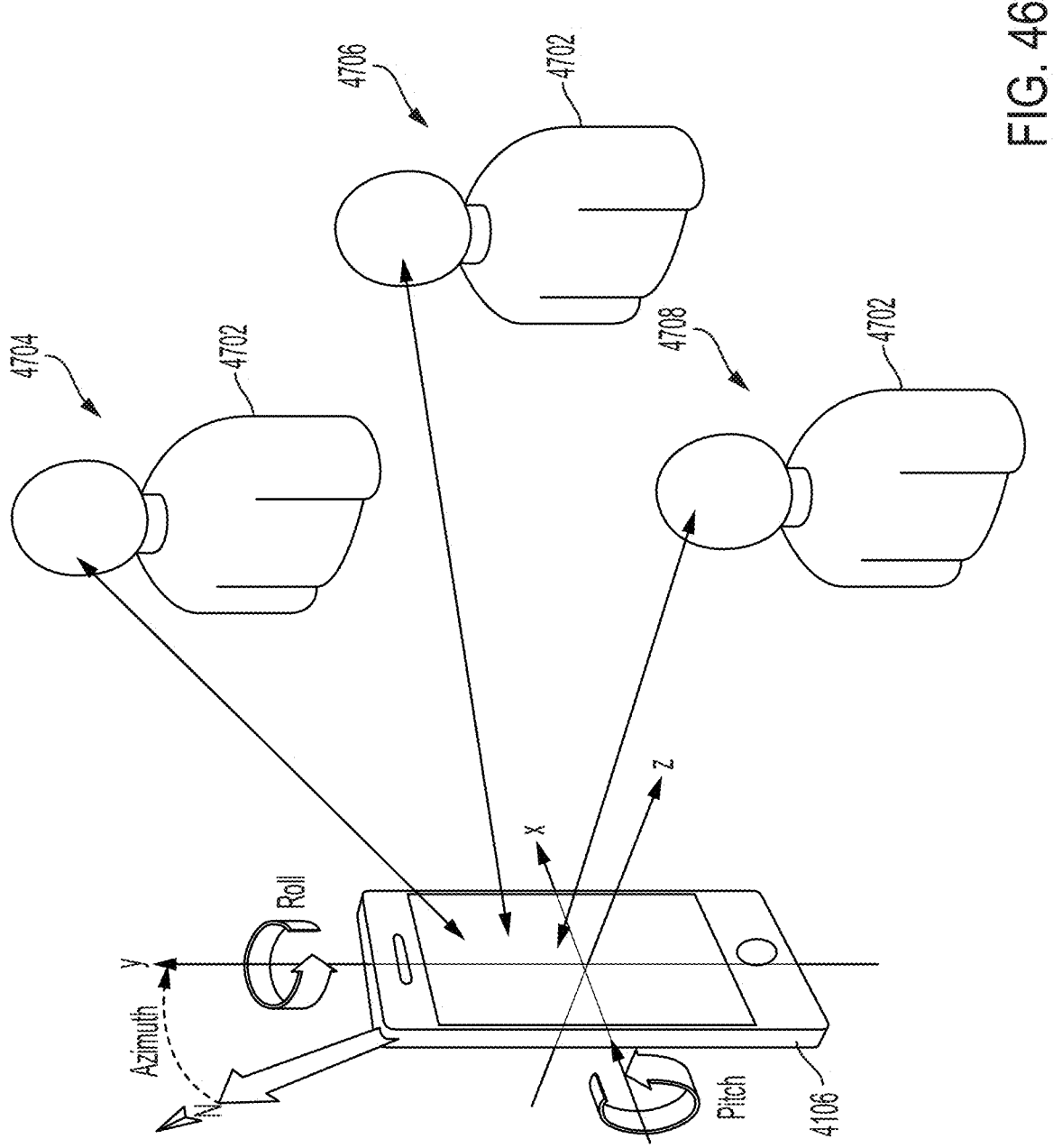
FIG. 46 depicts an example of an image display device of a guidance apparatus programmed with a facial recognition algorithm.

FIG. 46 depicts an example of the image display device 4106 of the guidance apparatus 4102 which can be programmed with a facial recognition algorithm 4112. In this example, one or both of a user 4702 (e.g., who may be performing a guided image procedure) or the image display device 4106 may move relative to each other. In different scenarios, the image display device 4106 may move in a variety of different directions (as shown), and/or the user 4702 may change positions, such as different spatial positions 4704, 4706, 4708 (as shown). In different positions or orientations of the image display device 4106 relative to the user 4702, the facial recognition algorithm 4112 initially determines whether it can identify and recognize the face of the user 4702. If the algorithm 4112 cannot adequately capture the face of the user 4702, or perhaps can only detect part of the face of the user 4702, then the drive mechanism 4114 can be actuated to move the image display device 4106 into the field of view of the user 4702. In this manner, use of the algorithm 4122 in connection with the guidance apparatus 4102 promotes a more effective direct line-of-sight field of view for the user 4702 when using the imaging apparatus 4104 for an imaging procedure.

Figure 47:
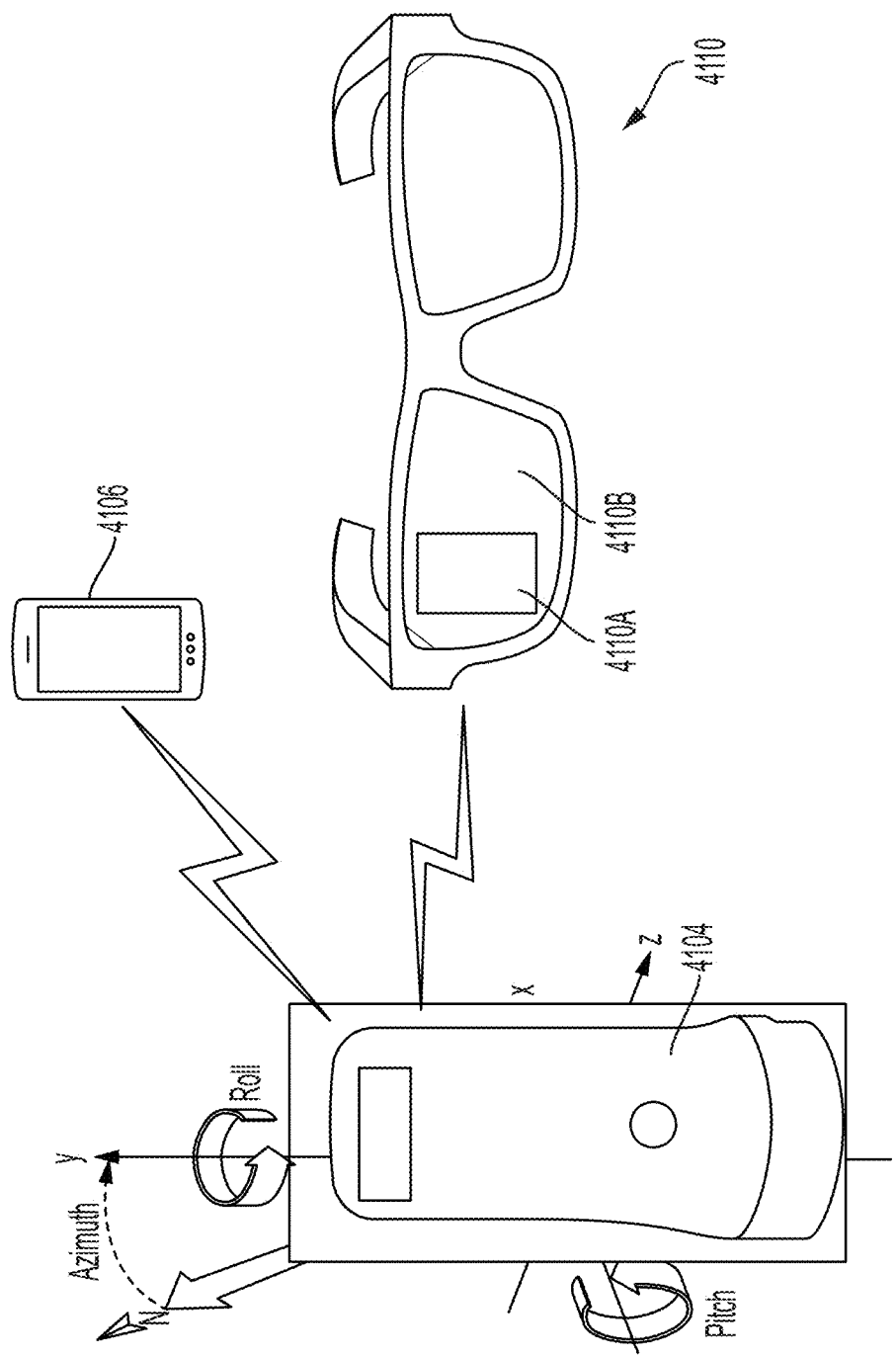
FIG. 47 illustrates one example of an eyewear viewing device enabled for wireless communication with an imaging apparatus.

In other embodiments, FIG. 47 illustrates one example of an eyewear viewing device 4110, such as smart glasses, smart goggles, or virtual reality viewing equipment, enabled for wireless communication with the imaging apparatus 4104 and/or the image display device 4106. The eyewear viewing device 4110 can be configured for wireless communication, such that the field of view processed by the imaging apparatus 4102 and/or the image display device 4106 can be communicated to the eyewear viewing device 4110. Such field of view information can be processed through circuitry and software of the eyewear viewing device 4110 and displayed on a screen display 4110A. The screen display 4110A may be rendered on at least a portion of one or both eye pieces of eyewear viewing device 4110 and presented as a solid or semi-transparent view of the field of view as seen by the imaging apparatus 4102 and/or the image display device 4106. In this example, the screen display 4110A only partially covers one of the eye pieces, leaving a field of view 4110B through the remainder of the eye piece. It can be seen that the wearer of the eyewear viewing device 4110 can be looking in a direction or location (e.g., with their head turned and eyes directed elsewhere) other than looking directly at the area which is the subject of the guided imaging procedure associated with the field of view of the imaging apparatus 4104 and/or the image display device 4106. At the same time, a direct line-of-sight field of view of the field of view of the imaging procedure area or location can be maintained for the wearer via the screen display 4110A.

Figure 48:
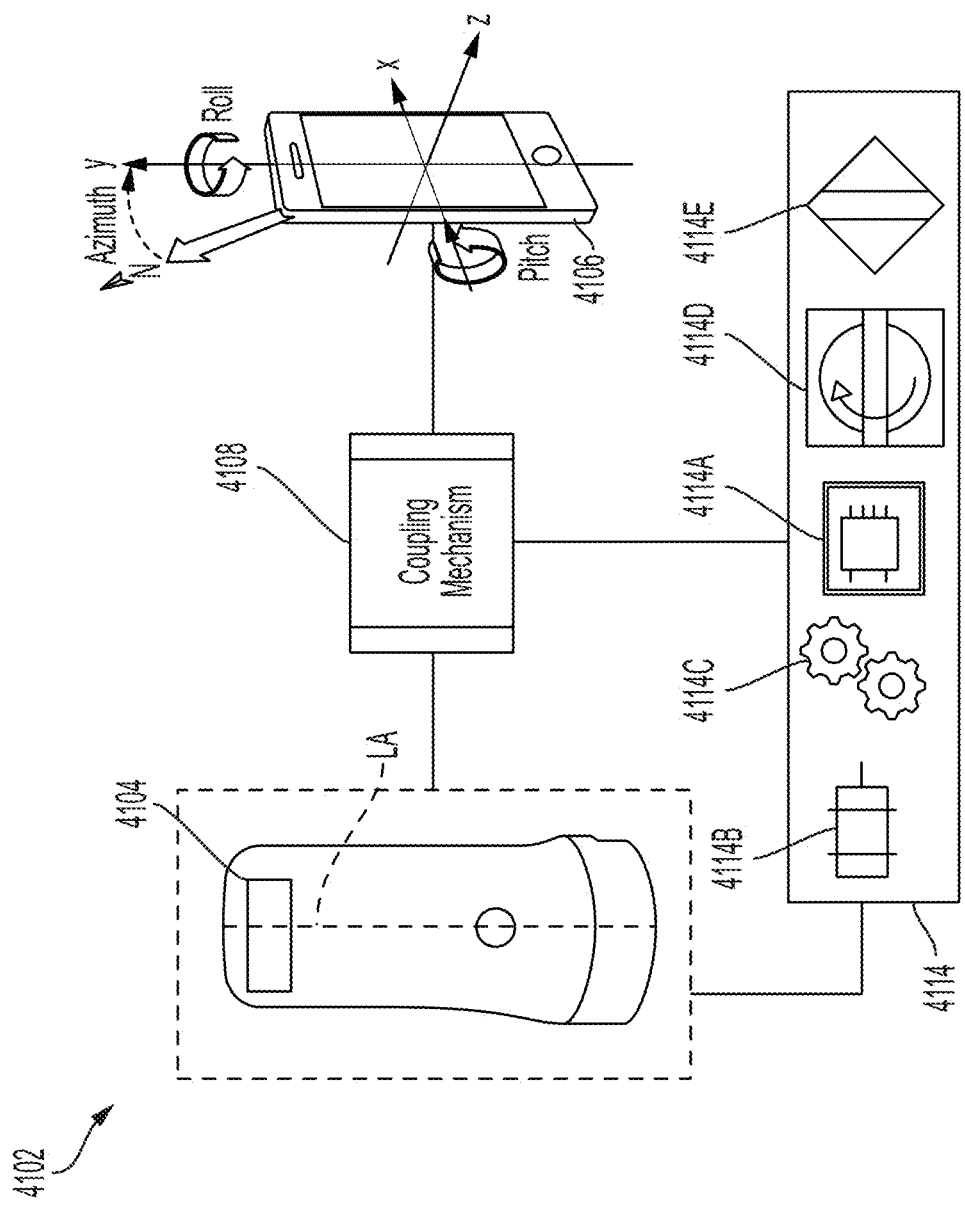
FIGS. 48 and 49 include an example of an arrangement in which the image display device is configured for communication with the coupling mechanism regarding their relative positioning and orientation during use in connection with an imaging procedure.
Figure 49:
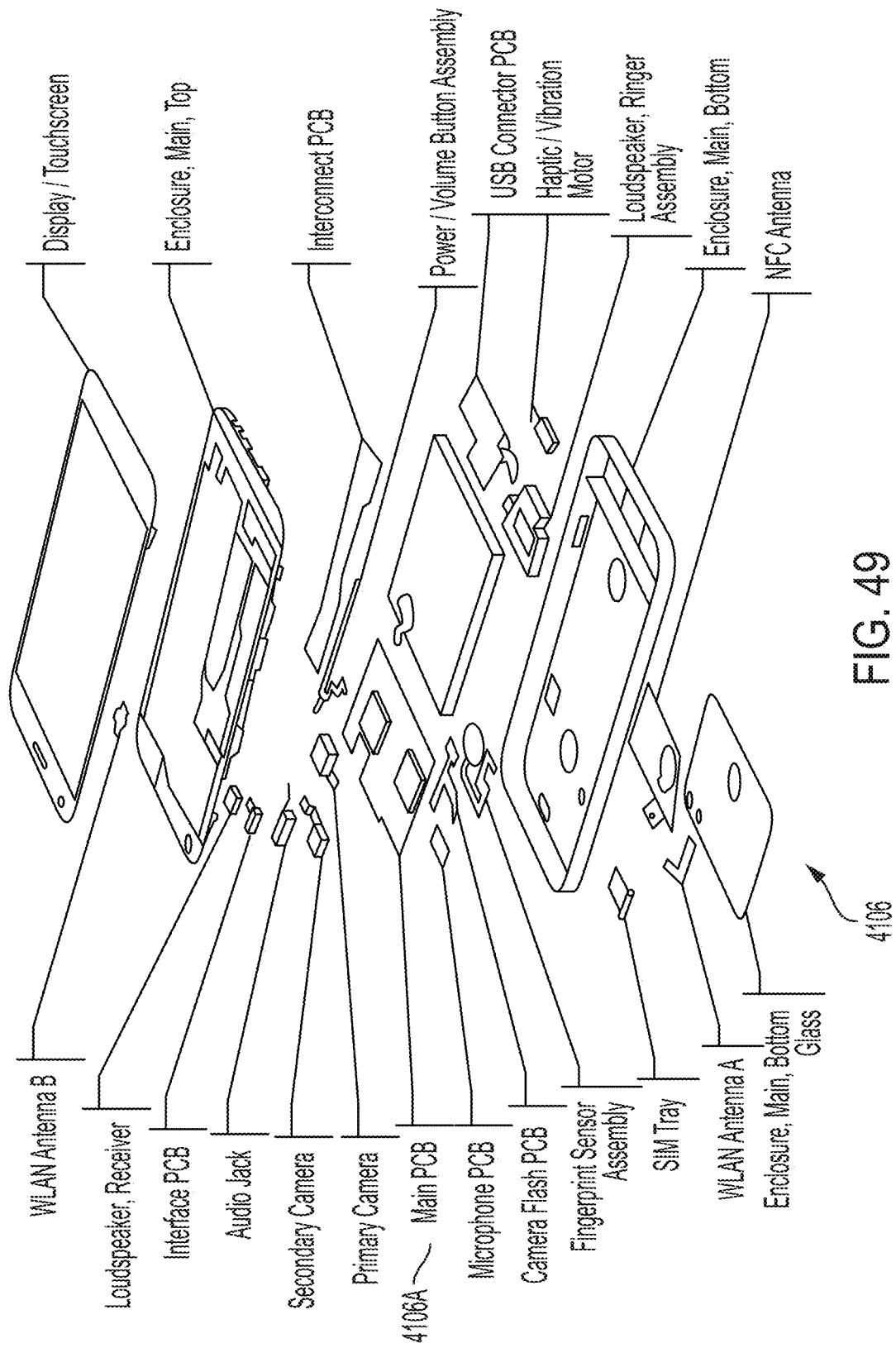

In other embodiments, FIGS. 48 and 49 include an example of an arrangement in which the image display device 4106 is configured for communication with the coupling mechanism 4108 regarding their relative positioning and orientation during use in connection with an imaging procedure. The coupling mechanism 4108 may be operatively associated with a drive mechanism 4114, which can include an operatively associated configuration of a controller 4114A, motor 4114B (e.g., a servo motor), and mechanical gears 4114C. The drive mechanism 4114 may be operatively associated with the coupling mechanism 4108 to enable movement of the components therein. Such component movement can result in changing the tilt, orientation, rotation degree, or other operative position of the coupling mechanism 4108, such as to provide more effective direct line-of-sight viewing of an area or areas of interest for the practitioner using the imaging apparatus 4104.

In this example, the drive mechanism 4114 may further include a gyroscope 4114D embodied as a micro electro mechanical systems (MEMS) gyroscope within the drive mechanism 4114. The gyroscope 4114D may include circuitry and a sensor to detect and register changes in angular displacement or linear orientation for one or more components of the guidance apparatus 4102. In certain embodiments, an accelerometer 4114E may be provided with circuitry and a sensor that senses linear changes relative to the frame of reference of components of the apparatus 4102. Working in combination, the accelerometer 4114E and the gyroscope 4114D can sense the orientation of the component device and any accelerated movement. If there is displacement that indicates acceleration in a particular direction, with a vibrating motion caused by the gyroscope 4114D, an electrical current can be generated which signals further action to be taken by the guidance apparatus 4102 and/or other components or devices operatively associated with the guidance apparatus 4102.

In addition, in this example the image display device 4106 may be embodied as a mobile phone or smart phone device, including the components shown more particularly in FIG. 49. In one aspect, the main printed circuit board 4106A or motherboard of the device 4106 may include, among other things, a gyroscope and an accelerometer structured to function similarly to the gyroscope 4114D and the accelerometer 4114E. In various embodiments, the controller 4114A of the drive mechanism 4114 and a controller of the image display device 4106 may be in data communication to share gyroscopic and accelerometric data with each other. In one aspect, adjustments may be made to the position or orientation of the coupling mechanism 4108 and/or the image display device 4106, for example, in response to comparison and analysis of data between the respective gyroscopic and/or accelerometric data. In this manner, changes in the position or orientation of the imaging apparatus 4104 relative to changes in the position or orientation of the image display device 4106 can result in appropriate adjustments to promote a more effective direct line-of-sight field of view for the user 4702 when using the imaging apparatus 4104 for an imaging procedure.

Figure 50C:
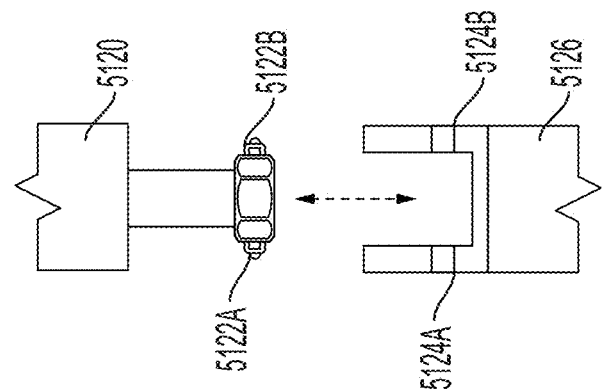
FIGS. 50A through 50C illustrate various aspects of different examples of coupling mechanisms which can be implemented in accordance with certain embodiments of the present invention.
Figure 50B:
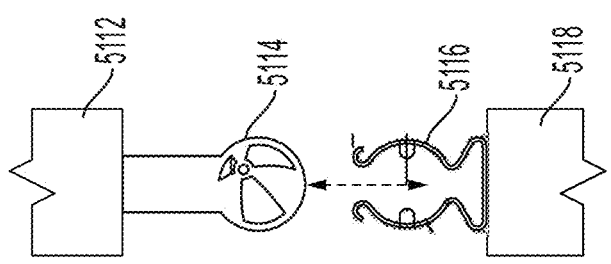
Figure 50A:
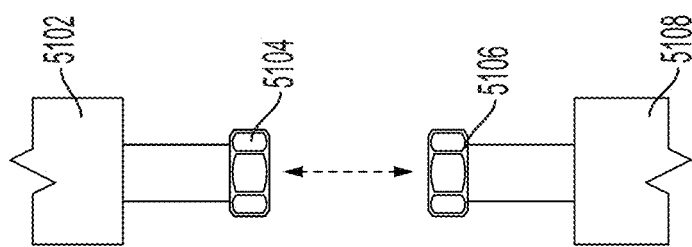

FIGS. 50A through 50C illustrate various embodiments of different examples of coupling mechanisms 4108 which can be implemented as part of practicing the present invention.

In one example, FIG. 50A includes an arrangement in which a first mounting portion 5102 structured to connect with a display 4106 (not shown) comprises a first magnetic portion 5104 designed to be removably attachable to a second magnetic portion 5106. The second magnetic portion 5106 is attached or formed as an integral component of a second mounting portion 5108 structured for operative association with a slip ring portion 4302 of the guidance apparatus 4102. In various embodiments, either or both magnetic portions 5104, 5106 comprise magnets and/or magnetic materials having oppositely polarized contacting surfaces to enable attraction between the magnetic portions 5104, 5106. It can be appreciated that the degree of the magnetic force of attraction between the magnetic portions 5104, 5106 can be designed to provide sufficient force to adequately retain the display 4106, for example, when it is mounted for use in association with the coupling mechanism 4108 and the guidance apparatus 4102.

In another example, FIG. 50B includes an arrangement in which a first mounting portion 5112 structured to connect with a display 4106 (not shown) comprises a spherical portion 5114 designed to be removably insertable into and removable from a resiliently flexible clip portion 5116. The resiliently flexible clip portion 5116 is secured to a second mounting portion 5118 structured for operative association with a slip ring portion 4302 (not shown) of the guidance apparatus 4102. It can be appreciated that the degree of the force of securement between the spherical portions 5114 when inserted into the clip portion 5116 can be designed to provide sufficient force to adequately retain the display 4106, for example, when it is mounted for use in association with the coupling mechanism 4108 and the guidance apparatus 4102.

In another example, FIG. 50C includes an arrangement in which a first mounting portion 5120 structured to connect with a display 4106 (not shown) comprises one or more ball bearing plungers (such as plungers 5122A, 5122B) designed to be removably insertable into and removable from a correspondingly mating recess portions 5124A, 5124B, as shown. The recess portions 5124A, 5124B are formed within a second mounting portion 5126 structured for operative association with a slip ring portion 4302 (not shown) of the guidance apparatus 4102. It can be appreciated that the degree of the force of securement provided by the plungers 5122 when inserted into the second mounting portion 5126 can be designed to provide sufficient force to adequately retain the display 4106, for example, when it is mounted for use in association with the coupling mechanism 4108 and the guidance apparatus 4102.

It can be appreciated that other non-physical or non-mechanical configurations can be implemented as a coupling mechanism 4108 within the guidance apparatus 4102. For example, as demonstrated by the embodiments described above in connection with FIG. 47, the coupling mechanism 4108 may be software instructions which enable communications between the display 4106 and the imaging apparatus 4104, without necessarily providing a physical or structural connection.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. For example, no particular aspect or aspects of the examples of system architectures, configurations, data definitions, or process flows described herein are necessarily intended to limit the scope of the invention, unless such aspects are specifically included in the claims.

Any element expressed herein as a means for performing a specified function is intended to encompass any way of performing that function including, for example, a combination of elements that performs that function. Furthermore, the invention, as may be defined by such means-plus-function claims, resides in the fact that the functionalities provided by the various recited means are combined and brought together in a manner as defined by the appended claims. Therefore, any means that can provide such functionalities may be considered equivalents to the means shown herein.

In various embodiments, various models or platforms can be used to practice certain aspects of the invention. For example, software-as-a-service (SaaS) models or application service provider (ASP) models may be employed as software application delivery models to communicate software applications to clients or other users. Such software applications can be downloaded through an Internet connection, for example, and operated either independently (e.g., downloaded to a laptop or desktop computer system) or through a third-party service provider (e.g., accessed through a third-party web site). In addition, cloud computing techniques may be employed in connection with various embodiments of the invention.

Moreover, the processes associated with the present embodiments may be executed by programmable equipment, such as computers. Software or other sets of instructions that may be employed to cause programmable equipment to execute the processes may be stored in any storage device, such as a computer system (non-volatile) memory. Furthermore, some of the processes may be programmed when the computer system is manufactured or via a computer-readable memory storage medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary. Memory and/or storage components may be implemented using any computer-readable media capable of storing data such as volatile or non-volatile memory, removable or non-removable memory, erasable or non-erasable memory, writeable or re-writeable memory, and so forth. Examples of computer-readable storage media may include, without limitation, RAM, dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other type of media suitable for storing information.

A "computer," "computer system," "computing apparatus," "component," or "computer processor" may be, for example and without limitation, a processor, microcomputer, minicomputer, server, mainframe, laptop, personal data assistant (PDA), wireless e-mail device, smart phone, mobile phone, electronic tablet, cellular phone, pager, fax machine, scanner, or any other programmable device or computer apparatus configured to transmit, process, and/or receive data. Computer systems and computer-based devices disclosed herein may include memory and/or storage components for storing certain software applications used in obtaining, processing, and communicating information. It can be appreciated that such memory may be internal or external with respect to operation of the disclosed embodiments. In various embodiments, a "host," "engine," "loader," "filter," "platform," or "component" may include various computers or computer systems, or may include a reasonable combination of software, firmware, and/or hardware. In certain embodiments, a "module" may include software, firmware, hardware, or any reasonable combination thereof.

In various embodiments of the present invention, a single component may be replaced by multiple components, and multiple components may be replaced by a single component, to perform a given function or functions. Any of the servers described herein, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it will be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described herein above may be implemented in computer software using any suitable computer programming language such as .NET or HTML using, for example, conventional or object-oriented techniques. Programming languages for computer software and other computer-implemented instructions may be translated into machine language by a compiler or an assembler before execution and/or may be translated directly at run time by an interpreter. Examples of assembly languages include ARM, MIPS, and x86; examples of high-level languages include Ada, BASIC, C, C++, C#, COBOL, Fortran, Java, Lisp, Pascal, Object Pascal; and examples of scripting languages include Bourne script, JavaScript, Python, Ruby, PHP, and Perl. Various embodiments may be employed in a Lotus Notes environment, for example. Such software may be stored on any type of suitable computer-readable medium or media such as, for example, a magnetic or optical storage medium.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, power line communication or G.hn. Wireless communications described herein may be conducted with WiFi and Bluetooth enabled networks and devices, among other types of suitable wireless communication protocols. The computer networks may also be embodied as one or more of the following types of networks: local area network (LAN); metropolitan area network (MAN); wide area network (WAN); virtual private network (VPN); storage area network (SAN); or global area network (GAN), among other network varieties.

For example, a WAN computer network may cover a broad area by linking communications across metropolitan, regional, or national boundaries. The network may use routers and/or public communication links. One type of data communication network may cover a relatively broad geographic area (e.g., city-to-city or country-to-country) which uses transmission facilities provided by common carriers, such as telephone service providers. In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to separately and securely conduct the traffic of different user communities over an underlying network. The VPN may provide users with the virtual experience of accessing the network through an IP address location other than the actual IP address which connects the wireless device to the network. The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods and systems described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity. As applied herein, an extranet may include a network or internetwork generally limited to a primary organization or entity, but which also has limited connections to the networks of one or more other trusted organizations or entities (e.g., customers of an entity may be given access an intranet of the entity thereby creating an extranet).

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs); remote bridges can be used to create a wide area network (WAN) link between LANs; and/or, wireless bridges can be used to connect LANs and/or to connect remote stations to LANs.

Embodiments of the methods and systems described herein may divide functions between separate CPUs, creating a multiprocessing configuration. For example, multiprocessor and multi-core (multiple CPUs on a single integrated circuit) computer systems with co-processing capabilities may be employed. Also, multitasking may be employed as a computer processing technique to handle simultaneous execution of multiple computer programs.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a processor or application specific processor.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. Discrete components and features may be readily separated from or combined with the features of any of the other several aspects without departing from the scope of the present disclosure. Any recited method can be carried out in the order of events recited or in any other order which is logically possible.

Unless specifically stated otherwise, it may be appreciated that terms such as "processing," "computing," "calculating," "determining," or the like, refer to the action and/or processes of a computer or computing system, or similar electronic computing device, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

Certain embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It will be appreciated that those skilled in the art will be able to devise various arrangements which, although not explicitly described or shown herein, embody the principles of the present disclosure and are comprised within the scope thereof. Furthermore, all examples and conditional language recited herein are principally intended to aid the reader in understanding the principles described in the present disclosure and the concepts contributed to furthering the art, and are to be construed as being without limitation to such specifically recited examples and conditions. Moreover, all statements herein reciting principles, aspects, and embodiments as well as specific examples thereof, are intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

Although various systems described herein may be embodied in software or code executed by hardware as discussed above, as an alternative the same may also be embodied in dedicated hardware or a combination of software/hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc.

The flow charts and methods described herein show the functionality and operation of various implementations. If embodied in software, each block, step, or action may represent a module, segment, or portion of code that comprises program instructions to implement the specified logical functions. The program instructions may be embodied in the form of source code that comprises human-readable statements written in a programming language or machine code that comprises numerical instructions recognizable by a suitable execution system such as a processing component in a computer system. If embodied in hardware, each block may represent a circuit or a number of interconnected circuits to implement the specified logical functions.

Reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment. The terms "a" and "an" and "the" and similar referents used in the context of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as" or "for example") provided herein is intended merely to better illuminate the disclosed embodiments and does not pose a limitation on the scope otherwise claimed. No language in the specification should be construed as indicating any non-claimed element essential to the practice of the claimed subject matter. It is further noted that the claims may be drafted to exclude any optional element. As such, this statement is intended to serve as antecedent basis for use of such exclusive terminology as solely, only and the like in connection with the recitation of claim elements, or use of a negative limitation.

Groupings of alternative elements or embodiments disclosed herein are not to be construed as limitations. Each group member may be referred to and claimed individually or in any combination with other members of the group or other elements found herein. It is anticipated that one or more members of a group may be comprised in, or deleted from, a group for reasons of convenience and/or patentability.

While various embodiments of the invention have been described herein, it should be apparent, however, that various modifications, alterations and adaptations to those embodiments may occur to persons skilled in the art with the attainment of some or all of the advantages of the present invention. The disclosed embodiments are therefore intended to include all such modifications, alterations and adaptations without departing from the scope and spirit of the present invention as described and claimed herein.

What is claimed is:

1. A guidance apparatus for use with a portable imaging apparatus and an image display device, the guidance apparatus comprising:
 a compound coupling mechanism comprising:
  a slip ring portion structured for receiving the imaging apparatus therein;
  the slip ring portion further including a sleeve portion comprised of a flexible or non-flexible material structured for conforming to or fastening to a body shape of the imaging apparatus during operation of the imaging apparatus;
  wherein the coupling mechanism is further structured for:
   facilitating orienting the image display device relative to the imaging apparatus to provide a direct line of sight of an area imaged by the imaging apparatus;
   adjusting to facilitate rotation of the image display device in multiple 360-degree planes of rotation about a longitudinal axis extending through the imaging apparatus;
   allowing the coupling mechanism, the image display device, and the imaging apparatus, in combination, to be held in a single hand of a user during performance of an imaging procedure; and, wherein the coupling mechanism further comprises a display device connecting portion structured for:
  allowing selection of an image display device position associated with a viewing angle of the image display device by facilitating adjusting the image display device between at least forward and backward positions and rotating between portrait and landscape positions;
  removably detaching or attaching the image display device from or to the coupling mechanism, thereby permitting multiple different types of image display devices to be connected to the coupling mechanism;
  removably detaching or attaching the image display device from or to the coupling mechanism, thereby permitting sterilization of the image display device and/or one or more components of the guidance apparatus; and
  removably detaching or attaching the image display device from or to the coupling mechanism, thereby permitting disposal of the coupling mechanism.

2. The guidance apparatus of claim 1, further comprising: the slip ring portion comprising:
  a rotating component rotationally engaged with the sleeve portion;
  a first connecting portion extending from the rotating component; and
  the display device connecting portion structured for operative connection with the first connecting portion and structured to be engaged with at least portion of the image display device.

3. The guidance apparatus of claim 2, further comprising top and bottom ring portions securing and confining the rotating component therein.

4. The guidance apparatus of claim 2, wherein the first connecting portion comprises a ball and the display device connecting portion comprises a socket which when coupled in combination form a ball-and-socket arrangement.

5. The guidance apparatus of claim 2, further comprising a drive mechanism operatively associated with the coupling mechanism, the drive mechanism configured for executing at least one movement of the first connecting portion.

6. The guidance apparatus of claim 2, further comprising a drive mechanism operatively associated with the coupling mechanism, the drive mechanism configured for executing at least one movement of the display device connecting portion.

7. The guidance apparatus of claim 1, further comprising a drive mechanism operatively associated with the coupling mechanism, the drive mechanism configured for executing at least one movement of the slip ring portion.

8. The guidance apparatus of claim 1, wherein the imaging apparatus comprises an ultrasound imaging apparatus.

9. The guidance apparatus of claim 1, wherein the imaging apparatus when operatively installed is wirelessly communicatively coupled to the image display device to enable displaying image data received from the imaging apparatus on a screen display of the image display device.

10. The guidance apparatus of claim 1, wherein the image display device comprises a mobile phone device.

11. The guidance apparatus of claim 1, wherein the sleeve portion further comprises an elastomeric material having a star-shaped opening formed therein.

12. The guidance apparatus of claim 1, further comprising the image display device comprising:
  at least one computer-based processor capable of executing a facial recognition algorithm;
  at least one data storage medium capable of storing the facial recognition algorithm; and
  the image display device programmed with the facial recognition algorithm.

13. The guidance apparatus of claim 12, further comprising the facial recognition algorithm programmed for initially determining recognition of at least a portion of a face of a user.

14. The guidance apparatus of claim 13, further comprising:
  a drive mechanism operatively associated with the coupling mechanism, the drive mechanism configured for executing at least one movement of the coupling mechanism; and
  the facial recognition algorithm programmed for actuating the drive mechanism to move the image display device into a position within the field of view of the user when the facial recognition algorithm cannot recognize the face of the user.

15. The guidance apparatus of claim 1, further comprising:
  a drive mechanism operatively associated with the coupling mechanism, the drive mechanism configured for executing at least one movement of the coupling mechanism;
  the drive mechanism further comprising a first gyroscope and a first accelerometer; and,
  the image display device further comprising a second gyroscope and a second accelerometer.

16. The guidance apparatus of claim 15, further comprising a controller of the drive mechanism programmed for comparing:
  at least a portion of the gyroscopic and accelerometric signals sensed by the first gyroscope and a first accelerometer,
  with at least a portion of the gyroscopic and accelerometric signals sensed by the second gyroscope and the second accelerometer.

17. The guidance apparatus of claim 16, further comprising the controller of the drive mechanism programmed for making at least one adjustment to a position or an orientation of the coupling mechanism or the image display device in response to comparing the gyroscopic and accelerometric signals.

18. A guidance apparatus for use with a portable imaging apparatus and an image display device, the guidance apparatus comprising:
  a coupling mechanism comprising:
    a slip ring portion structured for receiving the imaging apparatus therein;
    the slip ring portion further including a sleeve portion comprised of a flexible or non-flexible material structured for conforming to or fastening to a body shape of the imaging apparatus during operation of the imaging apparatus;
  wherein the coupling mechanism is further structured for:
    facilitating orienting the image display device relative to the imaging apparatus to provide a direct line of sight of an area imaged by the imaging apparatus;
    adjusting to facilitate rotation of the image display device in at least one 360-degree plane of rotation about a longitudinal axis extending through the imaging apparatus;

allowing selection of an image display device position associated with a viewing angle of the image display device; and allowing the coupling mechanism, the image display device, and the imaging apparatus, in combination, to be held in a single hand of a user during performance of an imaging procedure; and wherein the slip ring portion comprises a rotating portion rotationally engaged with the sleeve portion;

the sleeve portion further comprises a collar having a guide rail formed circumferentially around the collar, the guide rail structured for engaging with the rotating portion; and the collar further comprises a plurality of index recesses formed therein, and the rotating portion further comprises a detent tab having a protrusion extending therefrom structured for being received into each of the plurality of index recesses to provide a corresponding plurality of rotation positions of the rotating portion.

* * * * *